US009320808B2

(12) United States Patent
Chong et al.

(10) Patent No.: US 9,320,808 B2
(45) Date of Patent: *Apr. 26, 2016

(54) ACID SALT FORMS OF POLYMER-DRUG CONJUGATES AND ALKOXYLATION METHODS

(71) Applicant: Nektar Therapeutics, San Francisco, CA (US)

(72) Inventors: Anthony O. Chong, Huntsville, AL (US); Seoju Lee, Madison, AL (US); Bhalchandra V. Joshi, Madison, AL (US); Brian Bray, Huntsville, AL (US); Shaoyong Nie, Middleton, WI (US); Patrick L. Spence, Madison, AL (US)

(73) Assignee: NEKTAR THERAPEUTICS, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/284,067

(22) Filed: May 21, 2014

(65) Prior Publication Data

US 2015/0105519 A1   Apr. 16, 2015

Related U.S. Application Data

(63) Continuation of application No. 13/510,555, filed as application No. PCT/US2010/057289 on Nov. 18, 2010, now abandoned.

(60) Provisional application No. 61/262,463, filed on Nov. 18, 2009, provisional application No. 61/290,072, filed on Dec. 24, 2009.

(51) Int. Cl.
| | |
|---|---|
| *A61K 31/44* | (2006.01) |
| *A61K 31/445* | (2006.01) |
| *A61K 31/785* | (2006.01) |
| *A61K 47/48* | (2006.01) |
| *C08G 65/329* | (2006.01) |
| *C08G 65/333* | (2006.01) |
| *C07C 51/41* | (2006.01) |
| *C07C 53/18* | (2006.01) |
| *C08G 65/48* | (2006.01) |
| *C07D 491/22* | (2006.01) |
| *A61K 31/4745* | (2006.01) |

(52) U.S. Cl.
CPC ....... *A61K 47/48215* (2013.01); *A61K 31/4745* (2013.01); *C07C 51/412* (2013.01); *C07C 53/18* (2013.01); *C07D 491/22* (2013.01); *C08G 65/329* (2013.01); *C08G 65/33396* (2013.01); *C08G 65/48* (2013.01); *C08L 2203/02* (2013.01)

(58) Field of Classification Search
USPC .............. 514/280, 315, 332, 772.4
See application file for complete search history.

(56) References Cited

U.S. PATENT DOCUMENTS

| | | | |
|---|---|---|---|
| 6,403,569 B1 | 6/2002 | Achterrath | |
| 6,482,993 B1 | 11/2002 | Hofmann et al. | |
| 6,486,361 B1 | 11/2002 | Ehlers et al. | |
| 6,608,076 B1 | 8/2003 | Greenwald et al. | |
| 7,744,861 B2 | 6/2010 | Zhao et al. | |
| 2005/0043215 A1 | 2/2005 | Minko et al. | |
| 2005/0112088 A1* | 5/2005 | Zhao ................ | A61K 47/48176 424/78.27 |
| 2006/0239960 A1 | 10/2006 | Bossard et al. | |
| 2007/0031371 A1 | 2/2007 | McManus et al. | |
| 2007/0197575 A1* | 8/2007 | Zhao ..................... | A61K 31/121 514/283 |
| 2009/0074704 A1 | 3/2009 | Zhao et al. | |
| 2013/0143909 A1 | 6/2013 | Chong et al. | |

FOREIGN PATENT DOCUMENTS

| | | |
|---|---|---|
| EP | 1 258 502 | 11/2002 |
| EP | 1 798 235 | 6/2007 |
| WO | WO 2004/032862 | 4/2004 |
| WO | WO 2005/028539 | 3/2005 |
| WO | WO 2008/012365 A2 | 1/2008 |

OTHER PUBLICATIONS

Li et al., (Am. J. Health Syst. Pharm. vol. 59, pp. 539-544, published 2002).*
Australian Patent Examination Report No. 1 corresponding to Australian Patent Application No. 2010321880 date of issue Jun. 13, 2014.
Fishman, et al., "Synthesis and Investigation of Novel Branched PEG-Based Soluble Polymer Supports", J. Org. Chem., vol. 68, pp. 9843-9846, (2003).
Li, et al., "Stability of irinotecan hydrochloride in aqueous solutions", Am. J. Health-Syst. Pharm., vol. 59, pp. 539-544, (Mar. 15, 2002).
Zalipsky, et al., "Attachment of Drugs to Polyethylene Glycols", Eur. Polym. J., vol. 19, No. 12, pp. 1177-1183, (1983).
Zhao, et al., "Novel Prodrugs of SN38 Using Multiarm Poly(ethylene glycol) Linkers", Bioconjugate Chem., vol. 19, pp. 849-859, (2008).
PCT International Search Report and Written Opinion corresponding to PCT Application No. PCT/US2010/057289 date of mailing Jun. 21, 2011.
PCT International Preliminary Report on Patentability corresponding to PCT Application No. PCT/US2010/057289 date of mailing May 31, 2012.

(Continued)

*Primary Examiner* — Paul Zarek
*Assistant Examiner* — George W Kosturko
(74) *Attorney, Agent, or Firm* — Mark A. Wilson

(57) ABSTRACT

Among other aspects, provided herein is a mixed-acid salt of a water-soluble polymer-drug conjugate, along with related methods of making and using the same. The mixed-salt acid salt is stably formed, and appears to be more resistant to hydrolytic degradation than the corresponding predominantly pure acid salt or free base forms of the polymer-drug conjugate. The mixed acid salt is reproducibly prepared and recovered, and provides surprising advantages over non-mixed acid salt forms of the water-soluble polymer drug conjugate.

1 Claim, 8 Drawing Sheets

(56) References Cited

OTHER PUBLICATIONS

Chinese Notification of the First Office Action corresponding to Chinese Patent Application No. 201080061609.X date of notification Apr. 11, 2013.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-$1^{st}$, (Jan. 2003).
NOF Corporation, PEG Derivatives, Phospholipid and Drug Delivery Materials for Pharmaceuticals, 27 pages, Catalogue 2003-$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete Pegtm (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Chinese Notification of the Second Office Action corresponding to Chinese Patent Application No. 201080061609.X date of notification Jan. 1, 2014.
Eurasian Official Action corresponding to Eurasia Patent Application No. 201290342 date Nov. 28, 2013.
Chinese Notification of the Third Office Action corresponding to Chinese Patent Application No. 201080061609.X date of notification Aug. 14, 2014.
Chinese Notification of the Fourth Office Action corresponding to Chinese Patent Application No. 201080061609.X date of notification Apr. 1, 2015.
Eurasian Notification of an Official Action corresponding to Eurasian Patent Application No. 201290342 dated Feb. 2, 2015.
Japanese Notice of Reasons for Rejection corresponding to Japanese Patent Application No. 2012-540064 mailing date Oct. 7, 2014.
Japanese Notice of Reasons for Rejection corresponding to Japanese Patent Application No. 2012-540064 mailing date Jul. 7, 2015.
Mexican Communication of the substantive examination report corresponding to Mexican Patent Application No. MX/a/2012/005794 dated Nov. 12, 2014.
Eurasian Communication corresponding to Eurasian Patent Application No. 201290342 dated Feb. 2, 2016.
Israel Communication corresponding to Israel Patent Application No. 219865 dated Feb. 12, 2015.
Mexican Communication corresponding to Mexican Patent Application No. MX/a/2012/005794 dated Jul. 23, 2015.
English Translation of Notice of Reasons for Rejection corresponding to Japanese Patent Application No. 2012-540064 mailing date Feb. 3, 2016.
Mexican Communication corresponding to Mexican Patent Application No. MX/a/2012/005794 dated Feb. 2, 2016.
Chinese Notification of the Fifth Office Action corresponding to Chinese Patent Application No. 201080061609.X date of notification Dec. 8, 2015.

* cited by examiner

ACID SALT FORMS OF POLYMER-DRUG CONJUGATES AND ALKOXYLATION METHODS

CROSS-REFERENCE TO RELATED APPLICATIONS

This application is a continuation of U.S. patent application Ser. No. 13/510,555, filed Jan. 22, 2013, abandoned, which is a U.S.C. §371 application of International Application No. PCT/US2010/057289, filed Nov. 18, 2010, designating the United States, which claims the benefit of priority under 35 U.S.C. §119(e) to each of U.S. Provisional Patent Application Ser. No. 61/262,463, filed 18 Nov. 2009, and U.S. Provisional Patent Application Ser. No. 61/290,072, filed 24 Dec. 2009, all of which are incorporated herein by reference in their entireties.

FIELD

This disclosure relates generally to mixed acid salt compositions of water-soluble polymer-drug conjugates, pharmaceutical compositions thereof, and methods for preparing, formulating, administering and using such mixed acid salt compositions. This disclosure also relates generally to alkoxylation methods for preparing alkoxylated polymeric materials from a previously isolated alkoxylated oligomer, as well as to compositions comprising the alkoxylated polymeric material, methods for using the alkoxylated polymeric material, and the like.

BACKGROUND

Over the years, numerous methods have been proposed for improving the stability and delivery of biologically active agents. Challenges associated with the formulation and delivery of pharmaceutical agents can include poor aqueous solubility of the pharmaceutical agent, toxicity, low bioavailability, instability, and rapid in-vivo degradation, to name just a few. Although many approaches have been devised for improving the delivery of pharmaceutical agents, no single approach is without its potential drawbacks. For instance, commonly employed drug delivery approaches aimed at solving or at least ameliorating one or more of these problems include drug encapsulation, such as in a liposome, polymer matrix, or unimolecular micelle, covalent attachment to a water-soluble polymer such as polyethylene glycol, use of gene targeting agents, formation of salts, and the like.

Covalent attachment of a water-soluble polymer can improve the water-solubility of an active agent as well as alter its pharmacological properties. Certain exemplary polymer conjugates are described in U.S. Pat. No. 7,744,861, among others. In another approach, an active agent having acidic or basic functionalities can be reacted with a suitable base or acid and marketed in salt form. Over half of all active molecules are marketed as salts (*Polymorphism in the Pharmaceutical Industry*, Hilfiker, R., ed., Wiley-VCH, 2006). Challenges with salt forms include finding an optimal salt, as well as controlling solid state behavior during processing. Biopharmaceutical salts can be amorphous, crystalline, and exist as hydrates, solvents, various polymorphs, etc. Interestingly, rarely are salt forms, let alone mixed acid salt forms, of polymer conjugates used in drug formulations.

Another challenge associated with preparing active agent conjugates of water-soluble polymers waters is the ability to prepare relatively pure water-soluble polymers in a consistent and reproducible method. For example, poly(ethylene glycol) (PEG) derivatives activated with reactive functional groups are useful for coupling to active agents (such as small molecules and proteins), thereby forming a conjugate between the PEG and the active agent. When an active agent is conjugated to a polymer of poly(ethylene glycol) or "PEG," the conjugated active agent is conventionally referred to as having been "PEGylated."

When compared to the safety and efficacy of the active agent in the unconjugated form, the conjugated version exhibits different, and often clinically beneficial, properties. The commercial success of PEGylated active agents such as PEGASYS® PEGylated interferon alpha-2a (Hoffmann-La Roche, Nutley, N.J.), PEG-INTRON® PEGylated interferon alpha-2b (Schering Corp., Kennilworth, N.J.), and NEULASTA® PEG-filgrastim (Amgen Inc., Thousand Oaks, Calif.) demonstrates the degree to which PEGylation has the potential to improve one or more properties of an active agent.

In preparing a conjugate, a polymeric reagent is typically employed to allow for a relatively straightforward synthetic approach for conjugate synthesis. By combining a composition comprising a polymeric reagent with a composition comprising the active agent, it is possible—under the appropriate reaction conditions—to carry out a relatively convenient conjugate synthesis.

The preparation of the polymeric reagent suitable to the regulatory requirements for drug products, however, is often challenging. Conventional polymerization approaches result in relatively impure compositions and/or low yield. Although such impurities and yields may not be problematic outside the pharmaceutical field, safety and cost represent important concerns in the context of medicines for human use. Thus, conventional polymerization approaches are not suited for the synthesis of polymeric reagents intended for the manufacture of pharmaceutical conjugates.

In the case of multiarm polymers, there is a dearth of available, desirable water soluble polymers that have well controlled and well defined properties with the absence of significant amounts of undesirable impurities. Thus one can readily obtain, for example, a high molecular weight multiarm poly(ethylene glycol) but drug conjugates manufactured from commercial polymers may have significant amounts (i.e. >8%) of polymer-drug conjugate having either very low or very high molecular weight biologically active impurities. This extent of active impurities in a drug composition may render such compositions unacceptable and thus render approval of such drugs challenging if not impossible.

SUMMARY OF THE INVENTION

In one or more embodiments of the invention, a composition is provided, the composition comprising mixed salts of water soluble polymer-active agent conjugates, wherein the active agent in the conjugate has at least one amine or other basic nitrogen-containing group, and further wherein the amine or other basic nitrogen-containing group is either protonated or unprotonated (i.e., as the free base), where any given protonated amine or other basic nitrogen containing group is an acid addition salt of either a strong inorganic acid or a strong organic acid such as, for example, trifluoroacetic acid (TFA).

Examples of strong inorganic acids include hydrohalic acids (e.g., hydrochloric acid, hydrofluoric, hydroiodic, and hydrobromic), sulfuric acid, nitric acid, phosphoric acid, and nitrous acid.

In one or more embodiments of the invention, the protonated form comprises an addition salt of a hydrohalic acid.

In one or more embodiments of the invention, the protonated form comprises an addition salt of hydrochloric acid.

Examples of strong organic acids include organic acids having a pKa of less than about 2.00. Examples include trichloroacetic acid, dichloroacetic acid, as well as mixed haloacetic acids such as fluorodichloroacetic acid, fluorochloroacetic acid, chlorodifluoroacetic acid and the like.

In one or more embodiments of the invention, the water soluble polymer is linear or multi-armed.

In one or more embodiments of the invention, the water soluble polymer is a poly(alkylene glycol) such as poly(ethylene glycol) or a copolymer or terpolymer thereof.

In one or more embodiments of the invention, the active agent is selected from a small molecule drug, a peptide, and a protein.

In one or more embodiments of the invention, the active agent is a camptothecin.

In one or more embodiments of the invention, the composition comprises a mixed salt of a water-soluble polymer-active agent conjugate corresponding to structure (I):

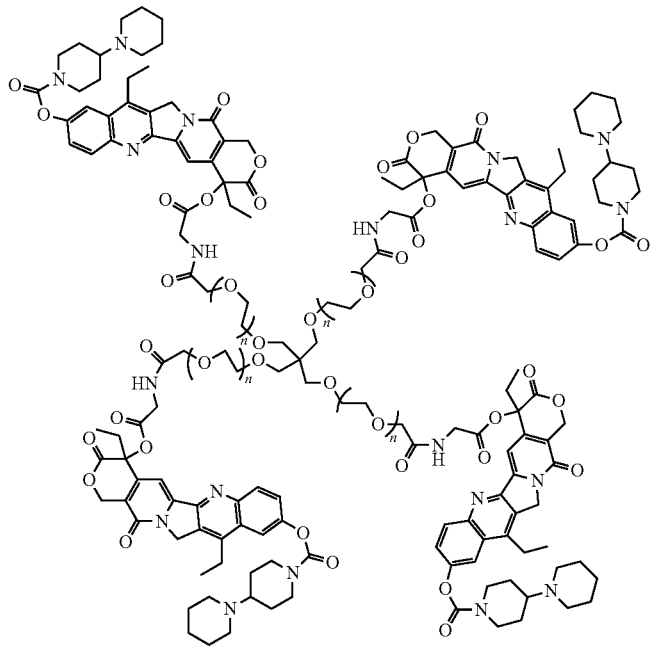

wherein n is an integer ranging from 20 to about 600 (specific protonated amino nitrogen atoms and counterions not shown), and for each amine group within each irinotecan, each amino group is either protonated or unprotonated, where any given protonated amine group is an acid salt form of an inorganic acid or an organic acid such as trifluoroacetic acid.

In one or more embodiments of the invention, with respect to a composition of conjugates (e.g., a composition of four-arm conjugates) the mole percent of active agent amino groups (or other basic nitrogen atoms) in the composition that are protonated as the TFA salt is greater than each of the mole percent of active agent amino groups in the composition that are protonated as an inorganic acid salt and the mole percent of active agent amino groups in the composition in free base form.

In yet an alternative embodiment, with respect to a composition of conjugates (e.g., a composition of four-arm conjugates) the mole percent of active agent amine groups (or other basic nitrogen atoms) in the composition that are protonated as the TFA salt is greater than the mole percent of active agent amine groups in the composition that are in free base (i.e. unprotonated) form.

In one or more embodiments of the invention, with respect to a composition of conjugates (e.g., a composition of four-arm conjugates) at least 20 mole percent of active agent amine groups in the composition are protonated as the TFA salt.

In one or more embodiments, with respect to a composition of conjugates (e.g. a composition of four-arm conjugates) at least 25 mole percent of active agent amine groups in the composition are protonated as the TFA salt.

In one or more embodiments of the invention, with respect to a composition of conjugates (e.g., a composition of four-arm conjugates), about 20-45 mole percent of active agent amino groups in the composition are protonated as the TFA salt.

In one or more embodiments of the invention, with respect to a composition of conjugates (e.g., a composition of four-arm conjugates), about 24-38 mole percent of active agent amino groups in the composition are protonated as the TFA salt.

In one or more embodiments of the invention, with respect to a composition of conjugates (e.g., a composition of four-arm conjugates), about 35-65 mole percent of active agent amino groups in the composition are protonated as the TFA salt.

In one or more embodiments of the invention, with respect to a composition of conjugates (e.g., a composition of four-arm conjugates), about 30-65 mole percent of the active agent amino groups in the composition are protonated as an inorganic acid salt (such as the HCl salt).

In yet one or more additional embodiments of the invention, with respect to a composition of conjugates (e.g., a composition of four-arm conjugates), about 32-60 mole percent of the active agent amino groups in the composition are protonated as an inorganic acid salt (such as the HCl salt).

In yet one or more further embodiments of the invention, with respect to a composition of conjugates (e.g., a composition of four-arm conjugates), about 35-57 mole percent of the active agent amino groups in the composition are protonated as an inorganic acid salt (such as the HCl salt).

In one or more embodiments of the invention, with respect to a composition of conjugates (e.g. a composition of four-arm conjugates), about 25-40 mole percent of the active agent amino groups in the composition are protonated as an inorganic acid sail (such as the HCl salt), and about 5-35 mole percent of the active agent amino groups in the composition are non-protonated (i.e., as the free base).

In one or more embodiments of the invention, with respect to a composition of conjugates (e.g., a composition of four-arm conjugates), about 32-60 mole percent of the active agent amino groups in the composition are protonated as an inorganic acid salt (such as the HCl salt), and about 5-35 mole percent of the active agent amino groups in the composition are non-protonated (i.e., as the free base).

In one or more embodiments of the invention, a trifluoroacetic acid/hydrochloric acid mixed salt of a conjugate is provided, the conjugate having the following structure:

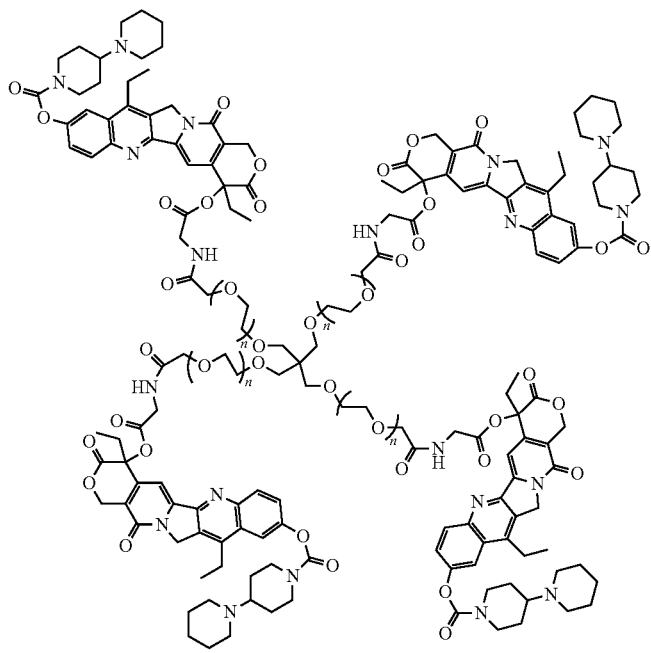

wherein n is an integer ranging from about 20 to about 500 (including about 40 to about 500) (noting that in the above structure, specific basic nitrogen atoms in protonated form and corresponding anions are not shown). In one or more embodiments of the invention, a portion of amino groups in conjugate encompassed by the structure immediately above are non-protonated. Exemplary molar ratios of protonated and non-protonated forms as provided above and further herein apply to the foregoing conjugate.

In one or more embodiments of the invention, a method for providing a mixed salt of a water-soluble polymer-active agent conjugate is provided, comprising the steps of: (i) deprotecting an inorganic acid salt of an amine-containing active agent in protected form by treatment with trifluoroacetic acid (TFA) or other organic acid deprotecting reagent to form a deprotected active agent acid salt, (ii) coupling the deprotected active agent acid salt of step (i) with a water-soluble polymer reagent in the presence of a base (e.g. trimethyl amine, triethyl amine, and dimethylamino-pyridine) to form a polymer-active agent conjugate, and (iii) recovering the polymer-active agent conjugate, where the recovered polymer-active agent conjugate is characterized by having active agent amino groups therein individually present in a form selected from the group consisting of free base form (non-protonated), inorganic acid salt form, and TFA or other organic acid salt form. In one or more embodiments of the invention, the method further comprises determining the relative molar amounts of inorganic acid and TFA in the deprotected acid salt formed in step (i). In one or more embodiments of the invention, the inorganic acid salt in step (i) is a hydrohalic acid salt such as a hydrochloric acid salt. In one or more embodiments of the invention, the amount of base in step (ii) ranges from 1.00-2.00 (moles TFA+moles acid). In one or more related embodiments, the amount of base in step (ii) ranges from 1.00 to 1.50 (moles TFA+moles inorganic acid), where the parenthesis indicates multiplication. In one or more related embodiments, the amount of base in step (ii) ranges from 1.00 to 1.20 (moles TFA+moles inorganic acid).

In one particular embodiment, the number of equivalents of base is 1.05 ((moles TFA+moles inorganic acid).

In one or more embodiments of the invention, the water-soluble polymer reagent is an activated polyethylene glycol ester (i.e., a polyethylene glycol reagent having at least one activated ester group). In one or more embodiments of the invention, the water-soluble polymer reagent is a polyethylene glycol reagent having three or more polymer arms.

In one or more embodiments of the invention, the active agent amine groups in the polymer-active agent conjugate are selected from the group consisting of secondary amine groups and tertiary amine groups. In one or more embodiments of the invention, the active agent amine groups are tertiary amino groups. In yet another embodiment, the polymer-active agent conjugate comprises a basic nitrogen atom that, as its corresponding conjugate acid, has a $pK_a$ in a range of about 10-11.5.

In one or more embodiments of the invention, the active agent is selected from a small molecule, a peptide and a protein. In one or more embodiments of the invention, the active agent is a camptothecin. Illustrative camptothecin molecules are selected from camptothecin, irinotecan, and 7-ethyl-10-hydroxy-camptothecin (SN-38). Exemplary sites for covalent attachment to a water-soluble polymer include the 7-, 10-, and 20-ring positions of the camptothecin skeleton, among others.

In one or more embodiments of the invention, a pharmaceutically acceptable composition is provided, the pharmaceutically acceptable composition comprising (i) a mixed salt according to any one or more of the embodiments described herein, and (ii) lactate buffer, optionally in lyophilized form. In one or more embodiments of the invention, the pharmaceutically acceptable composition is a sterile composition. In one or more embodiments of the invention, the pharmaceutically acceptable composition is optionally provided in a container (e.g. a vial), optionally containing the equivalent of a 100-mg dose of irinotecan in unconjugated form.

In one or more embodiments of the invention, a method is provided, the method comprising administering a conjugate-containing composition described herein (where the active agent is an anti-cancer agent) to an individual suffering from one or more types of cancerous solid tumors, wherein the conjugate-containing composition is optionally dissolved in a solution of 5% w/w dextrose. In one or more embodiments of the invention, administration is effected via intravenous infusion.

In one or more embodiments of the invention, a method for preparing a mixed salt of a water-soluble polymer-active agent conjugate is provided, the method comprising the steps of: (i) deprotecting t-Boc glycine-irinotecan.HCl by treatment with trifluoroacetic acid (TFA) to form deprotected glycine-irinotecan HCl/TFA mixed salt, (ii) coupling the deprotected glycine-irinotecan HCl/TFA mixed salt with 4-arm-pentaerythritolyl-polyethylene glycol-carboxymethyl succinimide in the presence of a base under conditions effective to form a conjugate, 4-arm-pentaerythritolyl-polyethylene glycol-carboxymethyl glycine-irinotecan (also referred to as pentaerythritolyl-4-arm-(PEG-1-methylene-2-oxo-vinylamino acetate linked-Irinotecan) and (iii) recovering the conjugate from step (ii), wherein the conjugate is a mixed salt comprising amine groups in a combination of free base, HCl, and TFA salt form. In one or more embodiments of the invention, the method further comprises purifying the conjugate (e.g., comprising recrystallizing the conjugate to form a recrystallized conjugate). In one or more embodiments of the invention, a recrystallized product is provided, the recrystallized product being a mixed acid salt comprising active agent amino groups existing as a combination of free base, HCl, and TFA salt forms.

In one or more embodiments of the invention, a method of treating a mammal suffering from cancer is provided, the method comprising administering a therapeutically effective amount of a mixed salt of a water soluble polymer-camptothecin conjugate comprising a camptothecin having amine or other basic nitrogen containing groups in both free base and in protonated form, where the each protonated form exists as an acid addition salt of either a strong inorganic acid and trifluoroacetic acid. The mixed acid salt is administered to the mammal effective to produce a slowing or inhibition of solid tumor growth in the subject. In one or more embodiments of the invention, the cancerous solid tumor is selected from the group consisting of colorectal, ovarian, cervical, breast and non-small cell lung.

In one or more embodiments of the invention, a mixed acid salt of an active agent conjugate as described herein is provided, wherein the active is an anti-cancer agent for the manufacture of a medicament for treating cancer.

In another aspect, a method is provided, the method comprising the step of alkoxylating in a suitable solvent a previously isolated alkoxylatable oligomer to form an alkoxylated polymeric product, wherein the previously isolated alkoxylatable oligomer has a known and defined weight-average molecular weight of greater than 300 Daltons (e.g., greater than 500 Daltons).

In one or more embodiments of the foregoing aspect of the invention, a composition is provided, the composition comprising an alkoxylated polymeric product prepared by a method comprising the step of alkoxylating in a suitable solvent a previously isolated alkoxylatable oligomer to form an alkoxylated polymeric product, wherein the previously isolated alkoxylatable oligomer has a known and defined weight-average molecular weight of greater than 300 Daltons (e.g., greater than 500 Daltons).

In one or more embodiments of the invention, a composition is provided, the composition comprising an alkoxylated polymeric product having a purity of greater than 92 wt % and the total combined content of high molecular weight products and diols is less than 8 wt % (e.g., less than 2 wt %), as determined by, for example, gel filtration chromatography (GFC) analysis.

In one or more embodiments of the invention, the alkoxylated polymer product has the following structure:

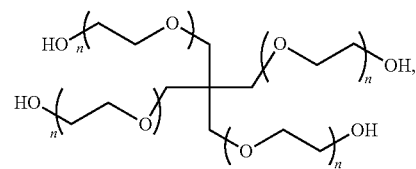

wherein each n is an integer from 20 to 1000 (e.g., from 50 to 1000).

In one or more embodiments of the invention, a method is provided, the method comprising the steps of (i) alkoxylating in a suitable solvent a previously isolated alkoxylatable oligomer to form an alkoxylated polymeric material, wherein the previously isolated alkoxylatable oligomer has a known and defined weight-average molecular weight of greater than 300 Daltons (e.g., greater than 500 Daltons), and (ii) optionally, further activating the alkoxylated polymeric product to provide an activated alkoxylated polymeric product that is useful as (among other things) a polymeric reagent for preparing polymer-drug conjugates.

In one or more embodiments of the invention, a method is provided, the method comprising the step of activating an alkoxylated polymeric product obtained from and/or contained within a composition comprising an alkoxylated polymeric product having a purity of greater than 90% to thereby form an activated alkoxylated polymeric product that is useful as (among other things) a polymer reagent for preparing polymer-drug conjugates.

In one or more embodiments of the invention, a method is provided, the method comprising the step of conjugating an activated alkoxylated polymeric product to an active agent, wherein the activated alkoxylated polymeric product was prepared by a method comprising the step of activating an alkoxylated polymeric product obtained from and/or contained within a composition comprising an alkoxylated polymeric product having a purity of greater than 90% to thereby form an activated alkoxylated polymeric product.

In one or more embodiments of the invention, a mixed salt of a water-soluble polymer-active agent conjugate is provided, the conjugate having been prepared by coupling (under conjugation conditions) an amine-bearing active agent (e.g., a deprotected glycine-irinotecan) to a polymer reagent (e.g. a 4-arm pentaerythritolyl-poly(ethylene glycol)-carboxymethyl succinimide) in the presence of a base to form a conjugate, wherein the conjugate is in the form of a mixed salt conjugate (e.g., the conjugate possesses nitrogen atoms, each one of which will either be protonated or unprotonated, where any given protonated amino group is an acid salt possessing one of two different anions), and further wherein, optionally, the polymer reagent is prepared from an alkoxylation product prepared as described herein.

Additional embodiments of the present method, compositions, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

Figure 1:
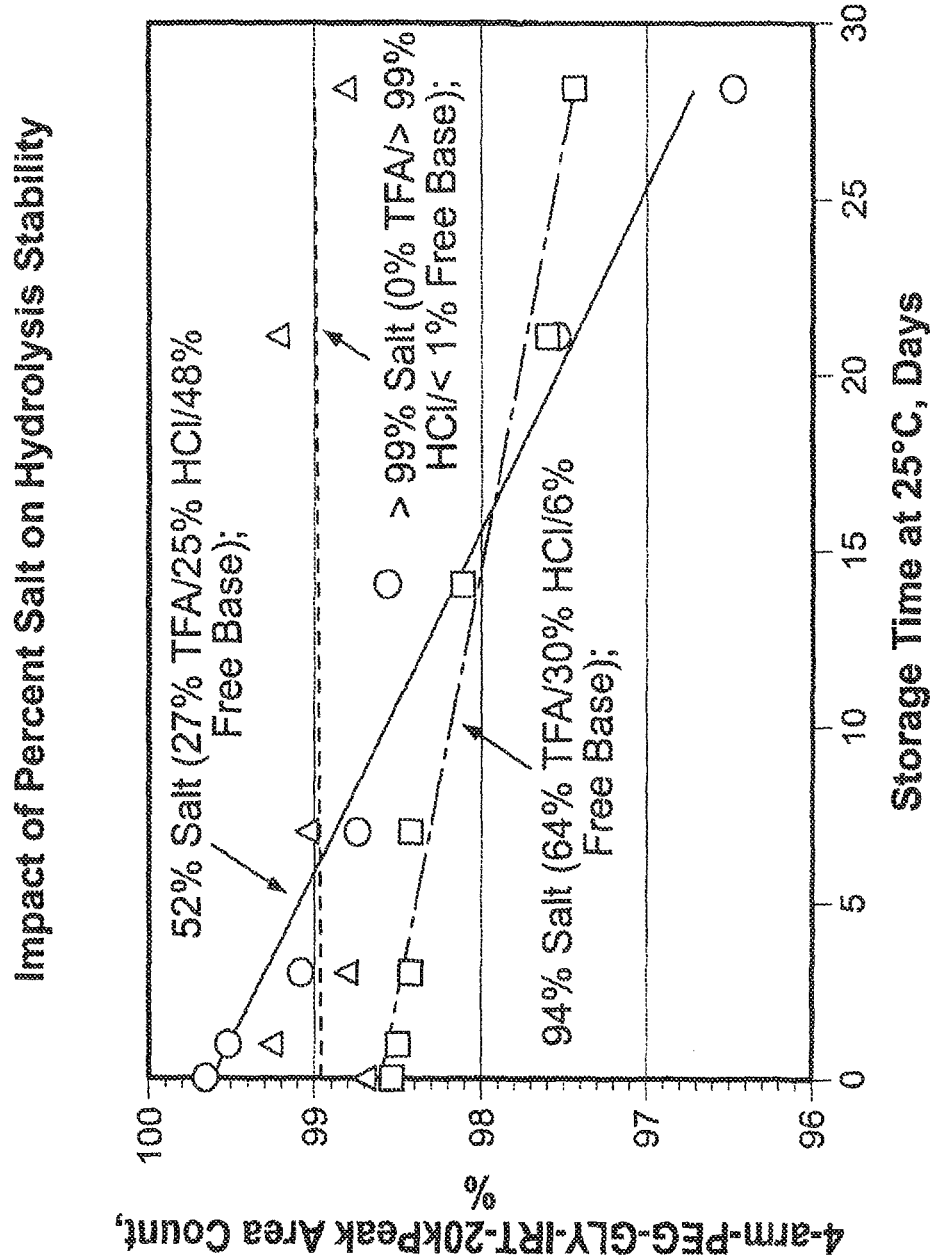
FIG. 1 is a graph illustrating the results of stress stability studies on three different samples of 4-arm-PEG-Gly-Irino-20K, each having a different composition with respect to relative amounts of trifluoroacetic acid and hydrochloride salts, as well as free base. Samples tested included >99% HCl salt (<1% free base, triangles), 94% total salt (6% free base, squares), and 52% total salt (48% free base, circles). The samples were stored at 25° C. and 60% relative humidity; the plot illustrates degradation of compound over time, as described in detail in Example 3.

Various aspects of the invention now will be described more fully hereinafter. Such aspects may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entireties. In the event of an inconsistency between the teachings of this specification and the art incorporated by reference, the meaning of the teachings in this specification shall prevail.

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

A "functional group" is a group that may be used, under normal conditions of organic synthesis, to form a covalent linkage between the entity to which it is attached and another entity, which typically bears a further functional group. The functional group generally includes multiple bond(s) and/or heteroatom(s). Preferred functional groups are described herein.

The term "reactive" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups that may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition. Wiley, New York, 1999, and in P. J. Kocienski, *Protecting Groups*, Third Ed., Thieme Chemistry, 2003, and references cited therein.

A functional group in "protected form" refers to a functional group bearing a protecting group. As used herein, the term "functional group" or any synonym thereof is meant to encompass protected forms thereof.

"PEG" or "poly(ethylene glycol)" as used herein, is meant to encompass any water-soluble poly(ethylene oxide). Typically, PEGs for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced. e.g., during a synthetic transformation. The variable (n) ranges from 3 to about 3000, and the terminal groups and architecture of the overall PEG may vary.

A water-soluble polymer may bear one or more "end-capping group," (in which case it can stated that the water-soluble polymer is "end-capped." With regard to end-capping groups, exemplary end-capping groups are generally carbon- and hydrogen-containing groups, typically comprised of 1-20 carbon atoms and an oxygen atom that is covalently bonded to the group. In this regard, the group is typically alkoxy (e.g., methoxy, ethoxy and benzyloxy) and with respect to the carbon-containing group can optionally be saturated or unsaturated, as well as aryl, heteroaryl, cyclo, heterocyclo, and substituted forms of any of the foregoing.

The end-capping group can also comprise a detectable label. When the polymer has an end-capping group comprising a detectable label, the amount or location of the polymer and/or the moiety (e.g., active agent) to which the polymer is attached can be determined by using a suitable detector. Such labels include, without limitation, fluorescers, chemiluminescers, moieties used in enzyme labeling, colorimetric (e.g., dyes), metal ions, radioactive moieties, and the like.

"Water-soluble", in the context of a polymer of the invention or a "water-soluble polymer segment" is any segment or polymer that is at least 35% (by weight), preferably greater than 70% (by weight), and more preferably greater than 95% (by weight) soluble in water at room temperature. Typically, a water-soluble polymer or segment will transmit at least about 75%, more preferably at least about 95% of light, transmitted by the same solution after filtering.

The term "activated," when used in conjugation with a particular functional group, refers to a reactive functional group that reacts readily with an electrophile or nucleophile on another molecule. This is in contrast to those groups that require strong bases or highly impractical reaction conditions in order to react (i.e., a "nonreactive" or "inert" group).

"Electrophile" refers to an ion or atom or a neutral or ionic collection of atoms having an electrophilic center, i.e., a center that is electron seeking or capable of reacting with a nucleophile.

"Nucleophile" refers to an ion or atom or a neutral or ionic collection of atoms having a nucleophilic center, i.e., a center that is seeking an electrophilic center or capable of reacting with an electrophile.

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W. et al., *Protective Groups in Organic Synthesis*, 3rd ed., John Wiley & Sons, New York, N.Y. (1999).

"Molecular mass" in the context of a water-soluble polymer such as PEG, refers to the weight average molecular weight of a polymer, typically determined by size exclusion chromatography, light scattering techniques, or intrinsic viscosity determination in an organic solvent like 1,2,4-trichlorobenzene.

The terms "spacer" and "spacer moiety" are used herein to refer to an atom or a collection of atoms optionally used to link interconnecting moieties such as a terminus of a series of monomers and an electrophile. The spacer moieties of the invention may be hydrolytically stable or may include a physiologically hydrolyzable or enzymatically degradable linkage.

A "hydrolyzable" bond is a relatively labile bond that reacts with water (i.e., is hydrolyzed) under physiological conditions. The tendency of a bond to hydrolyze in water will depend not only on the general type of linkage connecting two central atoms but also on the substituents attached to these central atoms. Illustrative hydrolytically unstable linkages include carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g. in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multi-armed" in reference to the geometry or overall structure of a polymer refers to polymer having 3 or more polymer-containing "arms" connected to a "core" molecule or structure. Thus, a multi-armed polymer may possess 3 polymer arms, 4 polymer arms, 5 polymer arms, 6 polymer arms, 7 polymer arms, 8 polymer arms or more, depending upon its configuration and core structure. One particular type of multi-armed polymer is a highly branched polymer referred to as a dendritic polymer or hyperbranched polymer having an initiator core of at least 3 branches, an interior branching multiplicity or 2 or greater, a generation of 2 or greater, and at least 25 surface groups within a single dendrimer molecule. For the purposes herein, a dendrimer is considered to possess a structure distinct from that of a multi-armed polymer. That is to say, a multi-armed polymer as referred to herein explicitly excludes dendrimers. Additionally, a multi-armed polymer as provided herein possesses a non-crosslinked core.

A "dendrimer" or "hyperbranched polymer" is a globular, size monodisperse polymer in which all bonds emerge radially from a central focal point or core with a regular branching pattern and with repeat units that each contribute a branch point. Dendrimers are typically although not necessarily formed using a nano-scale, multistep fabrication process. Each step results in a new "generation" that has two or more times the complexity of the previous generation. Dendrimers exhibit certain dendritic state properties such as core encapsulation, making them unique from other types of polymers.

"Branch point" refers to a bifurcation point comprising one or more atoms at which a polymer splits or branches from a linear structure into one or more additional polymer arms. A multi-arm polymer may have one branch point or multiple branch points, so long as the branches are not regular repeats resulting in a dendrimer.

"Substantially" or "essentially" means nearly totally or completely, for instance, 95% or greater of some given quantity.

"Alkyl" refers to a hydrocarbon chain ranging from about 1 to 20 atoms in length. Such hydrocarbon chains are preferably but not necessarily saturated and may be branched or straight chain. Exemplary alkyl groups include methyl, ethyl, isopropyl, n-butyl, n-pentyl, 2-methyl-1-butyl, 3-pentyl, 3-methyl-3-pentyl, and the like.

"Lower alkyl" refers to an alkyl group containing from 1 to 6 carbon atoms, and may be straight chain or branched, as exemplified by methyl, ethyl, n-butyl, i-butyl and t-butyl.

"Cycloalkyl" refers to a saturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl." refers to a moiety (e.g. an alkyl group) substituted with one or more non-interfering substituents, such as, but not limited to: $C_3$-$C_8$ cycloalkyl, e.g. cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta or para).

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

As used herein, "alkenyl" refers to branched and unbranched hydrocarbon groups of 1 to 15 atoms in length, containing at least one double bond, such as ethenyl (vinyl), 2-propen-1-yl (allyl), isopropenyl, 3-buten-1-yl, and the like.

The term "alkynyl" as used herein refers to branched and unbranched hydrocarbon groups of 2 to 15 atoms in length, containing at least one triple bond, such as ethynyl, 1-propynyl, 3-butyn-1-yl, 1-octyn-1-yl, and so forth.

The term "aryl" means an aromatic group having up to 14 carbon atoms. Aryl groups include phenyl, naphthyl, biphenyl, phenanthrecenyl, naphthacenyl, and the like.

"Substituted phenyl" and "substituted aryl" denote a phenyl group and aryl group, respectively, substituted with one, two, three, four, or five (e.g., 1-2, 1-3, 1-4, or 1-5 substituents) chosen from halo (F, Cl, Br, I), hydroxyl, cyano, nitro, alkyl (e.g., $C_{1-6}$ alkyl), alkoxy (e.g., $C_{1-6}$ alkoxy), benzyloxy, carboxy, aryl, and so forth.

An inorganic acid is an acid that is absent carbon atoms. Examples include hydrohalic acids, nitric acid, sulfuric acid, phosphoric acid and the like.

"Hydrohalic acid" means a hydrogen halide such as hydrofluoric acid (HF), hydrochloric acid (HCl), hydrobromic acid (HBr), and hydroiodic acid (HI).

"Organic acid" means any organic compound (i.e., having at least one carbon atom) possessing one or more carboxy groups (—COOH). Some specific examples include formic acid, lactic acid, benzoic acid, acetic acid, trifluoroacetic acid, dichloroacetic acid, trichloroacetic acid, mixed chlorofluoroacetic acids, citric acid, oxalic acid, and the like.

"Active agent" as used herein includes any agent, drug, compound, and the like which provides some pharmacologic, often beneficial, effect that can be demonstrated in-vivo or in vitro. As used herein, these terms further include any physiologically or pharmacologically active substance that produces a localized or systemic effect in a patient. As used herein, especially in reference to synthetic approaches described herein, a "active agent" is meant to encompass derivatized or linker modified versions thereof, such that upon administration in vivo, the parent "bioactive" molecule is released.

"Pharmaceutically acceptable excipient" and "pharmaceutically acceptable carrier" refer to an excipient that can be included in a composition comprising an active agent and that causes no significant adverse toxicological effects to the patient.

"Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in a target tissue or site in the body. The precise amount will depend upon numerous factors, e.g., the particular active agent, the components and physical characteristics of the pharmaceutical preparation, intended patient population, and patient considerations, and can readily be determined by one skilled in the art, based upon the information provided herein and available in the relevant literature.

"Multi-functional" in the context of a polymer means a polymer having 3 or more functional groups, where the functional groups may be the same or different, and are typically present on the polymer termini. Multi-functional polymers will typically contain from about 3-100 functional groups, or from 3-50 functional groups, or from 3-25 functional groups, or from 3-15 functional groups, or from 3 to 10 functional groups, i.e., contains 3, 4, 5, 6, 7, 8, 9 or 10 functional groups.

"Difunctional" and "bifunctional" are used interchangeably herein and mean an entity such as a polymer having two functional groups contained therein, typically at the polymer termini. When the functional groups are the same, the entity is said to be homodifunctional or homobifunctional. When the functional groups are different, the entity is said to be heterodifunctional or heterobifunctional.

A basic or acidic reactant described herein includes neutral, charged, and any corresponding salt forms thereof.

The terms "subject," "individual" and "patient" are used interchangeably herein and refer to a vertebrate, preferably a mammal. Mammals include, but are not limited to, murines, rodents, simians, humans, farm animals, sport animals and pets. Such subjects are typically suffering from or prone to a condition that can be prevented or treated by administration of a water-soluble polymer-active agent conjugate as described herein.

The term "about," particularly in reference to a given quantity, is meant to encompass deviations of plus or minus five percent.

"Treatment" and "treating" of a particular condition include: (1) preventing such a condition, i.e., causing the condition not to develop, or to occur with less intensity or to a lesser degree in a subject that may be exposed to or predisposed to the condition but does not yet experience or display the condition, and (2) inhibiting the condition, i.e., arresting the development or reversing the condition.

"Optional" or "optionally" means that the subsequently described circumstance may but need not necessarily, so that the description includes instances where the circumstance occurs and instances where it does not.

A "small molecule" is an organic, inorganic, or organometallic compound typically having a molecular weight of less than about 1000, preferably less than about 800 daltons. Small molecules as referred to herein encompass oligopeptides and other biomolecules having a molecular weight of less than about 1000.

A "peptide" is a molecule composed of from about 13 to 50 or so amino acids. An oligopeptide typically contains from about 2 to 12 amino acids.

Unless explicitly stated to the contrary, the terms "partial mixed salt" and "mixed salt" as used herein are used interchangeably, and, in the case of a polymer conjugate (and corresponding compositions comprising a plurality of such polymer conjugates), refer to a conjugates and compositions comprising one or more basic amino (or other basic nitrogen containing) groups, where (i) any given one of the basic amino groups in the conjugate or conjugate composition is either non-protonated or protonated and (ii) with respect to any given protonated basic amino group, the protonated basic amino group will have one of two different counterions. (The term "partial mixed salt" refers to the feature where not all amino groups in the compound or composition are protonated—hence the composition being a "partial" salt, while "mixed" refers to the feature of multiple counterions). A mixed salt as provided herein encompasses hydrates, solvates, amorphous forms, crystalline forms, polymorphs, isomers, and the like.

An amine (or other basic nitrogen) group that is in "free base" form is one where the amine group, i.e., a primary, secondary, or tertiary amine, possesses a free electron pair. The amine is neutral, i.e., is uncharged.

An amine group that is in "protonated form" exists as a protonated amine, so that the amino group is positively charged. As used herein, an amine group that is protonated can also be in the form of an acid addition salt resulting from reaction of the amine with an acid such as an inorganic acid or an organic acid.

The "mole percent" of an active agent's amino groups refers to the fraction or percentage of amino groups in an active agent molecule contained in a polymer conjugate that are in one particular form or another, where the total mole percent of amino groups in the conjugate is 100 percent.

As used herein, "psi" means pounds per square inch.

Overview: Mixed Salts Conjugates. Alkoxylation Methods, and Compositions of Conjugates (and Mixed Salt Forms Thereof) Prepared from Polymer Reagents Prepared from Polymeric Products Using the Alkoxylation Methods Mixed Salts: As previously indicated, in one or more aspects of the invention, a water-soluble polymer and active agent conjugate is provided, wherein the conjugate is in the form of a mixed salt. Such conjugates represent novel solid state forms and are based at least in part on the discovery that, in spite of treatment with base in their formation, conjugates precipitate as mixed salts. Moreover, it has been discovered that conjugates can reliably and reproducibly be produced as a mixed salts—where any given basic nitrogen atom within the conjugate (and within the active agent component of the conjugate) is present in one of a variety of forms. Specifically, the conjugates provided herein possess active agent basic nitrogen atoms, e.g., amino groups, each one of which will either be protonated or unprotonated, where any given protonated amino group is an acid salt possessing one of two different anions. Moreover, it has been discovered that the mixed salt form of the conjugate has several unexpected and advantageous characteristics (i.e., greater stability against degradation of the polymer backbone, greater hydrolytic stability, etc.) when compared to the corresponding free base or single acid salt forms of the conjugate.

Alkoxylation Methods: As also previously indicated, in one or more aspects of the invention, a method is provided, the method comprising the step of alkoxylating in a suitable solvent a previously isolated alkoxylatable oligomer to form an alkoxylated polymeric product, wherein the previously isolated alkoxylatable oligomer has a known and defined weight-average molecular weight of greater than 300 Daltons (e.g., greater than 500 Daltons). Among other advantages, the alkoxylation methods provided herein result in polymeric products that are superior (e.g., in terms of consistency and purity) than polymeric products prepared by previously known methods. In one or more embodiments, a polymer formed by the present alkoxylation methods may advantageously be used to prepare a mixed acid salt as described herein.

Compositions of Conjugates (and Mixed Salt Forms Thereof) Prepared from Polymer Reagents Prepared from Polymeric Products Using the Alkoxylation Methods: As also previously indicated, in one or more embodiments of the invention, a mixed salt of a water-soluble polymer-active agent conjugate is provided, wherein the conjugate is prepared by coupling (under conjugation conditions) an amine-bearing active agent (e.g., a deprotected glycine-irinotecan) to a polymer reagent (e.g., 4-arm pentaerythritolyl-poly(ethylene glycol)-carboxymethyl succinimide) in the presence of a base to form a conjugate, wherein the conjugate is a mixed salt conjugate (e.g., the conjugate possesses nitrogen atoms, each one of which will either be protonated or unprotonated, where any given protonated amino group is an acid salt possessing one of two different anions), and further wherein, optionally, the polymer reagent is prepared from a alkoxylation product prepared as described herein.

Conjugates—the Polymer Generally

Water-soluble polymer-active agent conjugates (regardless of the specific form taken, e.g., a base form, salt form, mixed salt, and so forth) include a water-soluble polymer. Typically, in order to form a conjugate, a water-soluble polymer—in the form of a polymer reagent—coupled (under conjugation conditions) to an active agent at an electrophile or nucleophile contained within the active agent. For example, a water-soluble polymer (again, in the form of a polymer reagent bearing, e.g., an activated ester) can be coupled to an active agent possessing one or more basic amine groups (or other basic nitrogen atoms), i.e. an amine having a pK from about 7.5 to about 11.5 (determined after conjugation).

The water-soluble polymer component of the conjugate is typically a water-soluble and non-peptidic polymer. Representative polymers include poly(alkylene glycol), poly(olefinic alcohol), poly(vinylpyrrolidone), poly(hydroxyalkylmethacrylamide), poly(hydroxyalkylmethacrylate), poly(saccharide), poly(α-hydroxy acid), poly(acrylic acid), poly(vinyl alcohol), polyphosphazene, polyoxazoline, poly(N-acryloylmorpholine), or copolymers or terpolymers thereof. One particular water-soluble polymer is polyethylene glycol or PEG comprising the repeat unit $(CH_2CH_2O)_n$—, where n ranges from about 3 to about 2700 or even greater, or preferably from about 25 to about 1300. Typically, the weight average molecular weight of the water-soluble polymer in the partial mixed acid salt ranges from about 100 daltons to about 150,000 daltons. Illustrative overall molecular weights for the conjugate may range from about 800 to about 80,000 daltons, or from about 900 to about 70,000 daltons. Additional representative molecular weight ranges are from about 1,000 to about 40,000 daltons, or from about 5,000 to about 30,000 daltons, or from about 7500 to about 25,000 daltons, or even from about 20,000 to about 80,000 daltons for higher molecular weight embodiments of the instant partial mixed salts.

The water-soluble polymer can be in any of a number of geometries or forms, including linear, branched, forked. In exemplary embodiments, the polymer is often linear or multi-armed. Water-soluble polymers can be obtained commercially as simply the water-soluble polymer. In addition, water-soluble polymers can be conveniently obtained in an activated form as a polymer reagent (which optionally may be coupled to an active agent without further modification or activation). Descriptions of water-soluble polymers and polymer reagents can be found in Nektar Advanced PEGylation Catalog, 2005-2006. "Polyethylene Glycol and Derivatives for Advanced PEGylation" and are available for purchase from NOF Corporation and JenKem Technology USA, among others.

An exemplary branched polymer having two polymer arms in a branched pattern is the following, often referred to as PEG-2 or mPEG-2:

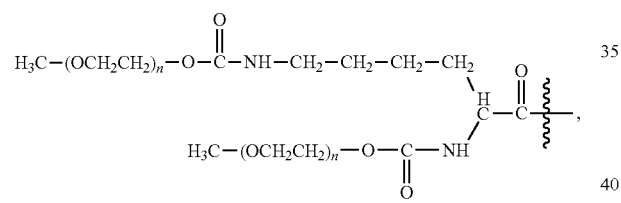

wherein ⁂ indicates the location for additional atoms to form any of functional groups suitable for reaction with an electrophile or nucleophile contained within an active agent. Exemplary functional groups include NHS ester, aldehyde, and so forth.

For polymer structures described herein that contain the variable, "n," such variable corresponds to an integer and represents the number of monomer subunits within the repeating monomeric structure of the polymer.

On exemplary architecture for use in preparing the conjugates are multi-arm water-soluble polymer reagents having for example 3, 4, 5, 6 or 8 polymer arms, each optimally bearing a functional group. A multi-arm polymer reagent may possess any of a number of cores (e.g., a polyol core) from which the polymer arms emanate. Exemplary polyol cores include glycerol, glycerol dimer (3,3'-oxydipropane-1,2-diol) trimethylolpropane, sugars (such as sorbitol or pentaerythritol, pentaerythritol dimer), and glycerol oligomers, such as hexaglycerol or 3-(2-hydroxy-3-(2-hydroxyethoxy) propoxy)propane-1,2-diol, and other glycerol condensation products. Exemplary, the cores and the polymer arms emanating therefrom can be of the following formulae:

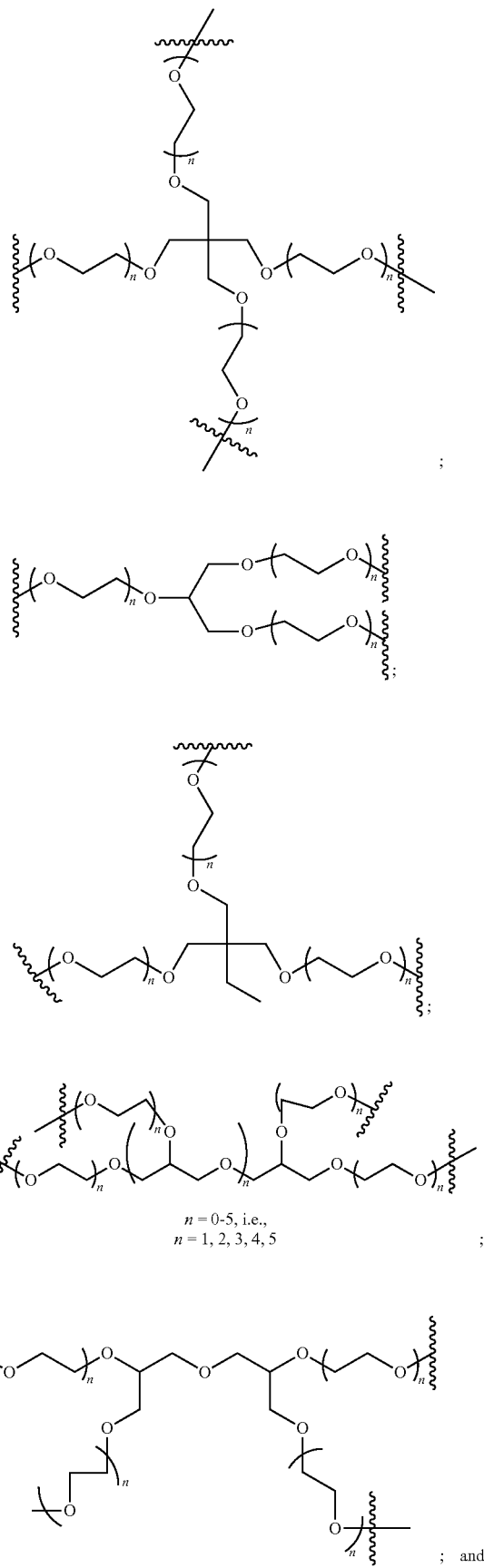

-continued

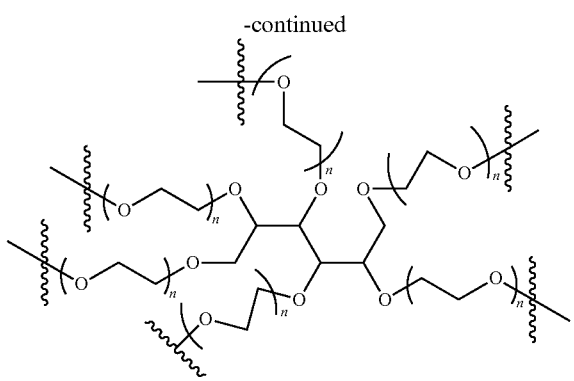

In an exemplified embodiment, the water soluble polymer is a 4-arm polymer as shown above, where n may range from about 20 to about 500, or from about 40 to about 500.

In the multi-arm embodiments described herein, each polymer arm typically has a molecular weight corresponding to one of the following: 200, 250, 300, 400, 500, 600, 700, 800, 900, 1000, 1500, 2000, 3000, 4000, 5000, 6000, 7000, 7500, 8000, 9000, 10000, 12,000, 15000, 17,500, 18,000, 19,000, 20,000 Daltons or greater. Overall molecular weights for the multi-armed polymer configurations described herein (that is to say, the molecular weight of the multi-armed polymer as a whole) generally correspond to one of the following: 800, 1000, 1200, 1600, 2000, 2400, 2800, 3200, 3600, 4000, 5000, 6000, 8000, 10,000, 12,000, 15,000, 16,000, 20,000, 24,000, 25,000, 28,000, 30,000, 32,000, 36,000, 40,000, 45,000, 48,000, 50,000, 60,000, 80,000 or 100,000 or greater.

The water-soluble polymer, e.g., PEG, may be covalently linked to the active agent via an intervening linker. The linker may contain any number of atoms. Generally speaking, the linker has an atom length satisfying one or more of the following ranges: from about 1 atom to about 50 atoms; from about 1 atom to about 25 atoms; from about 3 atoms to about 12 atoms; from about 6 atoms to about 12 atoms; and from about 8 atoms to about 12 atoms. When considering atom chain length, only atoms contributing to the overall distance are considered. For example, a linker having the structure, —$CH_2$—$C(O)$—$NH$—$CH_2CH_2O$—$CH_2CH_2O$—$C(O)$—$O$— is considered to have a chain length of 11 atoms, since substituents are not considered to contribute significantly to the length of the linker. Illustrative linkers include bifunctional compounds such as amino acids (e.g. alanine, glycine, isoleucine, leucine, phenylalanine, methionine, serine, cysteine, sarcosine, valine, lysine, and the like). The amino acid may be a naturally-occurring amino acid or a non-naturally occurring amino acid. Suitable linkers also include oligopeptides.

The multi-arm structures above are drawn primarily to illustrate the polymer core having PEG chains attached thereto, and although not drawn explicitly, depending upon the nature of the active agent and attachment chemistry employed, the final structure may optionally include an additional ethylene group, —$CH_2CH_2$—, attached to the oxygen atoms at the terminus of each polymer arm, and/or may optionally contain any of a number of intervening linker atoms to facilitate covalent attachment to an active agent. In a particular embodiment, each of the PEG arms illustrated above further comprises a carboxy methyl group, —$CH_2$—$C(O)O$—, covalently attached to the terminal oxygen atom.

New Alkoxylation Method for Improved Polymer Compositions

As indicated previously, water-soluble polymers that have utility in (for example) preparing conjugates with active agents (as well as salt and mixed salt forms thereof) can be obtained commercially. As further described herein, however, methods for preparing water-soluble polymers—which methods distinguish over previously described methods for preparing water-soluble polymers—are provided that are particularly suited for preparing conjugates with active agents (as well as salt and mixed salt forms thereof).

In this regard, a method is provided, the method comprising the step of alkoxylating in a suitable solvent a previously isolated alkoxylatable oligomer to form an alkoxylated polymeric product, wherein the previously isolated alkoxylatable oligomer has a known and defined weight-average molecular weight of greater than 300 Daltons (e.g., greater than 500 Daltons).

The Alkoxylating Step in the New Alkoxylation Method

The alkoxylating step is carried out using alkoxylation conditions, such that the sequential addition of monomers is effected through repeated reactions of an oxirane compound. When the alkoxylatable oligomer initially has one or more hydroxyl functional groups, one or more of these hydroxyl groups in the alkoxylatable oligomer will be converted into a reactive alkoxide by reaction with a strong base. Then, an oxirane compound reacts with an alkoxylatable functional group (e.g., a reactive alkoxide), thereby not only adding to the reactive alkoxide, but doing so in a way that also terminates in another reactive alkoxide. Thereafter, repeated reactions of an oxirane compound at the reactive alkoxide terminus of the previously added and reacted oxirane compound effectively produces a polymer chain.

Although each of the one or more alkoxylatable functional groups is preferably hydroxyl, other groups such as amines, thiols and the hydroxyl group of a carboxylic acid can serve as an acceptable alkoxylatable functional group. Also, because of the acidity of the hydrogens of the alpha carbon atoms in aldehydes, ketones, nitriles and amides, addition at the alpha carbon atoms of these groups can serve as an acceptable alkoxylatable functional group.

The oxirane compound contains an oxirane group and has the following formula:

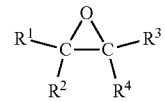

wherein (with respect to this structure):
$R^1$ is selected from the group consisting of H and alkyl (preferably lower alkyl when alkyl);
$R^2$ is selected from the group consisting of H and alkyl (preferably lower alkyl when alkyl);
$R^3$ is selected from the group consisting of H and alkyl (preferably lower alkyl when alkyl); and
$R^4$ is selected from the group consisting of H and alkyl (preferably lower alkyl when alkyl).

With respect to the above oxirane compound formula, it is particularly preferred that each of $R^1$, $R^2$, $R^3$ and $R^4$ is H, and it is preferred that only one of $R^1$, $R^2$, $R^3$ and $R^4$ is alkyl (e.g., methyl and ethyl) and the remaining substituents are H. Exemplary oxirane compounds are ethylene oxide, propylene oxide and 1,2-butylene oxide. The amount of oxirane compound added to result in optimal alkoxylation conditions depends upon a number of factors, including the amount of starting alkoxylatable oligomer, the desired size of the resulting alkoxylated polymeric material and the number of alkoxylatable functional groups on the alkoxylatable oligomer. Thus, when a larger alkoxylated polymeric material is desired, relatively more oxirane compound is present in the alkoxylation conditions. Similarly, if (Oa) represents the amount of oxirane compound needed to achieve a given size of polymer "growth" on a single alkoxylatable functional group, then an alkoxylatable oligomer bearing two alkoxylatable functional groups requires 2×(Oa), an alkoxylatable oligomer bearing three alkoxylatable functional groups requires 3×(Oa), an alkoxylatable oligomer bearing four alkoxylatable functional groups requires 4×(Oa) and so on. In all cases, one of ordinary skill in the art can determine an appropriate amount of oxirane compound required for alkoxylation conditions by taking into account the desired molecular weight of alkoxylated polymeric material and following routine experimentation.

The alkoxylation conditions include the presence of a strong base. The purpose of the strong base is to deprotonate each acidic hydrogen (e.g., the hydrogen of a hydroxyl group) present in the alkoxylatable oligomer and form an alkoxide ionic species (or an ionic species for non-hydroxyl alkoxylatable functional groups). Preferred strong bases for use as part of the alkoxylation conditions are: alkali metals, such as metallic potassium, metallic sodium, and alkali metals mixtures such as sodium-potassium alloys; hydroxides, such as NaOH and KOH; and alkoxides (e.g. present following addition of an oxirane compound). Other strong bases can be used and can be identified by one of ordinary skill in the art. For example a given base can be used as a strong base herein if the strong base can form an alkoxide ionic species (or an ionic species for non-hydroxyl alkoxylatable functional groups) and also provide a cation that does not encumber the alkoxide ionic species so as to hinder (or effectively hinder through an impractically slow) reaction of the alkoxide ionic species with the oxirane molecule. The strong base is present in a generally small and calculated amount, which amount can fall into one or more of the following ranges; from 0.001 to 10.0 weight percent based upon the weight of the total reaction mixture; and from 0.01 to about 6.0 weight percent based upon the weight of the total reaction mixture.

The alkoxylation conditions include a temperature suitable for alkoxylation to occur. Exemplary temperatures that may be suitable for alkoxylation to occur include those falling into one or more of the following ranges: from 10° C. to 260° C.; from 20° C. to 240° C.; from 30° C. to 220° C.; from 40° C. to 200° C.; from 50° C. to 200° C.; from 80° C. to 140° C.; and from 100° C. to 120° C.

The alkoxylation conditions include a pressure suitable for alkoxylation to occur. Exemplary pressures that may be suitable for alkoxylation to occur include those falling into one or more of the following ranges: from 10 psi to 1000 psi; from 15 psi to 500 psi; from 20 psi to 250 psi; from 25 psi to 100 psi. In addition, the alkoxylation pressure can be about atmospheric pressure at sea level (e.g., 14.696 pounds per square inch +/−10%).

In some instances, the alkoxylation conditions include addition of the oxirane compound in liquid form. In some instances, the alkoxylation conditions include addition of the oxirane compound in vapor form.

The alkoxylation conditions can include the use of a suitable solvent. Optimally, the system in which the alkoxylation conditions occur will not include any component (including any solvent) that can be deprotonated (or remains substantially protonated under the conditions of pH, temperature, and so forth under which the alkoxylation conditions will occur). Suitable solvents for alkoxylation include organic solvents selected from the group consisting of, tetrahydrofuran (THF), dimethylformamide (DMF), toluene, benzene, xylenes, mesitylene, tetrachloroethylene, anisole, dimethylacetamide, and mixtures of the foregoing. Less ideal solvents (but nonetheless still contemplated) for use as part of the alkoxylation conditions are acetonitrile, phenylacetonitrile and ethyl acetate: in some instances, the alkoxylation conditions will not include as a solvent any of acetonitrile, phenylacetonitrile and ethyl acetate.

In one or more embodiments of the invention, when the alkoxylation conditions are conducted in the liquid phase, the alkoxylation conditions are conducted such that both the alkoxylatable oligomer and the desired alkoxylated polymeric material formed from alkoxylating the alkoxylatable oligomer not only have similar solubilities (and, preferably, substantially the same solubility) in the suitable solvent used, but are also both substantially soluble in the suitable solvent. For example, in one or more embodiments, the alkoxylatable oligomer will be substantially soluble in the solvent used in the alkoxylation conditions and the resulting alkoxylated polymeric material also will be substantially soluble in the alkoxylation conditions.

In one or more embodiments, this substantially same solubility of the alkoxylated oligomer and the alkoxylated polymeric material in a suitable solvent stands in contrast to the solubility of a precursor molecule (used, for example, in the preparation of the previously isolated alkoxylated oligomer) in the suitable solvent, wherein the precursor molecule can have a lower (and even substantially lower) solubility in the suitable solvent than the alkoxylated oligomer and/or the alkoxylated polymeric material. By way of example only, the alkoxylated oligomer and the alkoxylated polymeric material will both have a pentaerthritol core and will both be substantially soluble in toluene, but pentaerthritol itself has limited solubility in toluene.

It is particularly preferred that the solvent employed in the alkoxylation conditions is toluene. The amount of toluene used for the reaction is greater than 25 wt % and less than 75 wt % of the reaction mixture, based on the weight of reaction mixture after complete addition of the oxirane compound. One of ordinary skill in the art can calculate the starting amount of the solvent by taking into account the desired molecular weight of the polymer, the number of sites for which alkoxylation will take place, the weight of the alkoxylatable oligomer used, and so forth.

It is preferred that the amount of the toluene is measured so that the amount is sufficient for the alkoxylation conditions providing the desired alkoxylated polymeric material.

In addition, it is particularly preferred that the alkoxylation conditions have substantially no water present. Thus, it is preferred that the alkoxylation conditions have a water content of less than 100 ppm, more preferably 50 ppm, still more preferably 20 ppm, much more preferably less than 14 ppm, and even still more preferably less than 8 ppm.

The alkoxylation conditions take place in a suitable reaction vessel, typically a stainless steel reactor vessel.

In one or more embodiments, the alkoxylatable oligomer and/or precursor molecule lacks an isocyanate group attached to a carbon bearing an alpha hydrogen is acceptable. In one or more embodiments, the previously prepared alkoxylatable oligomer and/or precursor molecule lacks an isocyanate group.

The Alkoxylatable Oligomer in the New Alkoxylation Method

The alkoxylatable oligomer used in the new alkoxylation method must have at least one alkoxylatable functional group. The alkoxylatable oligomer, however, can have one, two, three, four, five, six, seven, eight or more alkoxylatable functional groups, with a preference for an alkoxylatable oligomer having from one to six alkoxylatable functional groups.

As stated previously, each alkoxylatable functional group within the alkoxylatable oligomer can be independently selected from the group consisting of hydroxyl, carboxylic acid, amine, thiol, aldehyde, ketone, and nitrile. In those instances where there is more than one alkoxylatable functional group within the alkoxylatable oligomer, it is typical that each alkoxylatable functional group is the same (e.g., each alkoxylatable functional group within the alkoxylatable oligomer is hydroxyl), although instances of different alkoxylatable functional groups within the same alkoxylatable oligomer are contemplated as well. When the alkoxylatable functional group is hydroxyl, it is preferred that the hydroxyl is a primary hydroxyl.

The alkoxylatable oligomer can take any of a number of possible geometries. For example, the alkoxylatable oligomer can be linear. In one example of a linear alkoxylatable oligomer, one terminus of the linear alkoxylatable oligomer is a relatively inert functional group (e.g., an end-capping group) and the other terminus is an alkoxylatable functional group (e.g., hydroxyl). An exemplary alkoxylatable oligomer of this structure is methoxy-PEG-OH, or mPEG in brief, in which one terminus is the relatively inert methoxy group, while the other terminus is a hydroxyl group. The structure of mPEG is given below.

$$CH_3O—CH_2CH_2O—(CH_2Cl_2O)_n—CH_2CH_2—OH$$

(wherein, for the immediately preceding structure only, n is an integer from 13 to 100).

Another example of a linear geometry for which the alkoxylatable oligomer can take is a linear organic polymer bearing alkoxylatable functional groups (either the same or different) at each terminus. An exemplary alkoxylatable oligomer of this structure is alpha-, omega-dihydroxylpoly(ethylene glycol), or $$HO—CH_2CH_2O—(CH_2CH_2O)_n—CH_2CH_2—OH$$

(wherein, for the immediately preceding structure only, n is an integer from 13 to 100), which can be represented in brief form as HO-PEG-OH where it is understood that the —PEG-symbol represents the following structural unit:

$$—CH_2CH_2O—(CH_2CH_2O)_n—CH_2CH_2—$$

(wherein, for the immediately preceding structure only, n is an integer from 13 to 100), Another geometry for which the alkoxylatable oligomer may have is a "multi-armed" or branched structure. With respect to such branched structures, one or more atoms in the alkoxylatable oligomer serves as a "branching point atom," through which two, three, four or more (but typically two, three or four) distinct sets of repeating monomers or "arms" are connected (either directly or through one or more atoms). At a minimum, a "multi-arm" structure as used herein has three or more distinct arms, but can have as many as four, five, six, seven, eight, nine, or more arms, with 4- to 8-arm multi-arm structures preferred (such as a 4-arm structure, a 5-arm structure, a 6-arm structure, and an 8-arm structure).

Exemplary multi-arm structures for the alkoxylatable oligomer are provided below:

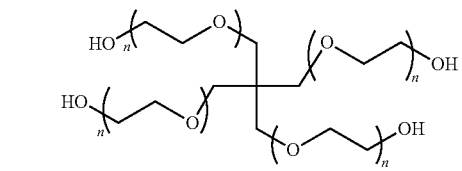

wherein (for the immediately preceding structure only) the average value of n is from 1 to 50, e.g., from 10 to 50, (or otherwise defined such that the molecular weight of the structure is from 300 Daltons to 9,000 Daltons (e.g., from about 500 Daltons to 5,000 Daltons);

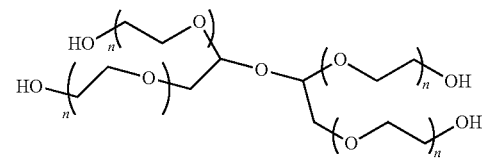

wherein (for the immediately preceding structure only) the average value of n is from 2 to 50, e.g., from 10 to 50 (or otherwise defined such that the molecular weight of the structure is from 300 Daltons to 9,000 Daltons (e.g., from about 500 Daltons to 5,000 Daltons);

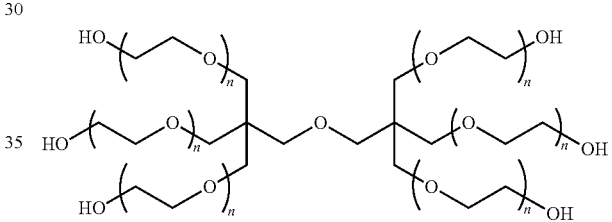

wherein (for the immediately preceding structure only) the average value of n is from 2 to 35, e.g., from 8 to about 40 (or otherwise defined such that the molecular weight of the structure is from 750 Daltons to 9,500 Daltons (e.g., from 500 Daltons to 5,000 Daltons); and

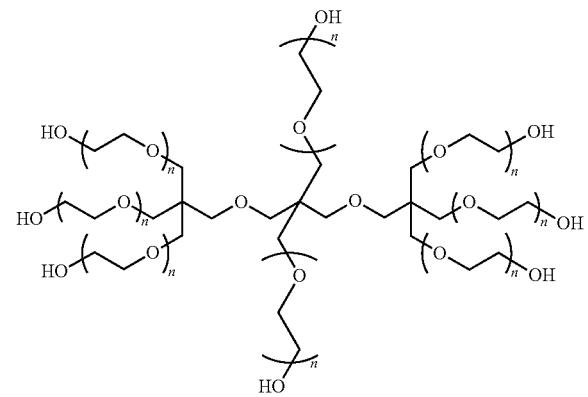

wherein (for the immediately preceding structure only) the average value of n is 2 to 35, e.g., from 5 to 35, (or otherwise defined such that the molecular weight of the structure is from 1,000 Daltons to 13,000 Daltons (e.g., from 500 Daltons to 5,000 Daltons).

For each of the four immediately preceding structures, it is preferred that the value of n, in each instance, is substantially the same. Thus, it is preferred that when all values of n are considered for a given alkoxylatable oligomer, all values of n for that alkoxylatable oligomer are within three standard deviations, more preferably within two standard deviations, and still more preferably within one standard deviation.

In terms of the molecular weight of the alkoxylatable oligomer, the alkoxylatable oligomer will have a known and defined weight-average molecular weight. For use herein, a weight-average molecular weight can only be known and defined for an alkoxylatable oligomer when the alkoxylatable oligomer is isolated from the synthetic milieu from which it was generated. Exemplary weight-average molecular weights for the alkoxylatable oligomer will fall into one or more of the following ranges: greater than 300 Daltons; greater than 500 Daltons; from 300 Daltons to 15,000 Daltons; from 500 Daltons to 5,000 Daltons; from 300 Daltons to 10,000 Daltons; from 500 Daltons to 4,000 Daltons; from 300 Daltons to 5,000 Daltons; from 500 Daltons to 3,000 Daltons; from 300 Daltons to 2,000 Daltons; from 500 Daltons to 2,000 Daltons; from 300 Daltons to 1,000 Daltons; from 500 Daltons to 1,000 Daltons; from 1,000 Daltons to 10,000 Daltons; from 1,000 Daltons to 5,000 Daltons; from 1,000 Daltons to 4,000 Daltons; from 1,000 Daltons to 3,000 Daltons; from 1,000 Daltons to 2,000 Daltons; from 1,500 Daltons to 15,000 Daltons; from 1,500 Daltons to 5,000 Daltons; from 1,500 Daltons to 10,000 Daltons; from 1,500 Daltons to 4,000 Daltons; from 1,500 Daltons to 3,000 Daltons; from 1,500 Daltons to 2,000 Daltons; from 2,000 Daltons to 5,000 Daltons: from 2,000 Daltons to 4,000 Daltons; and from 2,000 Daltons to 3,000 Daltons.

For purposes of the present invention, the alkoxylatable oligomer is preferably previously isolated. By previously isolated is meant the alkoxylatable oligomer exists outside and separate from the synthetic milieu from which it was generated (most typically outside of the alkoxylating conditions used to prepare the alkoxylatable oligomer) and can optionally be stored for a relatively long period of time or optionally stored over a shorter time without substantially changing for subsequent use. Thus, an alkoxylatable oligomer is previously isolated if, for example, it is housed in an inert environment. In this regard, a previously isolated alkoxylated oligomer can be housed in a container substantially lacking (e.g., less than 0.1 wt %) an oxirane compound. Also, a previously isolated alkoxylatable oligomer does not change its molecular weight more than 10% over the course of 15 days. Thus, in one or more embodiments of the invention, the concept of "previously isolated" stands in contrast to (for example) a situation where an ongoing and uninterrupted alkoxylation reaction is allowed to proceed from precursor molecule, into a structure that corresponds an alkoxylatable oligomer, to a structure that corresponds to an alkoxylated polymeric material; the concept of "previously isolated" requires that the alkoxylatable oligomer exists apart from the conditions from which it formed. Pursuant to the present invention, however, the previously isolated alkoxylatable oligomer will be subjected to an alkoxylation step once it is added to, as a separate step, alkoxylation conditions.

Sources of the Alkoxylatable Oligomer in the New Alkoxylation Method

The alkoxylatable oligomer can be obtained via synthetic means. In this regard, the alkoxylatable oligomer is prepared by (a) alkoxylating a precursor molecule having a molecular weight of less than 300 Daltons (e.g. less than 500 Daltons) to form a reaction mixture comprising an alkoxylatable oligomer or prepolymer, and (b) isolating the alkoxylatable oligomer from the reaction mixture. The step of alkoxylating the precursor molecule largely follows the conditions and requirements of the alkoxylating step previously discussed. The step of isolating the alkoxylatable oligomer can be carried out using any art known step, but can include allowing all oxirane compound to be consumed in the reaction, actively performing a quenching step, separating the final reaction mixture through art-known approaches (including, for example, distilling off all volatile materials, removing solid reaction by-product by filtration or washing and applying chromatographic means).

In addition, the alkoxylatable oligomer can be obtained from commercial sources. Exemplary commercial sources include NOF Corporation (Tokyo Japan) which provides alkoxylatable oligomers under the names SUNBRIGHT DKH® poly(ethylene glycol), SUNBRIGHT® GL glycerine, tri-poly(ethylene glycol) ether, SUNBRIGHT PTE® pentaerythritol, tetra-poly(ethylene glycol) ether, SUNBRIGHT® DG di-glycerine, tetra-poly(ethylene glycol) ether, and SUNBRIGHT HGEO® hexa-glycerine, octa-poly (ethylene glycol) ether. Preferred alkoxylatable oligomers include those having the structures of SUNBRIGHT PTE®-2000 pentaerythritol, tetra-poly(ethylene glycol) ether (which has a weight-average molecular weight of about 2,000 Daltons) and SUNBRIGHT® DG-2000 di-glycerine, tetra-poly(ethylene glycol) ether (which has a weight-average molecular weight of about 2,000 Daltons).

Precursor molecules can be any small molecule (e.g., a molecular weight less than the weight-average molecular weight of the alkoxylatable oligomer) having one or more alkoxylatable functional groups.

Exemplary precursor molecules include polyols, which are small molecules (typically of a molecular weight of less than 300 Daltons, e.g., less than 500 Daltons) having a plurality of available hydroxyl groups. Depending on the desired number of polymer arms in the alkoxylatable oligomer or prepolymer, the polyol serving as the precursor molecule will typically comprise 3 to about 25 hydroxyl groups, preferably about 3 to about 22 hydroxyl groups, most preferably about 4 to about 12 hydroxyl groups. Preferred polyols include glycerol oligomers or polymers such as hexaglycerol, pentaerythritol and oligomers or polymers thereof (e.g., dipentaerythritol, tripentaerythritol, tetrapentaerythritol, and ethoxylated forms of pentaerythritol), and sugar-derived alcohols such as sorbitol, arabanitol, and mannitol. Also, many commercially available polyols, such as various isomers of inositol (i.e. 1,2,3,4,5,6-hexahydroxycyclohexane), 2,2-bis(hydroxymethyl)-1-butanol, (2-amino-2-(hydroxymethyl)-1,3-propanediol (TRIS). 2-[bis(2-hydroxyethyl)amino]-2-(hydroxymethyl)-1,3-propanediol. {[2-hydroxy-1,1-bis(hydroxymethyl)ethyl]amino}acetic acid (Tricine), 2-[(3-{[2-hydroxy-1,1-bis(hydroxymethyl)ethyl]amino}propyl)amino]-2-(hydroxymethyl)-1,3-propanediol, 2-{[2-hydroxy-1,1-bis(hydroxymethyl)ethyl]amino}ethanesulfonic acid (TES), 4-{[2-hydroxy-1,1-bis(hydroxymethyl)ethyl]amino}-1-butanesulfonic acid, and 2-[bis(2-hydroxyethyl)amino]-2-(hydroxymethyl)-1,3-propanediol hydrochloride can serve as an acceptable precursor molecule. In those cases in which the precursor molecule has an ionizable group or groups that will interfere with the alkoxylation step, those ionizable groups must be protected or modified prior to carrying out the alkoxylation step.

Exemplary preferred precursor molecules include those precursor molecules selected from the group consisting of glycerol, diglycerol, triglycerol, hexaglycerol, mannitol, sorbitol, pentaerythritol, dipentaerthitol, and tripentaerythritol.

In one or more embodiments of the invention, it is preferred that neither the previously isolated alkoxylatable oligomer nor the alkoxylated polymeric product has an alkoxylatable functional group (e.g. hydroxyl group) of the precursor molecule.

The Alkoxylated Polymeric Materials Generated by the New Alkoxylation Method

The alkoxylated polymeric material prepared under the methods described herein will have a basic architecture corresponding to the structure of the alkoxylatable oligomer (i.e., a linear alkoxylatable oligomer results in a linear alkoxylated polymericmaterial, a four-armed alkoxylatable oligomer results in a four-armed alkoxylated polymer material, so forth). As a consequence, the alkoxylated polymeric material will take any of a number of possible geometries, including linear, branched and multi-armed.

With respect to branched structures, a branched alkoxylated polymeric material will have three or more distinct arms, but can have as many as four, five, six, seven, eight, nine, or more arms, with 4- to 8-arm branched structures preferred (such as a 4-arm branched structure, 5-arm branched structure, 6-arm branched structure, and 8-arm branched structure).

Exemplary branched structures for the alkoxylated polymeric material are provided below:

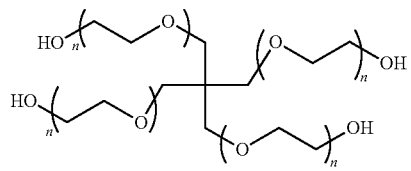

wherein (for the immediately preceding structure only) the average value of n satisfies one or more of the following ranges: from 10 to 1,000; from 10 to 500: from 10 to 250; from 50 to 1000; from 50 to 250; and from 50 to 120 (or otherwise defined such that the molecular weight of the structure is from 2,000 Daltons to 180,000 Daltons, e.g., from 2,000 Daltons to 120,000 Daltons)

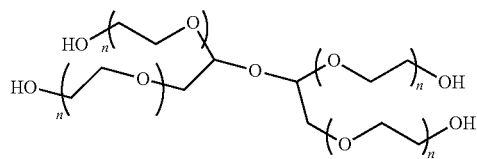

wherein (for the immediately preceding structure only) the average value of n satisfies one or more of the following ranges: from 10 to 1,000; from 10 to 500; from 10 to 250; from 50 to 1,000; from 50 to 250; and from 50 to 120 (or otherwise defined such that the molecular weight of the structure is from 2,000 Daltons to 180,000 Daltons, e.g., from 2,000 Daltons to 120,000 Daltons);

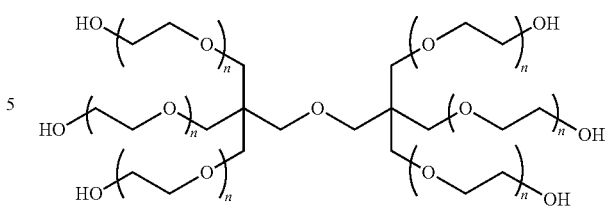

wherein (or the immediately preceding structure only) the average value of n is satisfies one or more of the following ranges: from 10 to 750; from 40 to 750; from 50 to 250; and from 50 to 120 (or otherwise defined such that the molecular weight of the structure is from 3,000 Daltons to 200,000 Daltons, e.g., from 12,000 Daltons to 200,000 Daltons); and

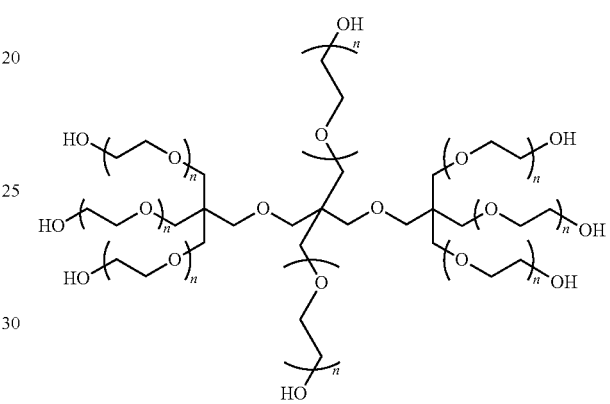

wherein (for the immediately preceding structure only) the average value of n is satisfies one or more of the following ranges: from 10 to 600 and from 35 to 600 (or otherwise defined such that the molecular weight of the structure is from 4,000 Daltons to 215,000 Daltons, e.g. from 12,000 Daltons to 215,000 Daltons).

For each of the four immediately provided structures, it is preferred that the value of n, in each instance, is substantially the same. Thus, it is preferred that when all values of n are considered for a given alkoxylated polymeric material, all values of n for that alkoxylated polymeric material alkoxylatable oligomer or prepolymer are within three standard deviations, more preferably within two standard deviations, and still more preferably within one standard deviation.

In terms of the molecular weight of the alkoxylated polymeric material, the alkoxylated polymeric material will have a known and defined number-average molecular weight. For use herein, a number-average molecular weight can only be known and defined for material that is isolated from the synthetic milieu from which it was generated.

The total molecular weight of the alkoxylated polymeric product can be a molecular weight suited for the intended purpose. An acceptable molecular weight for any given purpose can be determined through trial and error via routine experimentation. Exemplary molecular weights for the alkoxylated polymeric product, will have a number-average molecular weight falling within one or more of the following ranges: from 2,000 Daltons to 215,000 Daltons; from 5,000 Daltons to 215,000 Daltons; from 5,000 Daltons to 150,000 Daltons; from 5,000 Daltons to 100,000 Daltons; from 5,000 Daltons to 80,000 Daltons; from 6,000 Daltons to 80,000 Daltons; from 7,500 Daltons to 80,000 Daltons; from 9,000 Daltons to 80,000 Daltons; from 10,000 Daltons to 80,000

Daltons; from 12,000 Daltons to 80,000 Daltons; from 15,000 Daltons to 80,000 Daltons; from 20,000 Daltons to 80,000 Daltons; from 25,000 Daltons to 80,000 Daltons; from 30,000 Daltons to 80,000 Daltons; from 40,000 Daltons to 80,000 Daltons; from 6,000 Daltons to 60,000 Daltons; from 7,500 Daltons to 60,000 Daltons; from 9,000 Daltons to 60,000 Daltons; from 10,000 Daltons to 60,000 Daltons; from 12,000 Daltons to 60,000 Daltons; from 15,000 Daltons to 60,000 Daltons; from 20,000 Daltons to 60,000 Daltons; from 25,000 Daltons to 60,000 Daltons; from 30,000 Daltons to 60,000; from 6,000 Daltons to 40,000 Daltons; from 9,000 Daltons to 40,000 Daltons; from 10,000 Daltons to 40,000 Daltons; from 15,000 Daltons to 40,000 Daltons; from 19,000 Daltons to 40,000 Daltons; from 15,000 Daltons to 25,000 Daltons; and from 18,000 Daltons to 22,000 Daltons.

For any given alkoxylated polymeric material, an optional step can be carried out so as to further transform the alkoxylated polymeric material so that it bears a specific reactive group to form a polymeric reagent. Thus, using techniques well known in the art, the alkoxylated polymeric material can be functionalized to include a reactive group (e.g., carboxylic acid, active ester, amine, thiol, maleimide, aldehyde, ketone, and so forth).

In carrying out an optional step to further transform the alkoxylated polymeric product so that it bears a specific reactive group, such an optional step is carried out in a suitable solvent. One of ordinary skill in the art can determine whether any specific solvent is appropriate for any given reaction step. Often, however, the solvent is preferably a nonpolar solvent or a polar solvent. Nonlimiting examples of nonpolar solvents include benzene, xylenes and toluene. Exemplary polar solvents include, but are not limited to, dioxane, tetrahydrofuran (THF), f-butyl alcohol, DMSO (dimethyl sulfoxide), HMPA (hexamethylphosphoramide), DMF (dimethylformamide), DMA (dimethylacetamide), and NMP (N-methylpyrrolidinone).

Further Compositions of the Alkoxylated Polymeric Material

Another aspect of the invention provided herein are compositions comprising the alkoxylated polymeric material, which include not only any compositions comprising the alkoxylated polymeric material, but also compositions in which the alkoxylated polymeric material is further transformed into, for example, a polymer reagent, as well as compositions of conjugates formed from coupling such polymer reagents with an active agent. Among other things, a benefit of the method described herein is the ability to achieve high purity alkoxylated polymeric material-containing compositions. The compositions can be characterized as having: substantially low content of both high molecular weight impurities (e.g., polymer-containing species having a molecular weight greater than the molecular weight of the desired alkoxylated polymeric material) and low content of low molecular weight diol impurities (i.e., HO-PEG-OH), either impurity type (and preferably both impurity types) totaling less than 8 wt %, and more preferably less than 2 wt %. In addition or alternatively, the compositions can also be characterized as having a purity of alkoxylated polymeric material (as well as compositions comprising polymer reagents formed from the alkoxylated polymeric material, and compositions of conjugates formed from conjugating such polymer reagents and an active agent) of greater than 92 wt %, of greater than 93 wt %, or greater than 94 wt %, of greater than 95 wt %, preferably of greater than 96 wt %, and more preferably greater than 97 wt %. Gel permeation chromatography (GPC) and gel filtration chromatography (GFC) can be used to characterize the alkoxylated polymeric material. Those chromatographic methods allow separation of the composition to its components according to molecular weight. The exemplary GFC traces of products described in the Example 8 and Example 9 are provided as FIG. 7 and FIG. 8.

Exemplary Uses of the Alkoxylated Polymeric Materials and Compositions Formed Therefrom The alkoxylated polymeric material provided herein as well as those alkoxylated polymeric products that have been further modified to bear a specific reactive group (hereinafter referred to as a "polymer reagent") are useful for conjugation to, for example, active agents. Preferred groups of the biologically active agents suited for reaction with the polymeric reagents described herein are electrophilic and nucleophilic groups. Exemplary groups include primary amines, carboxylic acids, alcohols, thiols, hydrazines and hydrazides. Such groups suited to react with the polymeric reagents described herein are known to those of ordinary skill in the art. Thus, the invention provides a method for making a conjugate comprising the step of contacting, under conjugation conditions, an active agent with a polymeric reagent described herein.

Suitable conjugation conditions are those conditions of time, temperature, pH, reagent concentration, reagent functional group(s), available functional groups on the active agent, solvent, and the like sufficient to effect conjugation between a polymeric reagent and an active agent. As is known in the art, the specific conditions depend upon, among other things, the active agent, the type of conjugation desired, the presence of other materials in the reaction mixture, and so forth. Sufficient conditions for effecting conjugation in any particular case can be determined by one of ordinary skill in the art upon a reading of the disclosure herein, reference to the relevant literature, and/or through routine experimentation.

For example, when the polymeric reagent contains an N-hydroxysuccinimide active ester (e.g., succinimidyl succinate, succinimidyl propionate, and succinimidyl butanoate), and the active agent contains an amine group, conjugation can be effected at a pH of from about 7.5 to about 9.5 at room temperature. In addition, when the polymer reagent contains a vinylsulfone reactive group or a maleimide group and the pharmacologically active agent contains a sulfhydryl group, conjugation can be effected at a pH of from about 7 to about 8.5 at room temperature. Moreover, when the reactive group associated with the polymer reagent is an aldehyde or ketone and the pharmacologically active agent contains a primary amine, conjugation can be effected by reductive amination wherein the primary amine of the pharmacologically active agent reacts with the aldehyde or ketone of the polymer. Taking place at pH's of from about 6 to about 9.5, reductive amination initially results in a conjugate wherein the pharmacologically active agent and polymer are linked via an imine bond. Subsequent treatment of the imine bond-containing conjugate with a suitable reducing agent such as $NaCNBH_3$ reduces the imine to a secondary amine. For additional information concerning these and other conjugation reactions, reference is made to Hermanson "Bioconjugate Techniques." Academic Press, 1996.

Exemplary conjugation conditions include carrying out the conjugation reaction at a pH of from about 4 to about 10, and at, for example, a pH of about 4.0, 4.5, 5.0, 5.5, 6.0, 6.5, 7.0, 7.5, 8.0, 8.5, 9.0, 9.5, or 10.0. The reaction is allowed to proceed from about 5 minutes to about 72 hours, preferably from about 30 minutes to about 48 hours, and more preferably from about 4 hours to about 24 hours. The temperature under which conjugation can take place is typically, although not necessarily, in the range of from about 0° C. to about 40° C., and is often at room temperature or less. The conjugation reactions are often carried out using a phosphate buffer solution, sodium acetate, or similar system.

With respect to reagent concentration, an excess of the polymer reagent is typically combined with the active agent. In some cases, however, it is preferred to have stoichiometric amounts of reactive groups on the polymer reagent to the reactive groups of the active agent. Thus, for example, one mole of a polymer reagent bearing four reactive groups is combined with four moles of active agent. Exemplary ratios of reactive groups of polymer reagent to active agent include molar ratios of about 1:1 (reactive group of polymer reagent: active agent), 1:0.1, 1:0.5, 1:1.5, 1:2, 1:3, 1:4, 1:5, 1:6, 1:8, or 1:10. The conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by chromatographic methods, SDS-PAGE or MALDI-TOF mass spectrometry. NMR, IR, or any other suitable analytical method. Once a plateau is reached with respect to the amount of conjugate formed or the amount of unconjugated polymer reagent remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess active agent, strong base, condensing agents and reaction by-products and solvents. The resulting conjugates can then be further characterized using analytical methods such as chromatographic methods, spectroscopic methods, MALDI, capillary electrophoresis, and/or gel electrophoresis. The polymer-active agent conjugates can be purified to obtain/isolate different conjugated species.

With respect to an active agent, the alkoxylated polymeric material and a polymer reagent prepared from the alkoxylated polymeric material can be combined under suitable conjugation conditions to result in a conjugate. In this regard, exemplary active agents can be an active agent selected from the group consisting of a small molecule drug, an oligopeptide, a peptide, and a protein. The active agent for use herein can include but arm, not limited to the following: adriamycin. γ-aminobutyric acid (GABA), amiodarone, amitryptyline, azithromycin, benzphetamine, bromopheniramine, cabinoxamine, calcitonin chlorambucil, chloroprocaine, chloroquine, chlorpheniramine, chlorpromazine, cinnarizine, clarthromycin, clomiphene, cyclobenzaprine, cyclopentolate, cyclophosphamide, dacarbazine, daunomycin, demeclocycline, dibucaine, dicyclomine, diethylproprion, diltiazem, dimenhydrinate, diphenhydramine, disopyramide, doxepin, doxycycline, doxylamine, dypyridame, EDTA, erythromycin, flurazepam, gentian violet, hydroxychloroquine, imipramine, insulin, irinotecan, levomethadyl, lidocaine, loxarine, mechlorethamine, melphalan, methadone, methotimeperazine, methotrexate, metoclopramide, minocycline, naftifine, nicardipine, nizatidine, orphenadrine, oxybutin, oxytetracycline, phenoxybenzamine, phentolamine, procainamide, procaine, promazine, promethazine, proparacaine, propoxycaine, propoxyphene, ranitidine, tamoxifen, terbinafine, tetracaine, tetracycline, tranadol, trifluoromazine, trimeprazine, trimethylbenzamide, trimipramine, tripelennamine, troleandomycin, tyramine, uracil mustard, verapamil, and vasopressin.

Further exemplary active agents include those selected from the group consisting of acravistine, amoxapine, astemizole, atropine, azithromycin, benzapril, benztropine, beperiden, bupracaine, buprenorphine, buspirone, butorphanol, caffeine, camptothecin and molecules belonging to the camptothecin family, ceftriaxone, chlorpromazine, ciprofloxacin, cladarabine, clemastine, clindamycin, clofazamine, clozapine, cocaine, codeine, cyproheptadine, desipramine, dihydroergotamine, diphenidol, diphenoxylate, dipyridamole, docetaxel, doxapram, ergotamine, famciclovir, fentanyl, flavoxate, fludarabine, fluphenazine, fluvastin, ganciclovir, granisteron, guanethidine, haloperidol, homatropine, hydrocodone, hydromorphone, hydroxyzine, hyoscyamine, imipramine, itraconazole, keterolac, ketoconazole, levocarbustine, levorphone, lincomycin, lomefloxacin, loperamide, losartan, loxapine, mazindol, meclizine, meperidine, mepivacaine, mesoridazine, methdilazine, methenamine, methimazole, methotrimeprazine, methysergide, metronidazole, minoxidil, mitomycin c, molindone, morphine, nafzodone, nalbuphine, naldixie acid, nalmefene, naloxone, naltrexone, naphazoline, nedocromil, nicotine, norfloxacin, ofloxacin, ondansteron, oxycodone, oxymorphone, paclitaxel, pentazocine, pentoxyfylline, perphenazine, physostigmine, pilocarpine, pimozide, pramoxine, prazosin, prochlorperazine, promazine, promethazine, quinidine, quinine, rauwolfia alkaloids, riboflavin, rifabutin, risperidone, rocuronium, scopalamine, sufentanil, tacrine, terazosin, terconazole, terfenadine, thioridazine, thiothixene, ticlodipine, timolol, tolazamide, tolmetin, trazodone, triethylperazine, trifluopromazine, trihexylphenidyl, trimeprazine, trimipramine, tubocurarine, vecuronium, vidarabine, vinblastine, vincristine and vinorelbine.

Still further exemplary active agents include those selected from the group consisting of acetazolamide, acravistine, acyclovir, adenosine phosphate, allopurinal, alprazolam, amoxapine, amrinone, apraclonidine, azatadine, aztreonam, bisacodyl, bleomycin, bromopheniramine, buspirone, butoconazole, camptothecin and molecules within the camptothecin family, carbinoxamine, cefamandole, cefazole, cefixime, cefmetazole, cefonicid, cefoperazone, cefotaxime, cefotetan, cefpodoxime, ceftriaxone, cephapirin, chloroquine, chlorpheniramine, cimetidine, cladarabine, clotrimazole, cloxacillin, didanosine, dipyridamole, doxazosin, doxylamine, econazole, enoxacin, estazolam, ethionamide, famciclovir, famotidine, fluconazole, fludarabine, folic acid, ganciclovir, hydroxychloroquine, iodoquinol, isoniazid, itraconazole, ketoconazole, lamotrigine, lansoprazole, lorcetadine, losartan, mebendazole, mercaptopurine, methotrexate, metronidazole, miconazole, midazolam, minoxidil, nafzodone, nalidixic acid, niacin, nicotine, nizatidine, omeperazole, oxaprozin, oxiconazole, papaverine, pentostatin, phenazopyridine, pilocarpine, piroxicam, prazosin, primaquine, pyrazinamide, pyrimethamine, pyroxidine, quinidine, quinine, ribaverin, rifampin, sulfadiazine, sulfamethizole, sulfamethoxazole, sulfasalazine, sulfasoxazole, terazosin, thiabendazole, thiamine, thioguanine, timolol, trazodone, triampterene, triazolam, trimethadione, trimethoprim, trimetrexate, triplenamine, tropicamide, and vidarabine.

Still further exemplary active agents include those belonging to the camptothecin family of molecules. For example, the active agent can possess the general structure:

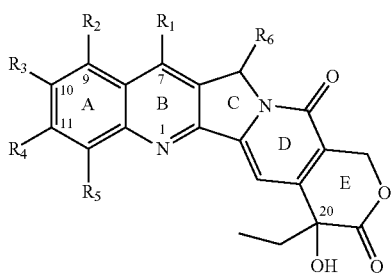

wherein $R_1$, $R_2$, $R_3$, $R_4$ and $R_5$ are each independently selected from the group consisting of: hydrogen; halo; acyl; alkyl (e.g., C1-C6 alkyl); substituted alkyl; alkoxy (e.g., C1-C6 alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—(CH$_2$)$_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy; $R_6$ is H or OR', wherein R' is alkyl, alkenyl, cycloalkyl, haloalkyl, or hydroxyalkyl. Although not shown, analogs having a hydroxyl group corresponding to a position other than the 20-position (e.g., 10-, or 11-position, and so forth) in the immediately preceding structure are encompassed within possible active agents.

An exemplary active agent is irinotecan.

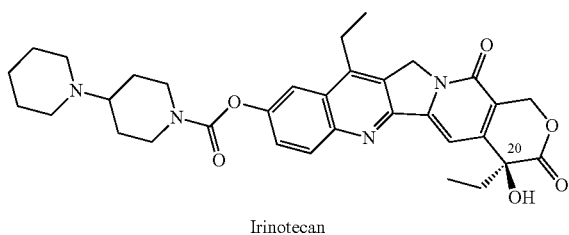 [SMILES: CCc1c2c(nc3ccc(OC(=O)N4CCC(N5CCCCC5)CC4)cc13)-c1cc3c(c(=O)n1C2)COC(=O)[C@]3(O)CC]

Irinotecan

Another exemplary active agent is 7-ethyl-10-hydroxy-camptothecin (SN-38), the structure of which is shown below.

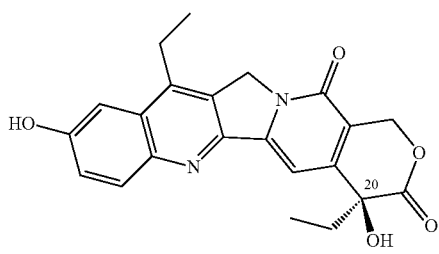

7-ethyl-10-hydroxy-camptothecin

Yet other exemplary class of active agents include those belonging to the taxane family of molecules. An exemplary active agent from this class of molecules is docetaxel where the H of the hydroxy at the 2' hydroxyl group is involved in forming the preferred multi-armed polymer conjugate:

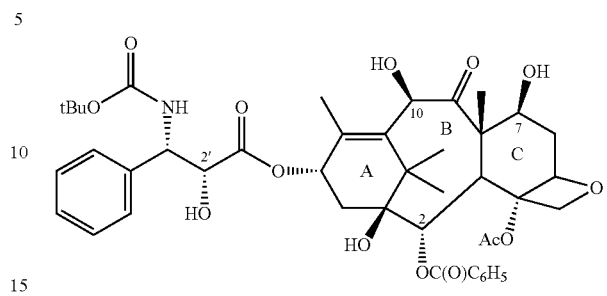

The polymer reagents described herein can be attached, either covalently or noncovalently, to a number of entities including films, chemical separation and purification surfaces, solid supports, metal surfaces such as gold, titanium, tantalum, niobium, aluminum, steel, and their oxides, silicon oxide, macromolecules (e.g., proteins, polypeptides, and so forth), and small molecules. Additionally, the polymer reagents can also be used in biochemical sensors, bioelectronic switches, and gates. The polymer reagents can also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

Optionally, the conjugate can be provided as a pharmaceutical composition for veterinary and for human medical use. Such a pharmaceutical compositions is prepared by combining the conjugate with one or more pharmaceutically acceptable excipients, and optionally any other therapeutic ingredients.

Exemplary pharmaceutically acceptable excipients, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose. D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the active agent and the polymeric reagent) in the composition will vary depending on a number of actors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", 19$^{th}$ ed. Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutically acceptable compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline. Ringer's solution, saline, sterile water, deionized water, and combinations thereof. With respect to liquid pharmaceutical compositions, solutions and suspensions are envisioned.

The compositions of one or more embodiments of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

The invention also provides a method for administering a conjugate as provided herein to a patient suffering from a condition that is responsive to treatment with conjugate. The method comprises administering to a patient, generally via injection, a therapeutically effective amount of the conjugate (preferably provided as part of a pharmaceutical composition). As previously described, the conjugates can be administered injected parenterally by intravenous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of the conjugate. Those of ordinary skill in the art appreciate which conditions a specific conjugate can effectively treat. Advantageously, the conjugate can be administered to the patient prior to, simultaneously with, or after administration of another active agent.

The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature Generally, a therapeutically effective amount will range from about 0.001 mg to 100 mg, preferably in doses from 0.01 mg/day to 75 mg/day, and more preferably in doses from 0.10 mg/day to 50 mg/day. A given dose can be periodically administered up until, for example, related symptoms lessen and/or are eliminated entirely.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly, once monthly, and any combination thereof. Once the clinical endpoint has been achieved, dosing of the composition is halted.

One advantage of administering certain conjugates described herein is that individual water-soluble polymer portions can be cleaved when a hydrolytically degradable linkage is included between the residue of the active agent moiety and water-soluble polymer. Such a result is advantageous when clearance from the body is potentially a problem because of the polymer size. Optimally, cleavage of each water-soluble polymer portion is facilitated through the use of physiologically cleavable and/or enzymatically degradable linkages such as amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

Mixed Salts—Considerations Concerning the Active Agent, "D"

As indicated previously, water-soluble polymer conjugates and compositions containing these conjugates may be provided as mixed salts. In the mixed salt conjugate and composition context, the active agent is a small molecule drug, an oligopeptide, a peptide, or a protein, that, when conjugated to the water-soluble polymer, contains at least one basic nitrogen atom such as an amine group (e.g., an amine or other basic nitrogen containing group that is not conjugated to the water-soluble polymer). In the mixed salt, the basic nitrogen atoms are each individually either protonated or unprotonated, where the protonated nitrogen atoms exist as acid salts of two different anions.

Active agents containing at least one amine group or basic nitrogen atom suitable for providing a mixed acid salt as described herein include but are not limited to the following: adriamycin, γ-aminobutyric acid (GABA), amiodarone, amitryptyline, azithromycin, benzphetamine, bromopheniramine, cabinoxamine, calcitonin chlorambucil, chloroprocaine, chloroquine, chlorpheniramine, chlorpromazine, cinnarizine, clarthromycin, clomiphene, cyclobenzaprine, cyclopentolate, cyclophosphamide, dacarbazine, daunomycin, demeclocycline, dibucaine, dicyclomine, diethylproprion, diltiazem, dimenhydrinate, diphenhydramine, disopyramide, doxepin, doxycycline, doxylamine, dypyridame, EDTA, erythromycin, flurazepam, gentian violet, hydroxychloroquine, imipramine, insulin, irinotecan, levomethadyl, lidocaine, loxarine, mechlorethamine, melphalan, methadone, methotimeperazine, methotrexate, metoclopramide, minocycline, naftifine, nicardipine, nizatidine, orphenadrine, oxybutin, oxytetracycline, phenoxybenzamine, phentolamine, procainamide, procaine, promazine, promethazine, proparacaine, propoxycaine, propoxyphene, ranitidine, tamoxifen, terbinafine, tetracaine, tetracycline, tranadol, triflupromazine, trimeprazine, trimethylbenzamide, trimipramine, tripelennamine, troleandomycin, tyramine, uracil mustard, verapamil, and vasopressin.

Additional active agents include those comprising one or more nitrogen-containing heterocycles such as acravistine, amoxapine, astemizole, atropine, azithromycin, benzapril, benztropine, beperiden, bupracaine, buprenorphine, buspirone, butorphanol, caffeine, camptothecin and molecules belonging to the camptothecin family, ceftriaxone, chlorpromazine, ciprofloxacin, cladarabine, clemastine, clindamycin, clofazamine, clozapine, cocaine, codeine, cyproheptadine, desipramine, dihydroergotamine, diphenidol, diphenoxylate, dipyridamole, doxapram, ergotamine, famciclovir, fentanyl, flavoxate, fludarabine, fluphenazine, fluvastin, ganciclovir, granisteron, guanethidine, haloperidol, homatropine, hydrocodone, hydromorphone, hydroxyzine, hyoscyamine, imipramine, itraconazole, keterolac, ketoconazole, levocarbustine, levorphone, lincomycin, lomefloxacin, loperamide, losartan, loxapine, mazindol, meclizine, meperidine, mepivacaine, mesoridazine, methdilazine, methenamine, methimazole, methotrimeprazine, methysergide, metronidazole, minoxidil, mitomycin c, molindone, morphine, nafzodone, nalbuphine, nalidixic acid, nalmefene, naloxone, naltrexone, naphazoline, nedocromil, nicotine, norfloxacin, ofloxacin, ondansteron, oxycodone, oxymorphone, pentazocine, pentoxyfylline, perphenazine, physostigmine, pilocarpine, pimozide, pramoxine, prazosin, prochlorperazine, promazine, promethazine, quinidine, quinine, rauwolfia alkaloids, riboflavin, rifabutin, risperidone, rocuronium, scopalamine, sufentanil, tacrine, terazosin, terconazole, terfenadine, thiordazine, thiothixene, ticlodipine, timolol, tolazamide, tolmetin, trazodone, triethylperazine, trifluopromazine, trihexylphenidyl, trimeprazine, trimipramine, tubocurarine, vecuronium, vidarabine, vinblastine, vincristine and vinorelbine.

Additional active agents include those comprising an aromatic ring nitrogen such as acetazolamide, acravistine, acyclovir, adenosine phosphate, allopurinal, alprazolam, amoxapine, amrinone, apraclonidine, azatadine, aztreonam, bisacodyl, bleomycin, bromopheniramine, buspirone, butoconazole, camptothecin and molecules within the camptothecin family, carbinoxamine, cefamandole, cefazole, cefixime, cefmetazole, cefonicid, cefoperazone, cefotaxime, cefotetan, cefpodoxime, ceftriaxone, cephapirin, chloroquine, chlorpheniramine, cimetidine, cladarabine, clotrimazole, cloxacillin, didanosine, dipyridamole, doxazosin, doxylamine, econazole, enoxacin, estazolam, ethionamide, famciclovir, famotidine, fluconazole, fludarabine, folic acid, ganciclovir, hydroxychloroquine, iodoquinol, isoniazid, itraconazole, ketoconazole, lamotrigine, lansoprazole, lorcetadine, losartan, mebendazole, mercaptopurine, methotrexate, metronidazole, miconazole, midazolam, minoxidil, nafzodone, naldixic acid, niacin, nicotine, nizatidine, omeperazole, oxaprozin, oxiconazole, papaverine, pentostatin, phenazopyridine, pilocarpine, piroxicam, prazosin, primaquine, pyrazinamide, pyrimethamine, pyroxidine, quinidine, quinine, ribaverin, rifampin, sulfadiazine, sulfamethizole, sulfamethoxazole, sulfasalazine, sulfasoxazole, terazosin, thiabendazole, thiamine, thioguanine, timolol, trazodone, triampterene, triazolam, trimethadione, trimethoprim, trimetrexate, triplenamine, tropicamide, and vidarabine.

A preferred active agent is one belonging to the camptothecin family of molecules. For example, the active agent may possess the general structure:

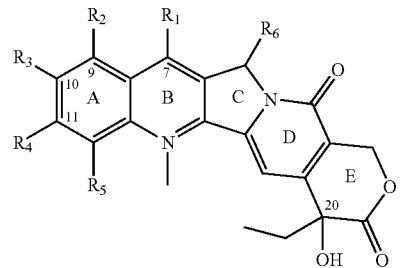

wherein $R_1$-$R_5$ are each independently selected from the group consisting of hydrogen; halo; acyl; alkyl (e.g., C1-C6 alkyl); substituted alkyl; alkoxy (e.g., C1-C6 alkoxy); substituted alkoxy; alkenyl; alkynyl; cycloalkyl; hydroxyl; cyano;

nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—(CH$_2$)$_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy; $R_6$ is H or OR', wherein R' is alkyl, alkenyl, cycloalkyl, haloalkyl, or hydroxyalkyl.

In reference to the foregoing structure, although not shown, analogs having a hydroxyl group at other than the 20-position (e.g., 10-, or 11-position, etc.) are similarly preferred.

In one particular embodiment, the active agent is irinotecan (structure shown below).

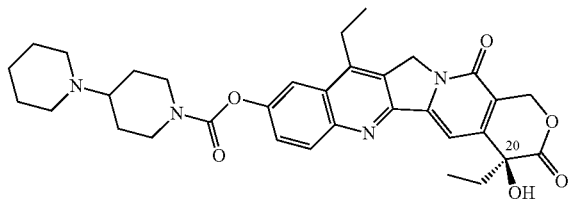 [SMILES: CCc1c2c(nc3ccc(OC(=O)N4CCC(N5CCCCC5)CC4)cc13)-c1cc3c(c(=O)n1C2)COC(=O)[C@]3(O)CC]

In yet another particular embodiment, the active agent is 7-ethyl-10-hydroxy-camptothecin (SN-38), a metabolite of irinotecan, whose structure is shown below.

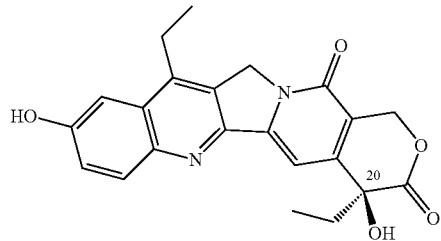 [SMILES: CCc1c2c(nc3ccc(O)cc13)-c1cc3c(c(=O)n1C2)COC(=O)[C@]3(O)CC]

Mixed Salts—Considerations Concerning the Conjugates

Illustrative mixed salt conjugates of a water-soluble polymer and an active agent may possess any of a number of structural features as described above. That is to say, the conjugate may possess a linear structure, i.e., having one or two active agent molecules covalently attached to a linear water-soluble polymer, typically at each terminus of the linear water-soluble polymer. Alternatively, the conjugate may possess a forked, branched or multi-armed structure.

One exemplary multi-armed polymer conjugate corresponds to the following generalized structure: R(-Q-POLY$_1$-X-D)$_q$, wherein R is an organic radical possessing from about 3 to about 150 carbon atoms, Q is a linker (preferably hydrolytically stable and may be —O—, —S—, —NH—C(O)— and —C(O)—NH—. POLY$_1$ is a water-soluble, non-peptidic polymer. X is spacer that comprises a hydrolyzable linkage, D is an active agent moiety, and q ranges from 3 to 25 (e.g. 3 to 10, such as any of 3, 4, 5, 6, 7, 8, 9 and 10).

Another exemplary multi-armed polymer conjugate corresponds to the following generalized structure: R(-Q-POLY$_1$-CH$_2$C(O)—NH—CH$_2$—C(O)—O-D)$_q$, wherein: R is an organic radical possessing from 3 to 50 carbon atoms; Q is a linker, wherein R, when taken together with Q to form R(-Q-)$_q$, is a residue of a polyol or a polythiol after removal of "q" hydroxyl or thiol protons, respectively, to form a point of attachment for POLY$_1$; POLY$_1$, is a water-soluble polymer selected from the group consisting of poly(alkylene glycol), poly(olefinic alcohol), poly(vinylpyrrolidone), poly(hydroxylalkyl-methacrylamide), poly(hydroxyalkyl-methacrylate), poly($\alpha$-hydroxy acid), poly(acrylic acid), poly(vinyl alcohol), polyphosphazene, polyoxazoline, poly(N-acryloylmorpholine), and copolymers or terpolymers thereof; D is a camptothecin attached at its 10-, 11- or 20-ring position; and q has a value from 3 to 50 (e.g., 3 to 10, such as any of 3, 4, 5, 6, 7, 8, 9 and 10).

One illustrative multi-armed polymer conjugate structure corresponds to the following structure:

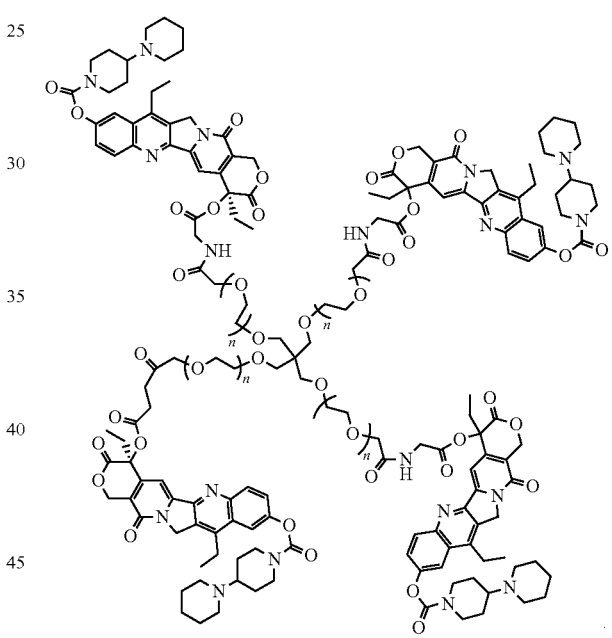

The foregoing structure is referred to herein in shorthand fashion as "4-arm-PEG-Gly-Irino" (4-arm-pentaerythritolyl-PEG-carboxymethylglycine irinotecan); a more complete name corresponds to "pentaerythritolyl-4-arm-(PEG-1-methylene-2-oxo-vinylamino acetate linked-irinotecan)." Basic amino and/or nitrogen groups in the active agent portion of the conjugate are shown above in only neutral form, with the understanding that the conjugate possesses the features of a partial mixed salt as described in detail herein. As can be seen from the structure above, the carboxymethyl modified 4-arm pentaerythritolyl PEG reagent possesses a glycine linker intervening between the polymer portion and the active agent, irinotecan.

In certain instances, due to incomplete conversions, less than 100% yields, and other unavoidable complications routinely encountered during chemical syntheses, in particular of multi-arm polyethylene glycol-based materials, exemplary compositions comprising "4-arm-PEG-Gly-Irino" can be characterized as compositions comprising four-arm conjugates, wherein at least 90% of the four-arm conjugates in the composition:

(i) have a structure encompassed by the formula,

C—[CH$_2$—O—(CH$_2$CH$_2$O)$_n$—CH$_2$—C(O)-Term]$_4$, wherein n, in each instance, is an integer having a value from 5 to 150 (e.g., about 113), and Term, in each instance, is selected from the group consisting of —OH, —OCH$_3$,

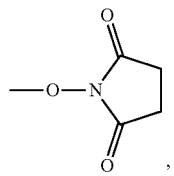

—NH—CH$_2$—C(O)—OH, —NH—CH$_2$—C(O)—OCH$_3$,

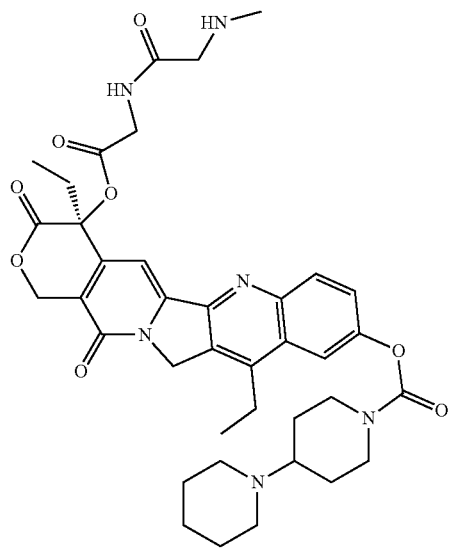

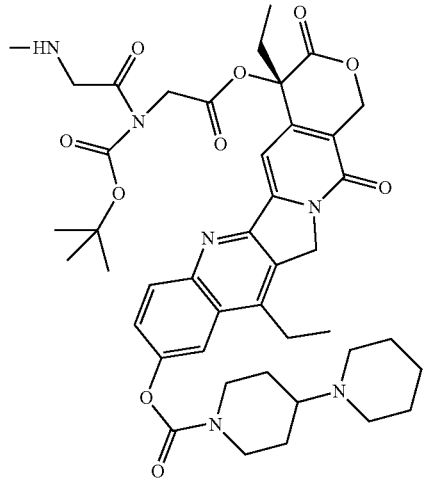

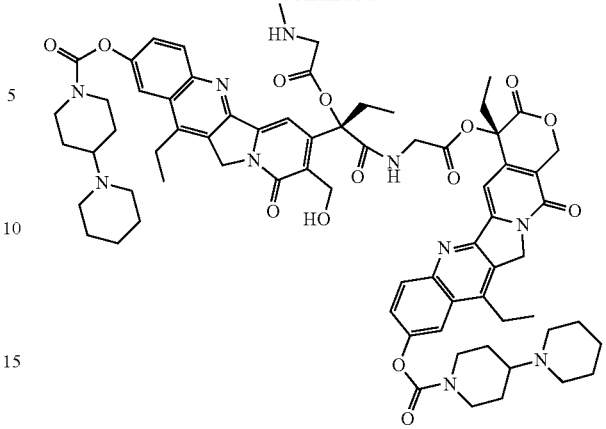

and —NH—CH$_2$—C(O)—O-Irino ("GLY-irino"), wherein Irino is a residue of irinotecan; and (ii) for each Term in the at least 90% of the four-arm conjugates in the composition, at least 90% thereof are —NH—C$_{1-2}$—C(O)—O-Irino.

Typically, although not necessarily, the number of polymer arms will correspond to the number of active agent molecules covalently attached to the water-soluble polymer core. That is to say, in the case of a polymer reagent having a certain number of polymer arms (e.g., corresponding to the variable "q"), each having a reactive functional group (e.g., carboxy, activated ester such as succinimidyl ester, benzotriazolyl carbonate, and so forth) at its terminus, the optimized number of active agents (such as irinotecan) that can be covalently attached thereto in the corresponding conjugate is most desirably "q." That is to say, the optimized conjugate is considered to have a drug loading value of 1.00(q) (or 100%). In a preferred embodiment, the multi-armed polymer conjugate is characterized by a degree of drug loading of 0.90(q) (or 90%) or greater. Preferred drug loadings satisfy one or more of the following: 0.92(q) or greater; 0.93(q) or greater: 0.94(q) or greater; 0.95(q) or greater: 0.96(q) or greater: 0.97(q) or greater; 0.98(q) or greater; and 0.99(q) or greater. Most preferably, the drug loading for a multi-armed polymer conjugate is one hundred percent. A composition comprising a multi-arm water soluble polymer conjugate mixed acid salt may comprise a mixture of molecular conjugates having one active agent attached to the polymer core, having two active agent molecules attached to the polymer core, having three active agents attached to the polymer core, and so on, up to and including a conjugate having "q" active agents attached to the polymer core. The resulting composition will possess an overall drug loading value, averaged over the conjugate species contained in the composition. Ideally, the composition will comprise a majority, e.g., greater than 50%, but more preferably greater than 60%, still more preferably greater than 70%, still yet more preferably greater than 80%, and most preferably greater than 90%) of drug fully loaded polymer conjugates (i.e. having "q" active agent molecules for "q" arms, a single active agent molecule for each arm).

As an illustration, in an instance in which the multi-armed polymer conjugate contains four polymer arms, the idealized value of the number of covalently attached drug molecules per multi-armed polymer is four, and—with respect to describing the average in the context of a composition of such conjugates—there will be a value (i.e., percentage) of drug molecules loaded onto multi-armed polymer ranging from about 90% to about 100% of the idealized value. That is to say, the average number of drug molecules covalently attached to a given four-armed polymer (as part of a four-armed polymer composition) is typically 90%, 91%, 92%, 93%, 94%, 95%, 96%, 97%, 98%, 99%, and 100% of the fully loaded value. This corresponds to an average number of D per multi-arm polymer conjugate ranging from about 3.60 to 4.0.

In yet another embodiment, for a multi-armed polymer conjugate composition, e.g., where the number of polymer arms ranges from about 3 to about 8, e.g., greater than 50%, but more preferably greater than 60%, still more preferably greater than 70%, still yet more preferably greater than 80%, and most preferably greater than 90%) of species present in the composition are those having either an idealized number of drug molecules attached to the polymer core ("q") or those having a combination of ("q") and ("q–1") drug molecules attached to the polymer core.

In certain instances, a multi-armed polymer conjugate such as described herein is prepared, where the resulting conjugate exhibits a high degree of substitution or drug loading in the context of the ranges provided above. Illustrative conjugates thus prepared will generally have a drug loading value of at least 90%, and may typically possess drug loading values of greater than 91%, or greater than 92%. 93%, 94%, 95%. 96%, 97%, 98%, or 99%, and in some cases, at 100% of the fully loaded value. In particular, multi-armed polymer conjugates prepared from multi-arm polymeric starting materials that are prepared, e.g., in accordance with the alkoxylation methodology provided herein, may exhibit higher drug substitution values, due, at least in part, to the purity of the polymeric starting material. As an example, 4-arm PEG-CM-SCM (e.g., having a molecular weight greater than about 10 kilodaltons) prepared from 4-arm PEG-OH prepared according to the alkoxylation method provided herein, may possess, on average, a higher level of purity with respect to the particular polymer species present in the 4-arm-PEG-CM-SCM reactant material than obtained with other commercially available 4-arm PEG-OH starting materials (e.g., having fewer low molecular weight polymer impurities). The level of purity of a multi-arm PEG starting material, especially those of higher molecular weight, can contribute to the purity of the final conjugate product in the event that non-desired polymer materials present in the polymeric starting material are "carried along" in subsequent transformation steps. In particular, in employing synthetic methodologies having high yield reaction steps, e.g., carboxymethylation, coupling to an active agent such as deprotected glycine-irinotecan, utilization of a polymeric starting material having a relatively high amount of polymeric impurities, can impact the purity and drug loading values of the resulting conjugate species, in certain cases by several percent. Moreover, the presence of even a small percentage of low molecular weight polymer conjugate species in the final mixed salt conjugate can lead to reduced bioavailability, since the small molecular weight conjugates will clear more rapidly. Polymer conjugates prepared from starting materials prepared using the alkoxylation method described herein may therefore exhibit higher bioavailabilities than polymer conjugates prepared from commercially available multi-arm starting materials containing up to, e.g., 20% (e.g., 2, 3, 4, 5, 6, 7, 8, 9, 10, 11, 12, 13, 14, 15, 16, 17, 18, 19 or 20%), low molecular weight or other polymer impurities.

In accordance with the foregoing, the partial mixed salt (and compositions containing the same) may comprise any one or more of the following structures, in addition to the fully drug loaded structure (i.e. having a glycine-modified irinotecan molecule covalently attached to each of the four polymer arms):

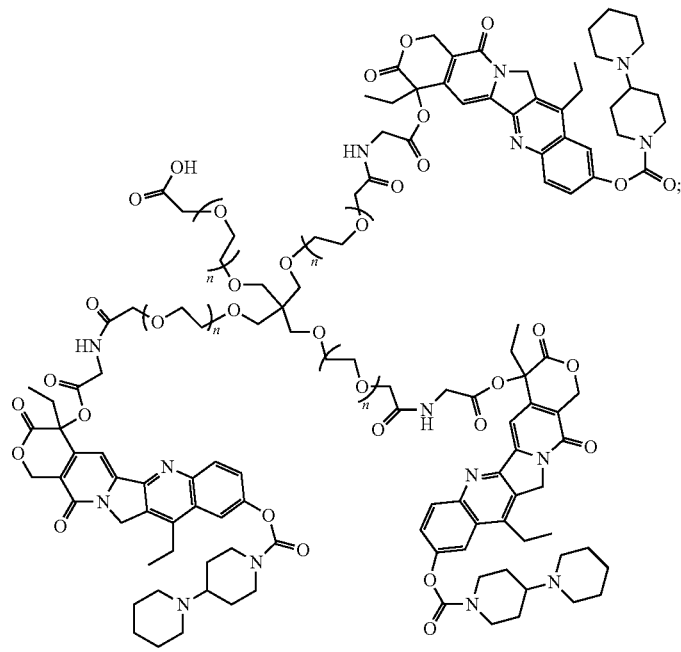

-continued
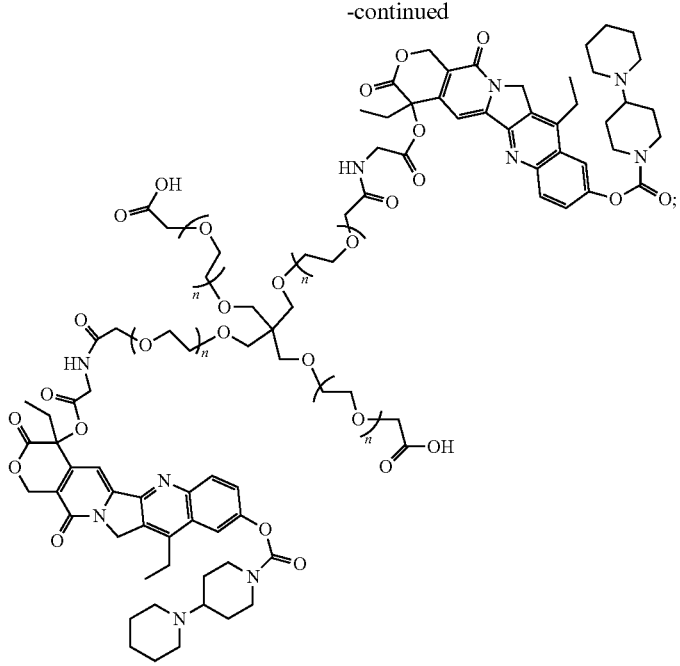
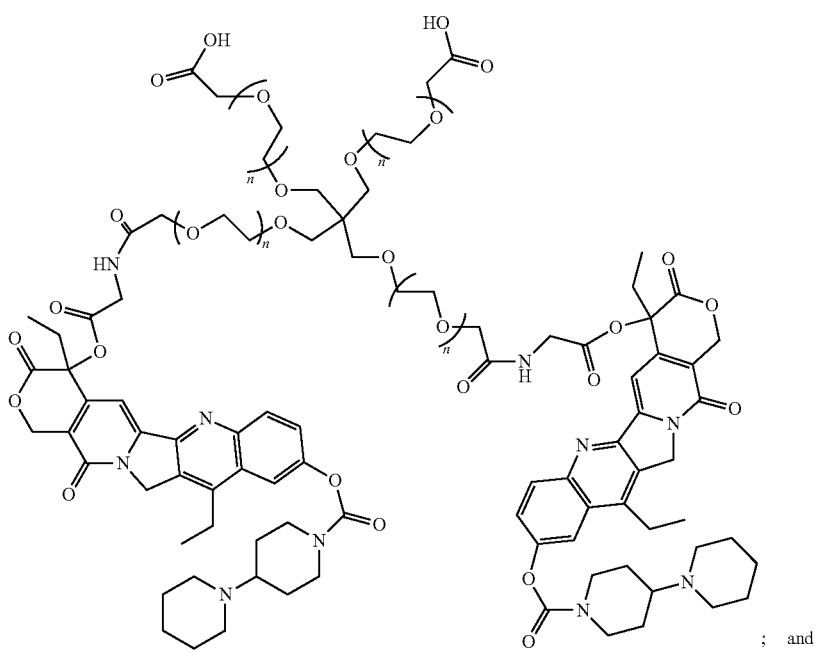
; and

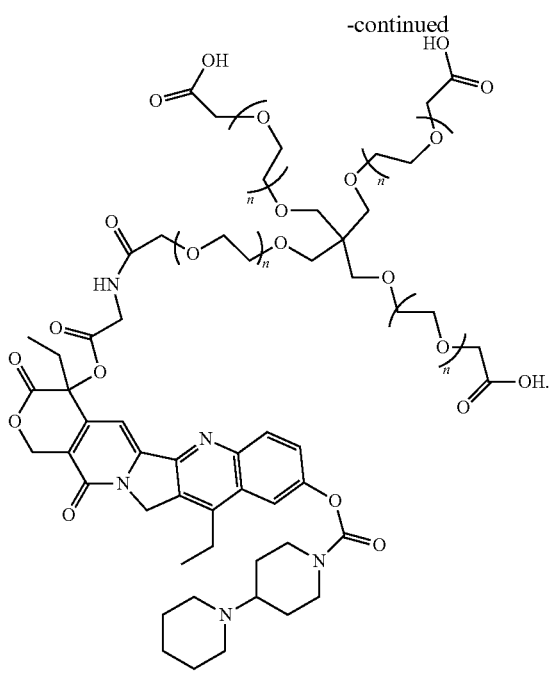
For a given polymer arm terminus shown above having a carboxylic acid (and therefore not covalently attached to drug, e.g., irinotecan), other possible termini extending from the 4-arm-PEG-CM (—CH$_2$C(O)—) arm include —OH, —OCH$_3$,
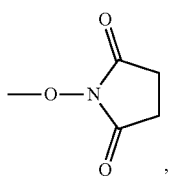
NH—CH$_2$—C(O)—OH, NH—CH$_2$—C(O)—OCH$_3$,
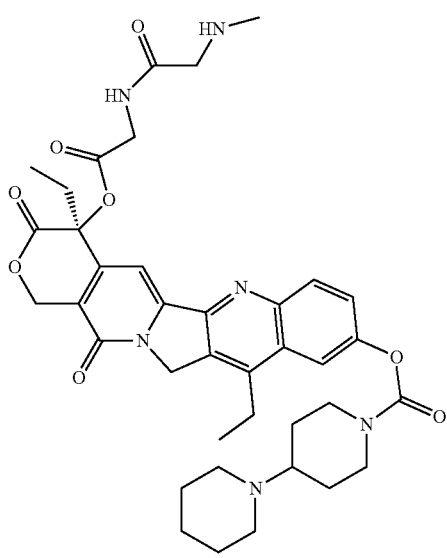
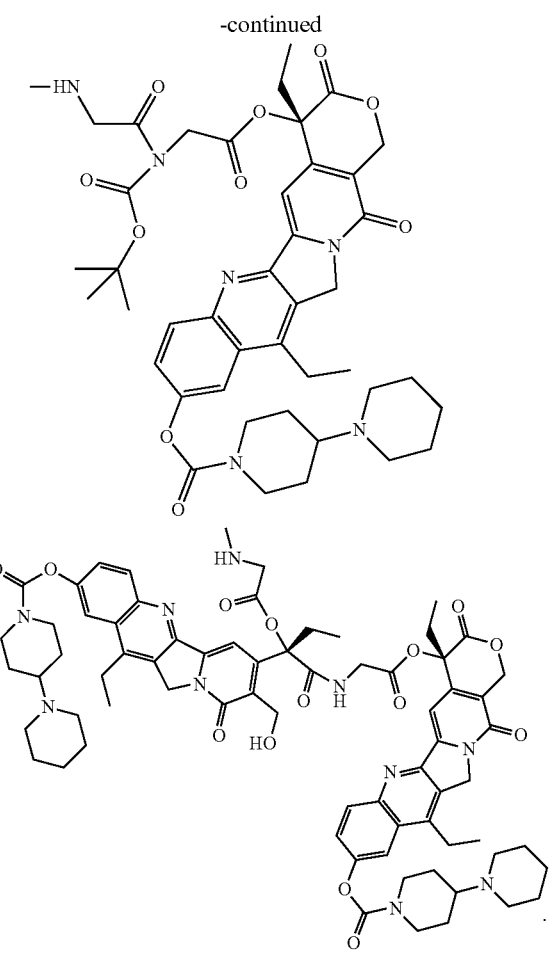
The multi-arm polymer conjugate compositions provided herein are intended to encompass any and all stereoisomeric forms of the conjugates comprised in such compositions. In a particular embodiment of the conjugate, the stereochemistry at C-20 of irinotecan, when in conjugated form such as in compositions of 4-arm-PEG-Gly-Irino, remains intact, i.e., C-20 retains its (S)-configuration when in its conjugated form. See, e.g., Example 4.

Yet another preferred multi-armed structure is a carboxymethyl modified 4-arm pentaerythritolyl PEG having a glycine linker intervening between the polymer portion in each arm and the active agent (polymer portion and linker shown above), where the active agent is 7-ethyl-O-hydroxy-camptothecin. Again, included herein are embodiments in which the multi-arm polymer is (i) fully loaded, as well as having (ii) three 7-ethyl-10-hydroxy-camptothecin molecules covalently attached thereto, (iii) two 7-ethyl-10-hydroxy-camptothecin molecules covalently attached thereto, and (iv) one 7-ethyl-10-hydroxy-camptothecin molecule covalently attached to the four-arm polymer core.

Yet another representative multi-armed conjugate structure is a carboxymethyl modified 4-arm glycerol dimer (3,3'-oxydipropane-1,2-diol) PEG having 7-ethyl-O-hydroxy-camptothecin (SN-38) molecules covalently attached to the polymer core. Embodiments in which the multi-armed polymer core is fully loaded with drug (i.e., having four 7-ethyl-10-hydroxy-camptothecin molecules covalently attached thereto), or is less than fully loaded (i.e., having one, two, or three 7-ethyl-10-hydroxy-camptothecin molecules covalently attached thereto) are included herein. The conjugate having drug (i.e., 7-ethyl-10-hydroxy-camptothecin) covalently attached to each polymer arm is shown below.

having one, two, or three irinotecan molecules covalently attached thereto) are included herein.

Parameters of the Mixed Salts

The subject compositions can be, among other things, partial mixed acid salts. That is to say, mixed salt conjugates are provided in a composition such that basic nitrogen atoms in the conjugate (as well as in the bulk composition) may individually be present in either protonated or non-protonated forms with the protonated nitrogen atoms (referred to as acid salts) having one of two different counter anions. One anion corresponds to the conjugate base of a strong inorganic acid such as a hydrohalic acid, sulfuric acid, nitric acid, phosphoric acid, nitrous acid, and the like; the other anion corresponds to the conjugate base of a strong organic acid such as trifluoroacetate. The subject mixed acid salt compositions are stably and reproducibly prepared.

A mixed acid salt as provided herein is characterized in terms of its bulk or macro properties. That is to say, basic nitrogen atoms (i.e., amino groups) in the conjugate exist individually in either neutral (non-protonated) or protonated form, the protonated forms associated with one of two different possible counterions. While the present compositions are characterized based on bulk properties, different individual molecular species are contained within the bulk composition. Taking the exemplary 4-arm polymer conjugate described in Example 1, 4-arm-PEG-Gly-Irino-20K, the mixed acid salt product contains any of a number of individual molecular species. One molecular species is one in which each polymer arm contains an irinotecan molecule that is in neutral form,

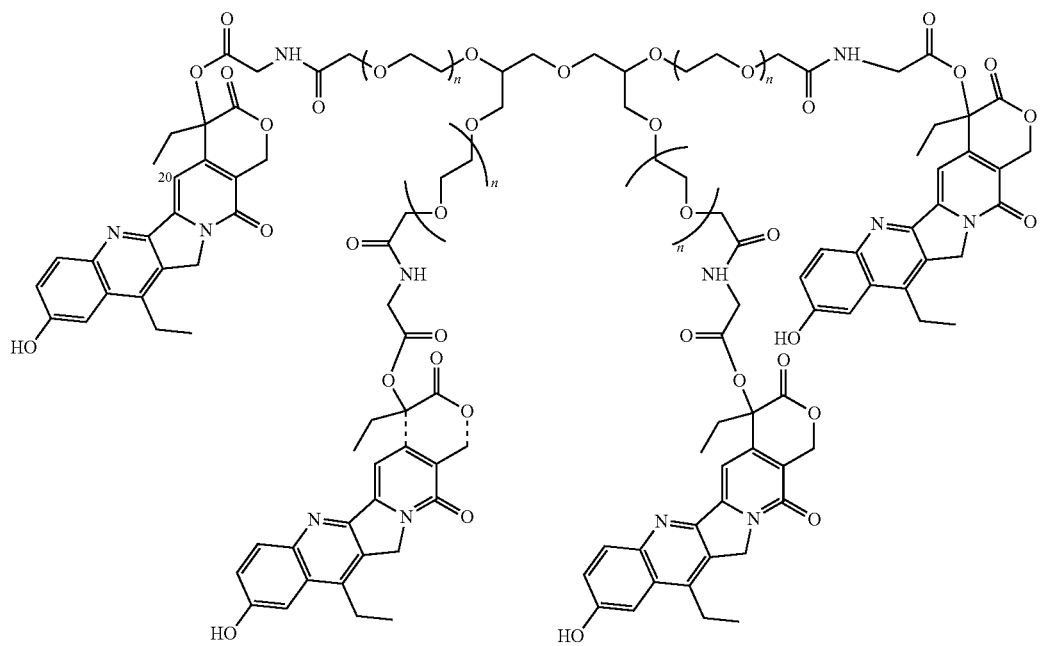

In yet another illustrative embodiment, the conjugate is a multi-armed structure comprising a carboxymethyl modified 4-arm glycerol dimer (3,3'-oxydipropane-1,2-diol) PEG having irinotecan molecules covalently attached to the polymer core. Embodiments in which the multi-armed polymer core is fully loaded with drug (i.e. having four irinotecan molecules covalently attached thereto), or is less than fully loaded (i.e., i.e., its amino group is unprotonated. See structure 1 below. Another molecular species is one in which each polymer arm contains an irinotecan molecule in protonated form. See structure IV below. An additional molecular species is one in which three of the polymer arms contain an irinotecan molecule that is in protonated form, and one polymer arm contains an irinotecan molecule in neutral form (structure III). In another molecular species, two of the four polymer arms contain an irinotecan molecule in neutral form (i.e., its amino group is unprotonated), and two of the four polymer arms contain an irinotecan molecule that is in protonated form (structure II). Within all of the molecular species described above with the exception of the first "all neutral" form, subspecies of molecules are possible containing different combinations of counterions. The schematic below illustrates various possible combinations; the table that follows indicates possible combinations of protonated acid salts corresponding to each structure.

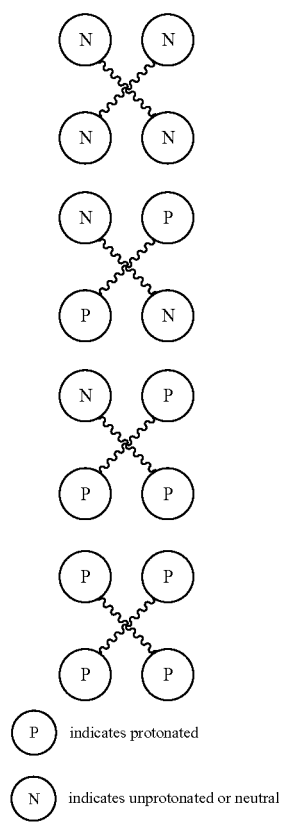

P indicates protonated

N indicates unprotonated or neutral

| | II | III | IV |
|---|---|---|---|
| I<br>No P | P, P<br>combinations | P, P, P<br>combinations | P, P, P, P<br>combinations |
| all unprotonated,<br>i.e., the same | TFA, TFA<br>TFA, Cl<br>Cl, Cl | TFA, TFA, TFA<br>Cl, Cl, Cl<br>TFA, Cl, Cl<br>Cl, TFA, TFA | Cl, Cl, Cl, Cl,<br>TFA, TFA, TFA, TFA<br>Cl, TFA, TFA, TFA<br>Cl, Cl, TFA, TFA<br>TFA, Cl, Cl, Cl |

As demonstrated in Example 1 and in Example 6, certain exemplary polymer prodrug conjugates are obtained as mixed acid salts of both hydrochloric acid and trifluoroacetic acid. In Example 1, hydrochloric acid is introduced by the use of an acid salt form of the active agent molecule to form the resulting polymer conjugate, while the trifluoroacetic acid is introduced to the reaction mixture in a deprotection step (although any strong acid may be used). Following covalent attachment of the active agent (or modified active agent as illustrated in Example 1) to the water soluble polymer reagent, and treatment with base, even in instances in which additional purification steps are carried out, the resulting conjugate is unexpectedly and reproducibly obtained as a partial mixed acid salt having surprising and beneficial properties, to be described in greater detail below. Even after repeated purifications, it has been discovered there is a persistent and repeatable association of the exemplary strong inorganic acid, hydrochloric acid, and trifluoroacetic acid in the resulting conjugate. See, e.g., Example 2, Table 1 and Example 6. Table 2.

The mixed acid salt conjugates described herein preferably contain fairly well-defined proportions and ranges of each component (i.e., free base, inorganic acid salt, organic acid salt). The characteristics of the mixed acid salt product, may of course, vary depending upon changes to the synthesis conditions employed. In looking at the compositions prepared in accordance with the method described in Example 1, the polymer conjugate mixed acid salt is consistently recovered as having the greatest relative molar amount of basic nitrogen atoms in protonated form in comparison to free base (or unprotonated) nitrogens (calculated with respect to basic nitrogen atoms in the active agent). Thus, if all basic nitrogens in the active agent portion of the conjugate are unprotonated, the corresponding molar percent would be 100. In one embodiment, the partial mixed salt composition is characterized as having the greatest relative molar amount of TFA salt (in comparison to hydrochloride salt and free base). In yet another particular embodiment, the partial mixed salt composition is characterized as typically comprising a lesser relative molar amount of hydrohalic salt (in comparison to TFA salt), and even less of unprotonated (free base) nitrogens. In one embodiment, the partial mixed salt composition comprises approximately 30-75 mole percent TFA salt, approximately 15-45 mole percent hydrohalic acid salt, and 2-55 mole percent free base. These relative amounts may of course vary with variations in process conditions for making the mixed acid salt. For example, in yet another embodiment, the mole percentage of trifluoroacetic acid salt ranges from about 45 to 70, the mole percentage of hydrochloric acid salt ranges from about 20 to 38, and the mole percentage of free base ranges from about 10 to 35. Generally, for the earlier batches of conjugates prepared, active agent basic nitrogen (e.g., amino) groups within the conjugate are present in the highest molar percentage as the trifluoroacetic acid salt, in the second highest molar percentage as the hydrochloric acid salt, and in the third or least highest molar percentage as the free base. In certain embodiments, the mole percentages of hydrochloride salt and free base in the conjugate are about the same. Taking the average relative molar amounts of trifluoroacetic acid salt, hydrochloride salt, and free base in the conjugate over lots tested, on average, the product contained about 50 mole percent trifluoroacetic acid salt, about 30 mole percent hydrochloric acid salt, and about 20 mole percent free base.

Turning now to Example 6, it can be seen that mixed acid salt conjugates have been prepared, where the relative molar amounts of each of TFA salt, hydrodrochloride salt, and unprotonated material among the four different lots exhibit a high level of consistency. Similar to the results in Example 1, the polymer conjugate mixed acid salt is consistently recovered as having the greatest relative molar amount of basic nitrogen atoms in protonated form in comparison to free base (or unprotonated) nitrogens (calculated with respect to basic nitrogen atoms in the active agent). In the lots summarized in Table 2, the partial mixed salt compositions having the greatest relative molar amount of HCl salt in comparison to TFA salt and free base. In yet another particular embodiment, the partial mixed salt composition may be characterized as typically comprising a lesser relative molar amount of TFA salt in comparison to the HCl salt, and even less of unprotonated (free base) nitrogens. In one embodiment, the partial mixed salt composition will comprises at least about 20 mole percent TFA, or at least about 25 mole percent TFA. Exemplary ranges of TFA salt within the mixed salt composition may range from about 20-45 mole percent, or from about 24-38 mole percent, or even from about 35 to 65 mole percent. With respect to hydrochloride salt, the composition may, in certain embodiments, possess from about 30 to 65 mole percent hydrochloride, or from about 32 to 60 mole percent hydrochloride, or preferably, from about 35 to 57 mole percent hydrochloride.

The mixed acid salt conjugates described herein were generally found to possess greater stability than either the pure HCl salt or the free base forms of the conjugate. See, e.g., Example 3 and FIG. 1, illustrating the results of stress stability tests on compositions containing varied amounts of salt and free base forms of an exemplary conjugate. 4-arm-PEG-GLY-IRT. A positive correlation was observed between increased stability towards hydrolysis and increased molar percentage of salt in the final conjugate product. Based upon the slopes of the graphs, it can be determined that as free base content increases, product stability decreases. A correlation between decrease in product and increase in irinotecan over time was observed, thereby leading to a determination that the mode of decomposition observed under the conditions employed was ester bond hydrolysis.

Figure 2:
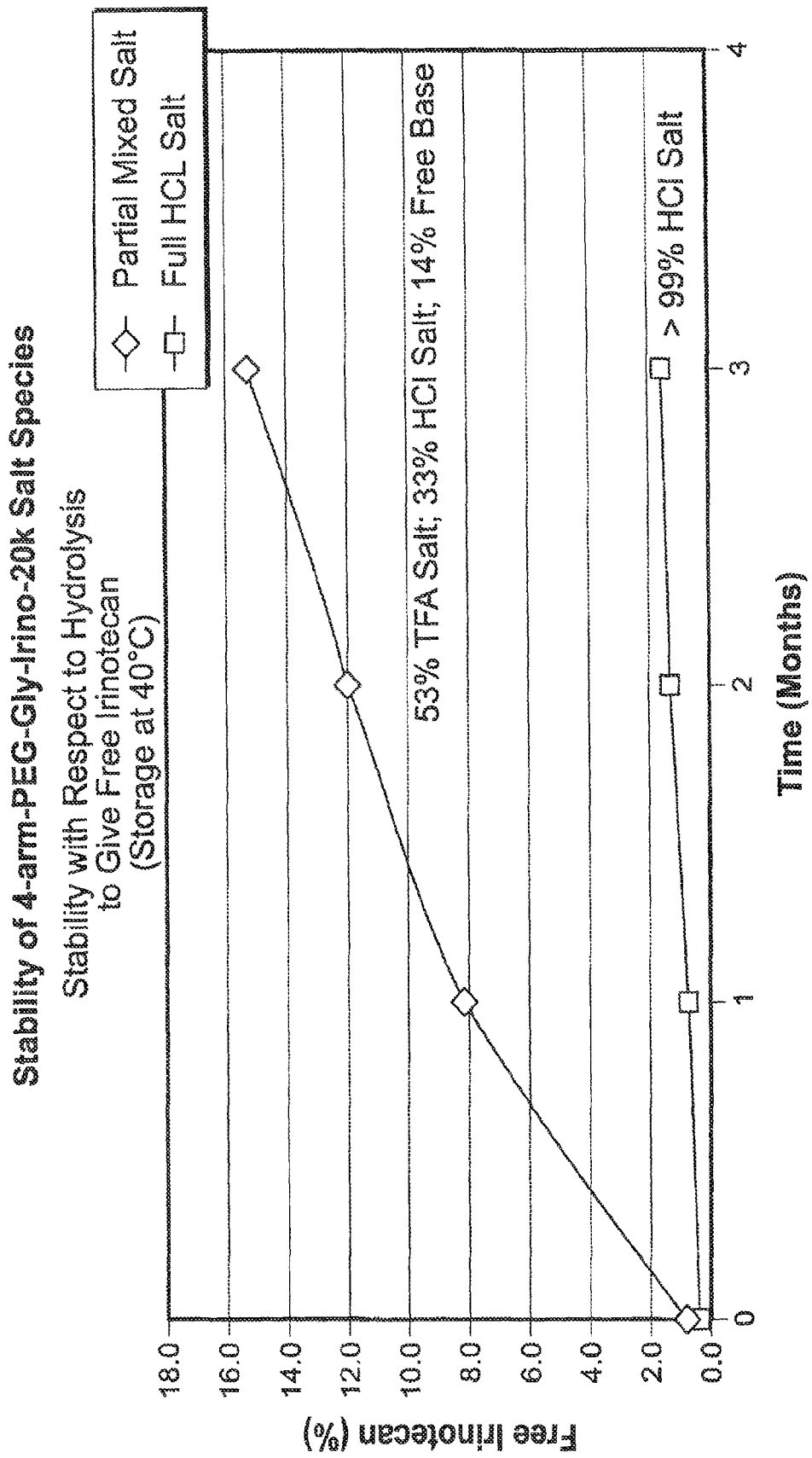
FIG. 2 is a graph illustrating the increase in free irinotecan over time in samples of 4-arm-PEG-Gly-Irino-20K stored at 40° C. and 75% relative humidity, each having a different composition with respect to relative amounts of trifluoroacetic acid and hydrochloride salts, as well as free base. Samples tested correspond to product containing >99% HCl salt (<1% free base, squares) and product containing 86% total salts (14% free base, diamonds), as described in Example 3.

FIG. 2 further illustrates that stability (or resistance) against hydrolytic degradation is greater for conjugates possessing a greater degree of protonated amine groups (i.e., acid salt). For instance, it was observed that conjugate product containing 14 molar percent or more free base was notably less stable towards hydrolysis than the corresponding acid salt-rich product.

Figure 3:
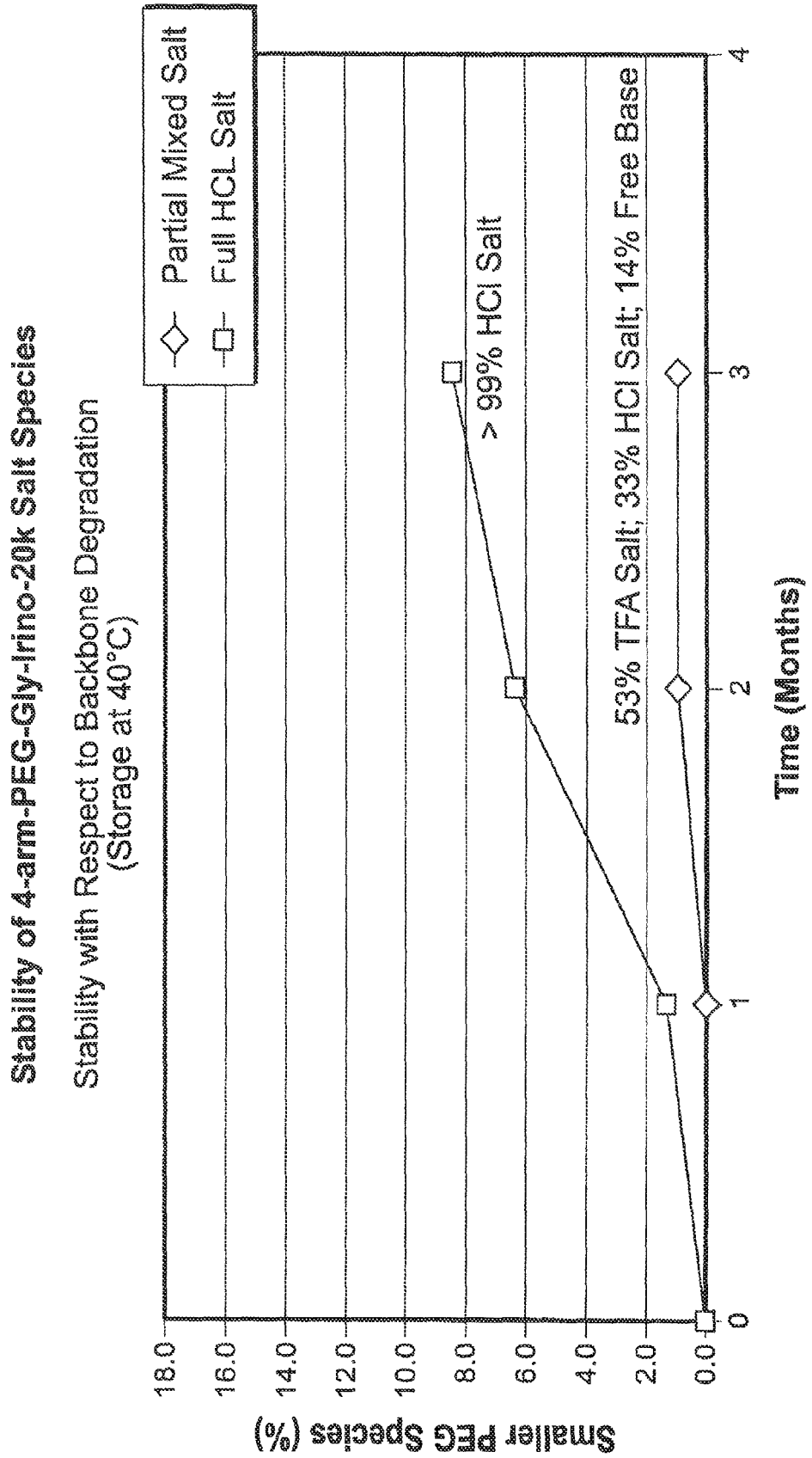
FIG. 3 is a graph illustrating the increase over time in small PEG species (PEG degradation products) in samples of 4-arm-PEG-Gly-Irino-20K stored at 40° C. and 75% relative humidity, as described in detail in Example 3. Samples tested correspond to product containing >99% HCl salt (<1% free base, squares) and product containing 86% total salts (14% free base, diamonds).

Additionally, as illustrated in FIG. 3, product rich in the hydrochloride salt appears to be more susceptible to cleavage of the water-soluble polymer backbone than the mixed salt form containing a measurable amount of free base. Indeed, decomposition of the mixed salt conjugate appears to be attributable primarily to hydrolytic release of drug rather than cleavage of the polymer backbone. Such backbone decomposition appears, however, to be relevant only under accelerated stress conditions.

Since the two modes of decomposition observed seem to show opposite trends with respect to stability or resistance to degradation versus salt/free base content, this may (but does not necessarily) indicate a preferred region of salt composition that possesses a greater overall stability than either extremes of full salt or full free base. Moreover, based upon preliminary studies, the mixed salt appears to possess somewhat greater stability than either the free base or hydrochloride salt form, thus indicating its unexpected superiority over any of the more traditional pure base or single salt forms thereof.

Further, mixed salt forms of the conjugate are prepared in high lot-to-lot consistency—that is to say, having relatively consistent molar ratios of trifluoroacetate, halide (or other suitable inorganic acid anion) and free base in the final conjugate product. As can be seen in Table 1 of Example 2, roughly 50 mole percent of drug basic nitrogen groups are associated with trifluoroacetic acid. This mole percentage is fairly consistently observed from lot-to-lot. Similarly, roughly 30 mole percent of conjugate drug amino (or other basic nitrogen) groups are fairly consistently associated with hydrochloric acid, i.e. provided as the HCl salt. It follows that the free base form of drug amino (or other basic nitrogen) groups in the conjugate are also stably and reproducibly prepared. Turning to the results provided in Example 6, based upon a slightly revised manufacturing method, it can be seen that despite differences in the actual relative molar amounts of protonated and unprotonated species, and within the protonated species, TFA versus hydrochloride salt, mixed acid salts were reproducibly prepared.

These collective results indicate the unexpected advantages of a partial mixed salt of a water-soluble polymer-active agent conjugate (in one embodiment, 4-arm-PEG-Gly-Irino-20K) over free base alone or either salt in the absence of the other. The mixed salt appears to have greater stability than either the free base or hydrochloride salt, thus indicating its seeming advantages over either of the more customary pure base or pure salt forms thereof.

Mixed Salts Conjugates—Methods for Forming

A mixed acid salt of a water soluble polymer conjugate can be readily prepared from commercially available starting materials in view of the guidance presented herein, coupled with what is known in the art. As described above, the mixed salt polymer-active agent conjugate comprises a water-soluble polymer covalently attached to one or more active agent molecules each possessing one or more basic nitrogen atoms, such as an amino group, when in conjugated form. Amine groups in the resulting conjugate may be primary, secondary, or tertiary amino groups.

Linear, branched, and multi-arm water-soluble polymer reagents are available from a number of commercial sources as described above. Alternatively. PEG reagents such as a multi-armed reactive PEG polymer may be synthetically prepared as described herein.

The partial mixed acid salt can be formed using known chemical coupling techniques for covalent attachment of activated polymers, such as an activated PEG, to a biologically active agent (See, for example, *POLY(ETHYLENE GLYCOL) CHEMISTRY AND BIOLOGICAL APPLICATIONS*, American Chemical Society, Washington, D.C. (1997); and U.S. Patent Publication Nos. 2009/0074704 and 2006/0239960). Selection of suitable functional groups, linkers, protecting groups, and the like to achieve a mixed acid salt in accordance with the invention, will depend, in part, on the functional groups on the active agent and on the polymer starting material and will be apparent to one skilled in the art, based upon the content of the present disclosure. In view of certain features of the partial mixed acid salt, the method comprises provision of an amine—(or other basic nitrogen)—containing active agent in the form of an inorganic acid addition salt, and a trifluoroacetic acid treatment step. Alternatively, the conjugate product or an intermediate in the synthetic pathway can be reacted with an inorganic acid to form an inorganic acid addition salt at a later stage in the process, to thereby introduce a second counterion (in addition to trifluoroacetate) into the reaction. Reference to an "active agent" in the context of the synthetic method is meant to encompass an active agent optionally modified to possess a linker covalently attached thereto, to facilitate attachment to the water-soluble polymer.

Generally, the method comprises the steps of (i) deprotecting an inorganic acid salt of an amine—(or other basic nitrogen)—containing active agent in protected form by treatment with trifluoroacetic acid (TFA) to form a deprotected mixed acid salt, (ii) coupling the deprotected inorganic acid salt of step (i) with a water-soluble polymer reagent in the presence of a base to form a polymer-active agent conjugate, and (iii) recovering the polymer active agent conjugate. The resulting polymer-active agent conjugate composition is characterized by having the one or more amino (or other basic nitrogen-containing) groups present in a combination of free base, acid salt, and TFA salt form. The product therefore comprises both inorganic acid salt and trifluoroacetate salt, as well as a proportion of basic groups in the conjugate that are in unprotonated or free base form. Thus, the combined molar amounts of inorganic acid salt and trifluoroacetic acid salt are less than the total number of basic amino or other nitrogens contained in the conjugate product.

In turning now to one of the preferred classes of active agents, the camptothecins, since the 20-hydroxyl group of compounds within the camptothecin family is sterically hindered, a single step conjugation reaction is difficult to accomplish in significant yields. As a result, a preferred method is to react the 20-hydroxyl group of the bioactive starting material, e.g., irinotecan hydrochloride, with a short linker or spacer moiety carrying a functional group suitable for reaction with a water-soluble polymer. Such an approach is applicable to many small molecules, particularly those having a site of covalent attachment that is inaccessible to an incoming reactive polymer. Preferred linkers for reaction with a hydroxyl group to form an ester linkage include t-BOC-glycine or other amino acids such as alanine, glycine, isoleucine, leucine, phenylalanine, and valine having a protected amino group and an available carboxylic acid group (See Zalipsky et al., "Attachment of Drugs to Polyethylene Glycols", *Eur. Polym. J.*, Vol. 19. No. 12, pp. 1177-1183 (1983)). Other spacer or linker moieties having an available carboxylic acid group or other functional group reactive with a hydroxyl group and having a protected amino group can also be used in lieu of the amino acids described above.

Typical labile protecting groups include t-BOC and FMOC (9-flourenylmethloxycarbonyl). t-BOC is stable at room temperature and easily removed with dilute solutions of trifluoroacetic acid and dichloromethane. FMOC is a base labile protecting group that is easily removed by concentrated solutions of amines (usually 20-55% piperidine in N-methylpyrrolidone).

In the instant example, the carboxyl group of N-protected glycine reacts with the 20-hydroxyl group of irinotecan hydrochloride (or other suitable camptothecin, such as 7-ethyl-10-hydroxy-camptothecin, or any other active agent) in the presence of a coupling agent (e.g., dicyclohexylcarbodiimide (DCC)) and a base catalyst (e.g., dimethylaminopyridine (DMAP) or other suitable base) to provide N-protected linker modified active agent. e.g., t-Boc-glycine-irinotecan hydrochloride. Although hydrochloride is exemplified, other inorganic acid salts may be used. Preferably, each reaction step is conducted under an inert atmosphere.

In a subsequent step, the amino protecting group, t-BOC (N-tert-butoxycarbonyl), is removed by treatment with trifluoroacetic acid (TFA) under suitable reaction conditions. It is in this step that trifluoroacetic acid is typically introduced into the reaction mixture. The product is linker modified active agent, e.g., 20-glycine-irinotecan TFA/HCl. Illustrative reaction conditions are described in Example 1, and may be further optimized by routine optimization by one of skill in the art. Optionally, the molar amounts of inorganic acid and trifluoroacetic acid in the decoupled product are determined by a suitable analytical method such as HPLC or ion chromatography, to allow greater precision and product consistency in the coupling step.

Deprotected active agent (optionally linker modified), e.g., 20-glycine-irinotecan TFA/HCl, is then coupled to a desired polymer reagent, e.g., 4-arm pentaerythritolyl-PEG-succinimide (or any other similarly activated ester counterpart) in the presence of a coupling agent (e.g., hydroxybenzyltriazole (HOBT)) and a base (e.g., DMAP, trimethyl amine, triethyl amine, etc.), to form the desired conjugate. In one embodiment of the method, the amount of base added in the conjugation step is in a range of approximately 1.0 to 2.0 times, or from about 1.0 to 1.5 times, or from about 1.0 to 1.05 times, the sum of the moles of TFA and the moles of inorganic acid determined for the starting material, in this case, 20-glycine-irinotecan TFA/HCl. By virtue of adjusting the amount of base to the acid salt content of the 20-glycine-irinotecan TFA/HCl, a relatively consistent ratio of TFA, inorganic acid (e.g., HCl), and base is maintained in the coupling step, to thereby form a partial mixed acid salt conjugate having a consistently narrow range of TFA and inorganic acid contents. Preferably, the resulting partial mixed acid salt is reproducibly prepared such that the relative molar amounts of inorganic addition salt, trifluoroacetic acid salt, and free base in the conjugate composition vary by no more than about 25%, and even more preferably by no more than about 15%, from batch to batch. For the purposes of making such determination, the foregoing measure of consistency is determined over at least five batches (e.g. from 5 to 7), where failed batches that are clearly outliers are excluded from the calculation.

Although the conjugation step is conducted in the presence of excess base, it is surprising to discover that the resulting conjugate is stably formed as a partial mixed acid salt, i.e., such that a significant amount of basic amino or other nitrogen containing groups in the conjugate are protonated rather than being in free base form. Reaction yields for the coupling reaction are typically high, greater than about 90% (e.g., about 95% on average).

The partial mixed acid salt conjugate is recovered. e.g., by precipitation with ether (e.g., methyl tert-butyl ether, diethyl ether) or other suitable solvent. The product may be further purified by any suitable method. Methods of purification and isolation include precipitation followed by filtration and drying, as well as chromatography. Suitable chromatographic methods include gel filtration chromatography, ion exchange chromatography, and Biotage Flash chromatography. One preferred method of purification is recrystallization. For example, the partial mixed acid salt is dissolved in a suitable single or mixed solvent system (e.g., isopropanol/methanol), and then allowed to crystallize. Recrystallization may be conducted multiple times, and the crystals may also be washed with a suitable solvent in which they are insoluble or only slightly soluble (e.g. methyl tert-butyl ether or methyl-tert-butyl ether/methanol). The purified product may optionally be further air or vacuum dried. Even upon repeated purification, the product is typically recovered as a mixed acid salt rather than as the free base. Even upon additional treatment with base, the conjugate remained in the form of a partial mixed acid salt having the features described herein.

The resulting conjugate is a partial mixed salt, i.e., where certain of the basic nitrogen atoms are in neutral or free base form and other basic nitrogen atoms, e.g., amino groups, are protonated. The protonated amine groups are in the form of acid salts with differing anions, one anion corresponding to the conjugate base of an inorganic acid, the other anion being trifluoroacetate (or the conjugate base of an organic acid as previously described). As used herein, a partial mixed salt refers to the bulk product rather than necessarily referring to individual molecular species contained within the bulk product. Thus, depending upon the particular conjugate structure, individual molecular species contained within the mixed salt may contain amine groups that are in free base and in protonated form as described above. Alternatively, a mixed salt may contain a mixture of molecular species (e.g. having all amine groups in free base form, having all amine groups in protonated form, either as the salt of an inorganic acid, the salt of trifluoroacetic acid or other suitable organic acid, or a mixture of both, various combinations of the foregoing, etc.), such that the features of the bulk product are as described herein. In the event that the conjugate is a polymer conjugate comprising only one active agent amine group, the mixed salt must necessarily be such that the bulk product is a mixture of molecular species to arrive at a mixed salt as described generally herein.

Preferably, the mixed acid salt product is stored under conditions suitable for protecting the product from exposure to any one or more of oxygen, moisture, and light. Any of a number of storage conditions or packaging protocols can be employed to suitably protect the acid salt product during storage. In one embodiment, the product is packaged under an inert atmosphere (e.g., argon or nitrogen) by placement in one or more polyethylene bags, and placed in an aluminum lined polyester heat scalable bag.

Representative mole percents of TFA salt, hydrochloric acid salt, and free base determined over a number of lots of 4-arm-PEG-Gly-Irino are summarized in Table 1 (Example 2) and Table 2 (Example 6). As can be seen, unexpectedly, even following treatment with base and repeated purification, the conjugate product is isolated not as a single non-protonated conjugate species, but rather as a mixed acid salt.

Mixed Salts—Pharmaceutical Compositions Containing Mixed Salt Conjugates

The partial mixed acid salt conjugates may be in the form of a pharmaceutical formulation or composition for either veterinary or human medical use. An illustrative formulation will typically comprise a partial mixed acid salt conjugate in combination with one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient/patient. The partial mixed acid salt conjugate is optionally contained in bulk or in unit dose form in a container or receptacle which includes packaging that protects the product from exposure to moisture and oxygen.

The pharmaceutical composition may include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed. Medical Economics, Montvale, N.J. (1998), and in "Handbook of Pharmaceutical Excipients", Third Ed., Ed. A. H. Kibbe, Pharmaceutical Press, 2000.

The mixed acid salt may be formulated in a composition suitable for oral, rectal, topical, nasal, ophthalmic, or parenteral (including intraperitoneal, intravenous, subcutaneous, or intramuscular injection) administration. The mixed acid salt composition may conveniently be presented in unit dosage form and may be prepared by any of the methods well known in the art of pharmacy. All methods include the step of bringing the mixed acid salt into association with a carrier that constitutes one or more accessory ingredients.

In one particular embodiment, the mixed acid salt, e.g., 4-arm-PEG-Gly-Irino-20K, is provided in lyophilized form in a sterile single use vial for use by injection. In one embodiment, the amount of conjugate product contained in the single use vial is the equivalent of a 100-mg dose of irinotecan. More particularly, the lyophilized composition includes 4-arm-PEG-Gly-Irino-20K combined with lactate buffer at pH 3.5. That is to say, the lyophilized composition is prepared by combining 4-arm-PEG-Gly-Irino-20K, e.g., in an amount equivalent to a 100-mg dose of irinotecan, with approximately 90 mg of lactic acid, and the pH of the solution adjusted to 3.5 by addition of either acid or base. The resulting solution is then lyophilized under sterile conditions, and the resulting powder is stored at −20° C. prior to use. Prior to intravenous infusion, the lyophilized composition is combined with a solution of dextrose, e.g., a 5% (w/w) solution of dextrose.

The amount of mixed acid salt (i.e. active agent) in the formulation will vary depending upon the specific active agent employed, its activity, the molecular weight of the conjugate, and other factors such as dosage form, target patient population, and other considerations, and will generally be readily determined by one skilled in the art. The amount of conjugate in the formulation will be that amount necessary to deliver a therapeutically effective amount of the compound, e.g., an alkaloid anticancer agent such as irinotecan or SN-38, to a patient in need thereof to achieve at least one of the therapeutic effects associated with the compound, e.g., for treatment of cancer. In practice, this will vary widely depending upon the particular conjugate, its activity, the severity of the condition to be treated, the patient population, the stability of the formulation, and the like. Compositions will generally contain anywhere from about 1% by weight to about 99% by weight conjugate, typically from about 2% to about 95% by weight conjugate, and more typically from about 5% to 85% by weight conjugate, and will also depend upon the relative amounts of excipients/additives contained in the composition. More specifically, the composition will typically contain at least about one of the following percentages of conjugate: 2%, 5%, 10%, 20%, 30%, 40%. 50%, 60%, or more by weight.

Compositions suitable for oral administration may be provided as discrete units such as capsules, cachets, tablets, lozenges, and the like, each containing a predetermined amount of the conjugate as a powder or granules; or a suspension in an aqueous liquor or non-aqueous liquid such as a syrup, an elixir, an emulsion, a draught, and the like.

Formulations suitable for parenteral administration conveniently comprise a sterile aqueous preparation of the mixed acid salt conjugate, which can be formulated to be isotonic with the blood of the recipient.

Nasal spray formulations comprise purified aqueous solutions of the multi-armed polymer conjugate with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the multi-armed polymer conjugate dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol, e.g., by inhalation. These formulations comprise a solution or suspension of the desired multi-armed polymer conjugate or a salt thereof. The desired formulation may be placed in a small chamber and nebulized. Nebulization may be accomplished by compressed air or by ultrasonic energy to form a plurality of liquid droplets or solid particles comprising the conjugates or salts thereof.

Mixed Salts—Methods of Using Mixed Salt Conjugates

The mixed acid salts described herein can be used to treat or prevent any condition responsive to the unmodified active agent in any animal, particularly in mammals, including humans. One representative mixed acid salt, 4-arm-pentaerythritolyl-PEG-glycine-irinotecan, comprising the anticancer agent, irinotecan, is particularly useful in treating various types of cancer.

The partial mixed acid salts conjugates, in particular, those where the small molecule drug is an anticancer agent such as a camptothecin compound as described herein (e.g., irinotecan or 7-ethyl-10-hydroxy-camptothecin) or other oncolytic, are useful in treating solid type tumors such as breast cancer, ovarian cancer, colon cancer, gastric cancer, malignant melanoma, small cell lung cancer, non-small cell lung cancer, thyroid cancers, kidney cancer, cancer of the bile duct, brain cancer, cervical cancer, maxillary sinus cancer, bladder cancer, esophageal cancer. Hodgkin's disease, adrenocortical cancer, and the like. Additional cancers treatable with the mixed acid salt include lymphomas, leukemias, rhabdomyosarcoma, neuroblastoma, and the like. As stated above, the mixed salt conjugates are particularly effective in targeting and accumulating in solid tumors. The mixed salt conjugates are also useful in the treatment of HIV and other viruses.

Representative conjugates such as 4-arm-pentaerythritolyl-PEG-glycine-irinotecan have also been shown to be particularly advantageous when used to treat patients having cancers shown to be refractory to treatment with one or more anticancer agents.

Methods of treatment comprise administering to a mammal in need thereof a therapeutically effective amount of a partial mixed acid salt composition or formulation as described herein.

Additional methods include treatment of (i) metastatic breast cancer that is resistant to anthracycline and/or taxane based therapies, (ii) platinum-resistant ovarian cancer, (iii) metastatic cervical cancer, and (iv) colorectal cancer in patients with K-Ras mutated gene status by administering a partial mixed acid salt composition.

In treating metastatic breast cancer, a mixed acid salt of a conjugate such as 4-arm-pentaerythritolyl-PEG-glycine-irinotecan as provided herein is administered to a patient with locally advanced metastatic breast cancer at a therapeutically effective amount, where the patient has had no more than two prior (unsuccessful) treatments with anthracycline and/or taxane based chemotherapeutics.

For treating platinum-resistant ovarian cancer, a composition as provided herein is administered to a patient with locally advanced or metastatic ovarian cancer at a therapeutically effective amount, where the patient has shown tumor progression during platinum-based therapy, with a progression-free interval of less than six months.

In yet another approach, a mixed acid salt (e.g., such as that in Example 1) is administered to a subject with locally advanced colorectal cancer, where the colorectal tumor(s) has a K-Ras oncogene mutation (K-Ras mutant types) such that the tumor does not respond to EGFR-inhibitors, such as cetuximab. Subjects are those having failed one prior 5-FU containing therapy, and are also irinotecan naïve.

A therapeutically effective dosage amount of any specific mixed acid salt will vary from conjugate to conjugate, patient to patient, and will depend upon factors such as the condition of the patient, the activity of the particular active agent employed, the type of cancer, and the route of delivery.

For camptothecin-type active agents such as irinotecan or 7-ethyl-10-hydroxy-camptothecin, dosages from about 0.5 to about 100 mg camptothecin/kg body weight, preferably from about 10.0 to about 60 mg/kg, are preferred. When administered conjointly with other pharmaceutically active agents, even less of the mixed acid salt may be therapeutically effective. For administration of a mixed acid salt of irinotecan, the dosage amount of irinotecan will typically range from about 50 mg/m$^2$ to about 350 mg/m$^2$.

Methods of treatment also include administering a therapeutically effective amount of a mixed acid salt composition or formulation as described herein (e.g., where the active agent is a camptothecin type molecule) in conjunction with a second anticancer agent. Preferably, such camptothecin-based conjugates, of course, in the form of a mixed acid salt, are administered in combination with 5-fluorouracil and folinic acid as described in U.S. Pat. No. 6,403,569.

The mixed acid salt compositions may be administered once or several times a day, preferably once a day or less. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

EXPERIMENTAL

The practice of the invention will employ, unless otherwise indicated, conventional techniques of organic synthesis and the like, which are within the skill of the art. Such techniques are fully described in the literature. Reagents and materials are commercially available unless specifically stated to the contrary. See, for example, M. B. Smith and J. March, *March's Advanced Organic Chemistry: Reactions Mechanisms and Structure,* 6th Ed. (New York: Wiley-Interscience, 2007), supra, and Comprehensive Organic Functional Group Transformations II, Volumes 1-7, Second Ed.: A Comprehensive Review of the Synthetic Literature 1995-2003 (Organic Chemistry Series), Eds. Katritsky, A. R. et al. Elsevier Science.

In the following examples, efforts have been made to ensure accuracy with respect to numbers used (e.g., amounts, temperatures, etc.) but some experimental error and deviation should be accounted for. Unless indicated otherwise, temperature is in degrees C and pressure is at or near atmospheric pressure at sea level.

The following examples illustrate certain aspects and advantages of the present invention, however, the present invention is in no way considered to be limited to the particular embodiments described below.

ABBREVIATIONS

Ar argon
CM carboxymethyl or carboxymethylene (—CH$_2$COOH)
DCC 1,3-dicyclohexylcarbodiimide
DCM dichloromethane
DMAP 4-(N,N-dimethylamino)pyridine
GLY glycine
HCl hydrochloric acid
RP-HPLC reverse-phase high performance liquid chromatography
IPA isopropyl alcohol
IRT irinotecan
IPC ion pair chromatography
MeOH methanol
MTBE methyl tert-butyl ether
MW molecular weight
NMR nuclear magnetic resonance
PEG polyethylene glycol
RT room temperature
SCM succinimidylcarboxymethyl (—CH$_2$—COO—N-succinimidyl)
TEA triethylamine
TFA trifluoroacetic acid
THF tetrahydrofuran Materials and Methods Pentaerythritolyl-based 4-ARM-PEG$_{20K}$-OH was obtained from NOF Corporation (Japan). 4-ARM-PEG$_{20K}$-OH possesses the following structure (wherein each n is about 113): C—(CH$_2$O—(CH$_2$CH$_2$O)$_n$H$_4$.

All $^1$HNMR data was generated by a 300 or 400 MHz NMR spectrometer manufactured by Bruker.

EXAMPLE 1

Preparation 1

Preparation of Pentaerythritolyl-4-Arm-(Peg-1-Methylene-2Oxo-Vinylamino Acetate Linked-Irinotecan)-20K "4-Arm-Peg-Gly-Irino-20K Mixed Acid Salt Reaction Scheme:

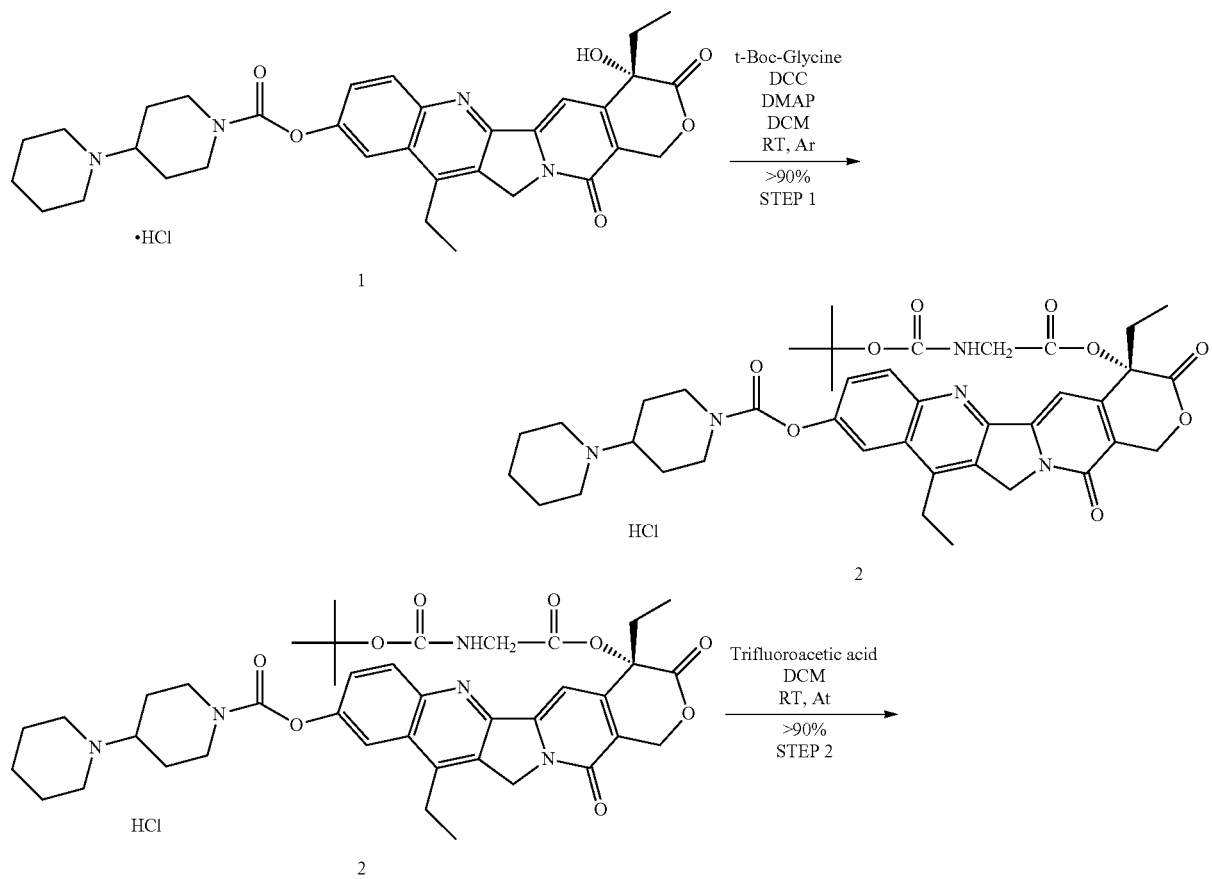

-continued
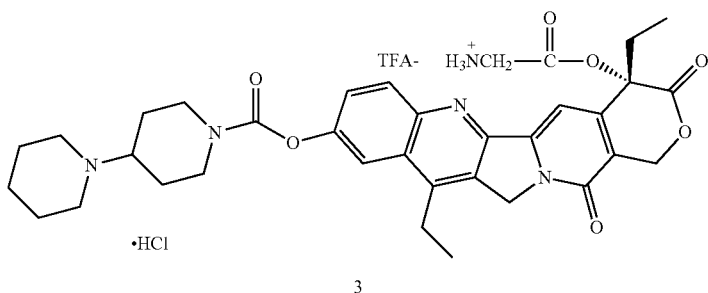
3
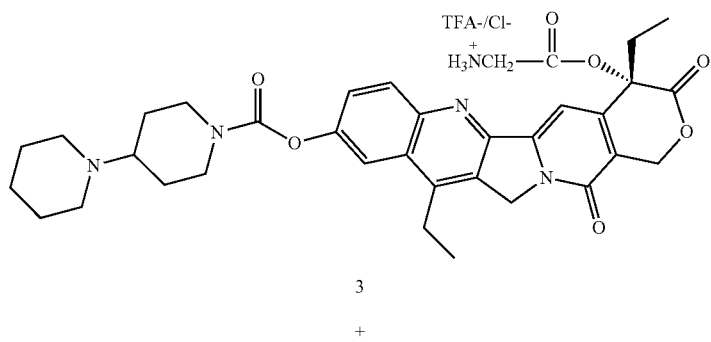
3
+
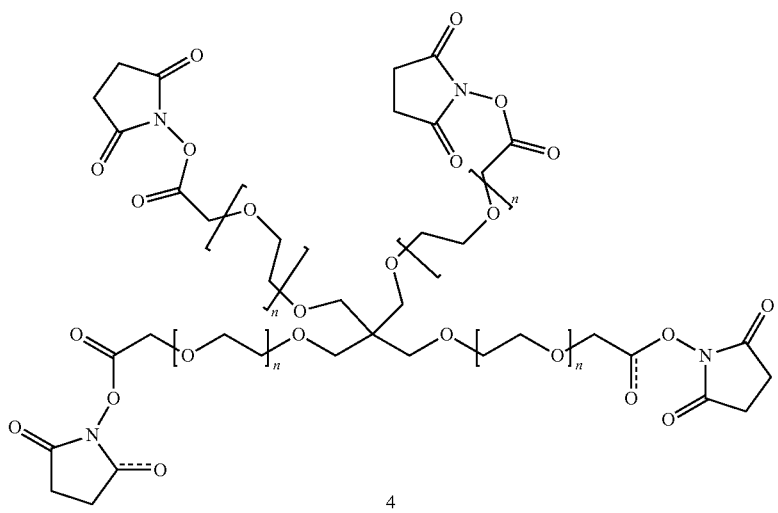
4
TEA
DCM/DMF
RT, Ar
Isolate from MeOH/IPA (x3)
>90%
STEP 3

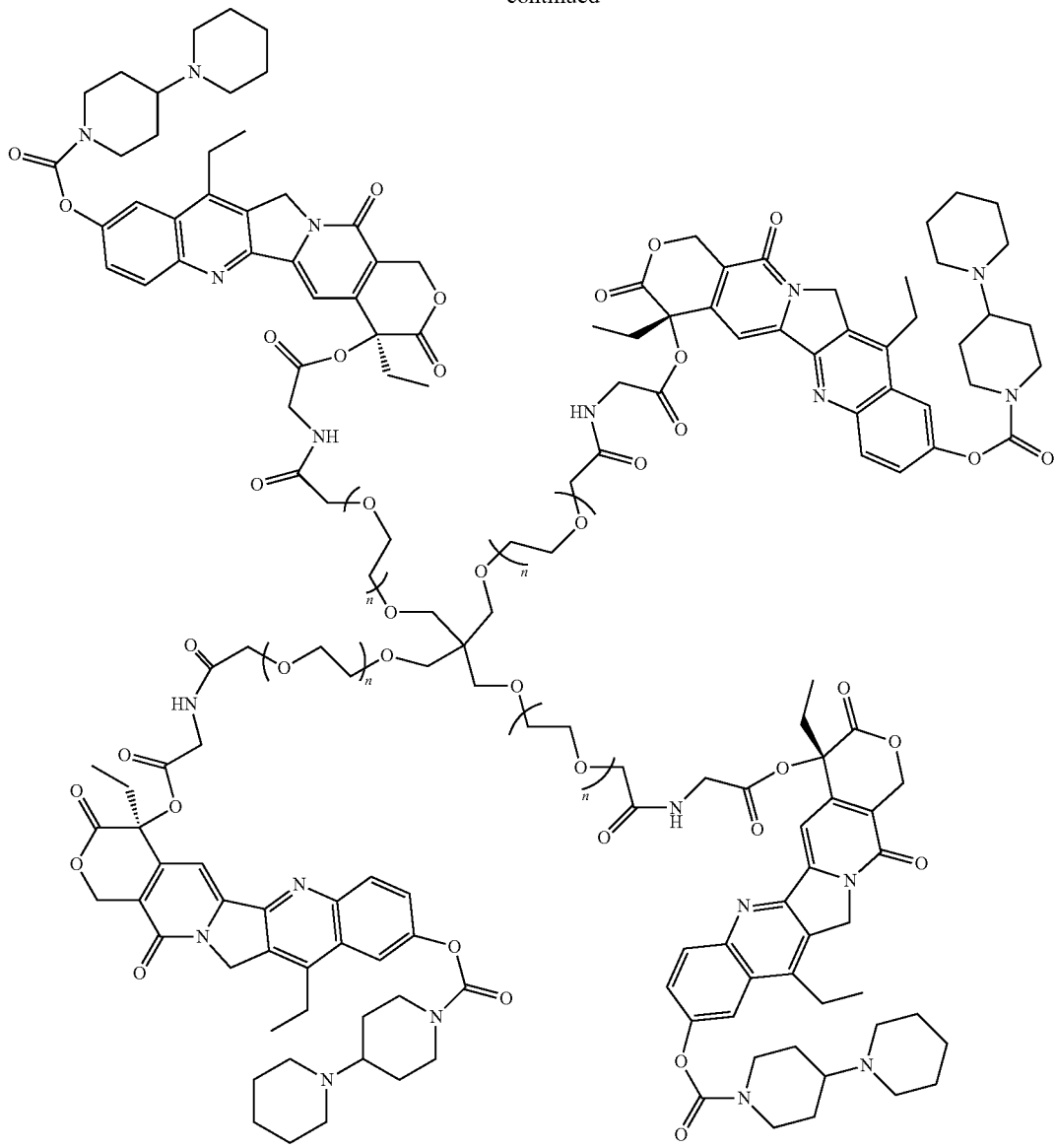

(*n* = ~133/arm)
TFA/HCl
5

All solvents used in synthesis were anhydrous.

Step 1. Conjugation of t-boc-glycine to Irinotecan.HCl Salt (>95% Yield)

Irinotecan.HCl.trihydrate (1 mole or 677 g) and DMF (10 L) were charged into a distiller at 60° C. Upon dissolution of the irinotecan.HCl.trihydrate in DMF, full vacuum was slowly applied in order to remove water from the irinotecan.HCl.trihydrate by azeotropic distillation at 60° C. Upon solids formation from the residual DMF, heptane (up to 60 L) was charged into the distiller to remove residual DMF at 40-50° C. Upon removal of heptane by visual inspection, the azeotropic distillation was stopped and the solid (irinotecan.HCl) was allowed to cool to 17±2° C. For the coupling reaction, t-boc-glycine (1.2 mole), 4-DMAP (0.1 mole) dissolved in DCM (1 L), and DCM (19 L) were charged into the distiller. Once the mixture was visually well dispersed, melted DCC (1.5 mole) was added and reaction was allowed to proceed. The reaction was carried out under an argon or nitrogen blanket, with sufficient mixing and pot temperature at 17±2° C.

After a 2-4 hour reaction time, a sample was withdrawn to measure residual irinotecan (IRT) peak area percent by chromatography. Residual irinotecan was determined to be present in an amount of no more than 5%. DCU formed during the coupling reaction was removed by filtration, and washed with DCM. The resulting filtrates containing crude t-boc-glycine-irinotecan-HCl salt were combined and concentrated below 45° C. under vacuum to remove DCM. When approximately 75% of its initial volume was removed by distillation, IPA was then added to the concentrate to reach the initial volume, and the mixture further distilled until the condensate volume reached about 25% of its initial volume. The resulting clear solution was cooled to room temperature, followed by its addition to heptane with mixing. The mixture was mixed for an additional 0.5 to 1 hour, during which time a precipitate formed. The precipitate was drained and filtered to obtain a wet cake, and then washed with heptane (up to 6 L). The wet cake was vacuum-dried to yield t-boc-glycine-irinotecan powder for use in Step 2. Yield>95%.

Step 2. Deprotection of t-boc-glycine-Irinotecan

The t-boc-glycine-irinotecan (1 mole) from Step 1 was dissolved in DCM with agitation to form a visually homogeneous solution. To this solution was added TFA (15.8 mole) over a period of 5 to 10 minutes and the resulting solution stirred for about 2 hours. Residual starting material was measured by RP-HPLC and determined to be less than about 5%. Acetonitrile was then added to the reaction solution to form a visually homogeneous solution at RT. This solution was then added to MTBE (46.8 kg) being sufficiently agitated at 35° C. to promote crystallization. Optionally to reduce MTBE use. DCM in the reaction solution was replaced with acetonitrile by distillation at 15 to 40° C. After the solvent swap, the product-containing solution was added into approximately 50% less volume of MTBE (23 kg) being sufficiently agitated at the crystallization temperature (35° C.). Mixing was continued for a half to one hour. The resulting solid was filtered and the cake washed with MTBE.

The wet cake was vacuum-dried to yield the glycine-irinotecan salt powder for use in Step 3. Trifluoroacetate and chloride content of the product was determined by ion chromatography with a conductivity detector. (Yield>95%).

Step 3. PEGylation of Glycine-irinotecan using 4-arm-PEG-CM-SCM

The glycine-irinotecan-TFA/HCl salt powder from Step 2 was added to a reaction vessel to which was added DCM (approx. 23 L). The mixture was agitated for approximately 10 to 30 minutes to allow the glycine-irinotecan.TFA/HCl salt to disperse in DCM. Triethyl amine (approx. 1.05 moles (HCl+TFA) moles in glycine-irinotecan TFA/HCl salt powder) was then added slowly, at a rate which maintained the pot temperature at 24° C. or below. The resulting mixture was agitated for 10 to 30 minutes to allow dissolution of the GLY-IRT (glycine-modified irinotecan) free base.

Approximately 80% of the total quantity (6.4 kg) of 4-arm PEG-SCM was added to the reaction vessel over a course of up to 30 minutes. After dissolution of the PEG reagent, reaction progress was monitored by IPC. (In the event that the amount of non-conjugated GLY-IRT was greater than 5% when the reaction appeared to have reached a plateau, the remaining 20% of 4-arm PEG SCM was then added to the reaction vessel, and the reaction progress monitored until a constant value of unreacted GLY-IRT was observed).

Crude product was precipitated by adding the reaction solution into MTBE (113.6 L) agitated at room temperature over a period of from 1-1.5 hours, followed by stirring. The resulting mixture was transferred into a filter-drier with an agitator to remove the mother liquor. The precipitate (crude product) was partially vacuum-dried at approximately at 10 to 25° C. with minimum intermittent stirring.

Crude product was then placed into a reaction vessel, to which was added IPA (72 L) and MeOH (8 L), followed by agitation for up to 30 minutes. Heat was applied to achieve visually complete dissolution (a clear solution) at 50° C. pot temperature, followed by agitation for 30 to 60 minutes. The solution was then cooled to 37° C. held there for several hours, followed by cooling to 20° C. The mixture was transferred into an agitated filter dryer, and filtered to remove mother liquor to form a cake on a filter. The cake was washed with 70% MTBE in IPA and 30% MeOH and partially vacuum-dried. This procedure was repeated two additional times, with the exception that, prior to cooling, the clear IPA/MeOH solution containing 4-arm PEG-Gly-IRT was filtered using an in-line filter (1 um) at 50° C. to remove any potential particulates in the last (3rd) crystallization.

Three representative samples were taken from the washed wet cake, and NHS levels were measured using NMR. The wet cake was vacuum-dried.

The product ("API") was packaged into double bags sealed under an inert atmosphere, and stored at −20° C. without exposure to light. Product yield was approximately 95%.

EXAMPLE 2

Characterization of "4-Arm-PEG-Gly-Irino-20K" Product as a Mixed Salt

The product from Example 1 was analyzed by ion chromatography (IC analysis). See Table 1 below for IC analytical results for various product lots of 4-arm-PEG-Gly-Irino-20K.

TABLE 1

| | Mole Percent of Irinotecan bound to PEG | | |
|---|---|---|---|
| LOT NO. | TFA SALT | HCl SALT | FREE BASE |
| 010 | 59 | 36 | 5 (low) |
| 020 | 64 (high) | 30 | 6 |
| 030 | 27 (low) | 24 | 49 (high) |
| 040 | 53 | 26 | 21 |
| 050 | 54 | 26 | 20 |
| 060 | 57 | 28 | 15 |
| 070 | 53 | 33 | 14 |
| 080 | 53 | 27 | 20 |
| 090 | 44 | 19 | 36 |
| 100 | 33 | 41 | 26 |
| Average of last 7 lots | 50 | 29 | 22 |

Based upon the IC results provided in Table 1, it can be seen that the product formed in Example 1. 4-arm-PEG-Gly-Irino-20K, is a partial mixed salt of approximately 50 mole percent TFA salt, 30 mole percent HCl salt, and 20 mole percent free base, based upon conjugated irinotecan molecules in the product. The mixture of salts was observed even after repeated (1-3) recrystallizations of the product. In the various product lots analyzed above, it can be seen that about 35-65 mole percent of the irinotecan molecules in the composition are protonated as the TFA salt, about 25-40 mole percent of the irinotecan molecules in the composition are protonated as the HCl salt, while the remaining 5-35 mole percent of the irinotecan is non-protonated (i.e., as the free base).

The generalized structure of the product is shown below, where the irinotecan moieties are shown in free base form, and in association with HCl and TFA—as an indication of the mixed salt.

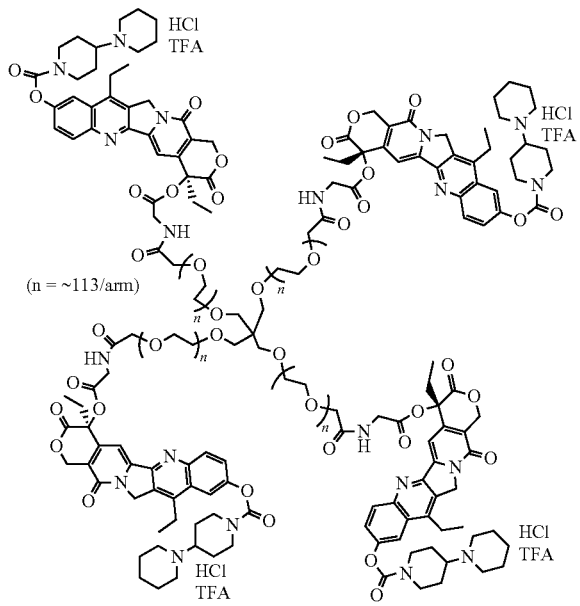

EXAMPLE 3

Stress Stability Studies of 4-Arm-PEG-Gly-Irino-20K

Stability studies were conducted in an attempt to evaluate the 4-arm-PEG-Gly-Irino-20K product composition. Compositions containing varying amounts of protonated irinotecan, as well as differing in the amount of TFA versus HCl salt were examined.

Stress Stability Studies

The product formed in Example 1. 4-arm-PEG-Gly-Irino-20K, compound 5, (approximately 1-2 g) was weighed into PEG PE 'whirl top' bags and placed into another 'whirl top' bag in order to simulate the API packaging conditions. In one study (results shown in FIG. 1), samples were placed in an environmental chamber at 25° C./60% RH for 4 weeks. In another study, samples were placed in an environmental chamber at 40° C./75% RH for up to several months (results shown in FIG. 2 and FIG. 3). Samples were taken and analyzed on a periodic basis over the course of the studies.

Results

The results of the studies are shown in FIG. 1, FIG. 2 and FIG. 3. In FIG. 1, 4-arm-PEG-Gly-Irino-20K peak area percents for samples stored at 25° C. and 60% relative humidity are plotted versus time. The data shown are for samples consisting of >99% HCl salt (<1% free base, triangles), 94% total salt (6% free base, squares), and 52% total salt (48% free base, circles). The slopes of the graphs indicate that as free base content increases, the stability of the product decreases. Under the stress conditions employed (i.e., 25° C. for up to 28 days), the drop in 4-arm-PEG-Gly-Irino-20K peak area correlated well with the increase in free irinotecan, indicating that the mode of decomposition is primarily via hydrolysis of the ester bond to release irinotecan. Based upon the results observed, it appears that a greater amount of free base in the product leads to decreased stability towards hydrolysis. Thus, product containing a greater degree of protonated irinotecan appears to have a greater stability against hydrolysis than product containing less protonated irinotecan (based upon mole percent).

FIG. 2 and FIG. 3 show another set of data obtained from the sample containing >99% HCl salt (<1% free base, squares) and a sample consisting of 86% total salts (14% free base, diamonds) that were stored at 40° C. and 75% relative humidity. FIG. 2 shows the increase in free irinotecan over 3 months for both samples. This data is consistent with the data from the previously described study (summarized in FIG. 1), which shows that product with a higher free base content is less stable with respect to hydrolysis. FIG. 3 shows the increase in smaller PEG species for the same samples over 3 months. The increase in smaller PEG species is indicative of decomposition of the PEG backbone to provide multiple PEG species. The data indicates that product corresponding to the HCl salt is more prone to PEG backbone decomposition than the mixed salt sample containing 14% free base. Thus, while not intending to be bound by theory, it appears that that while the partial mixed salt degrades primarily by hydrolytic release of drug, the hydrochloride salt appears to degrade by a different mechanism, i.e., degradation of the polymer backbone. Based upon these preliminary results, the partial mixed salt product appears to be preferred over the hydrochloride salt.

In summary, the two modes of decomposition observed exhibit opposite trends with respect to salt/free base content. Unexpectedly, these results suggest that there is a region of salt composition that may possess an overall stability that is enhanced over either of the traditional extremes of full salt and full free base. The results further indicate the unforeseen advantages of a partial mixed salt of 4-arm-PEG-Gly-Irino-20K over free base alone or either salt in the absence of the other. The mixed salt was shown to have greater stability than either the free base or hydrochloride salt, thus indicating its superiority over either of the more customary pure base or pure salt forms thereof.

EXAMPLE 4

Chirality Study

The chirality of carbon-20 of irinotecan in 4-arm-PEG-Gly-Irino-20K was determined.

As detailed in documentation from the vendor, the irinotecan hydrochloride starting material is optically active, with C-20 in its (S)-configuration. The C-20 position in irinotecan bears a tertiary alcohol, which is not readily ionizable, hence this site is not expected to racemize except under extreme (strongly acidic) conditions. To confirm the chirality at the C-20 in 4-arm-PEG-Gly-irino-20K, a chiral HPLC method was used to analyze irinotecan released from product via chemical hydrolysis.

Based upon the resulting chromatograms, no (R)-enantiomer was detected for the 4-arm-PEG-Gly-Irino-20K samples. Following hydrolysis, the irinotecan released from the conjugate was confirmed to be the (S)-configuration.

EXAMPLE 5

Hydrolysis Study

All PEGylated irinotecan species are considered as part of 4-arm-PEG(-Gly-Irino-20K; each specie cleanly hydrolyzes to produce irinotecan of >99% purity. Furthermore, the main, fully drug-loaded DS4 species (drug covalently attached on each of the four polymer arms) and the partially substituted species—DS3 (drug covalently attached on three polymer arms). DS2 (drug covalently attached on two of the polymer arms) and DS1 species (drug covalently attached on a single polymer arm)—all hydrolyze at the same rate to release free drug, irinotecan.

Experiments were performed to determine the fate of the irinotecan-containing PEG species in 4-arm-PEG-Gly-Irino-20K under transesterification ($K_2CO_3$ in $CH_3OH$, 20° C.) and aqueous hydrolysis (pH 10, 20° C.) conditions. The transesterification reaction was >99% complete after 45 minutes. The aqueous hydrolysis reaction was >99% complete within 24 hours. For both reaction types, control reactions using irinotecan were performed under identical conditions and some artifact peaks were observed. After adjustment for artifact peaks, in both cases, the irinotecans produced had chromatographic purities of >99%.

Figure 4:
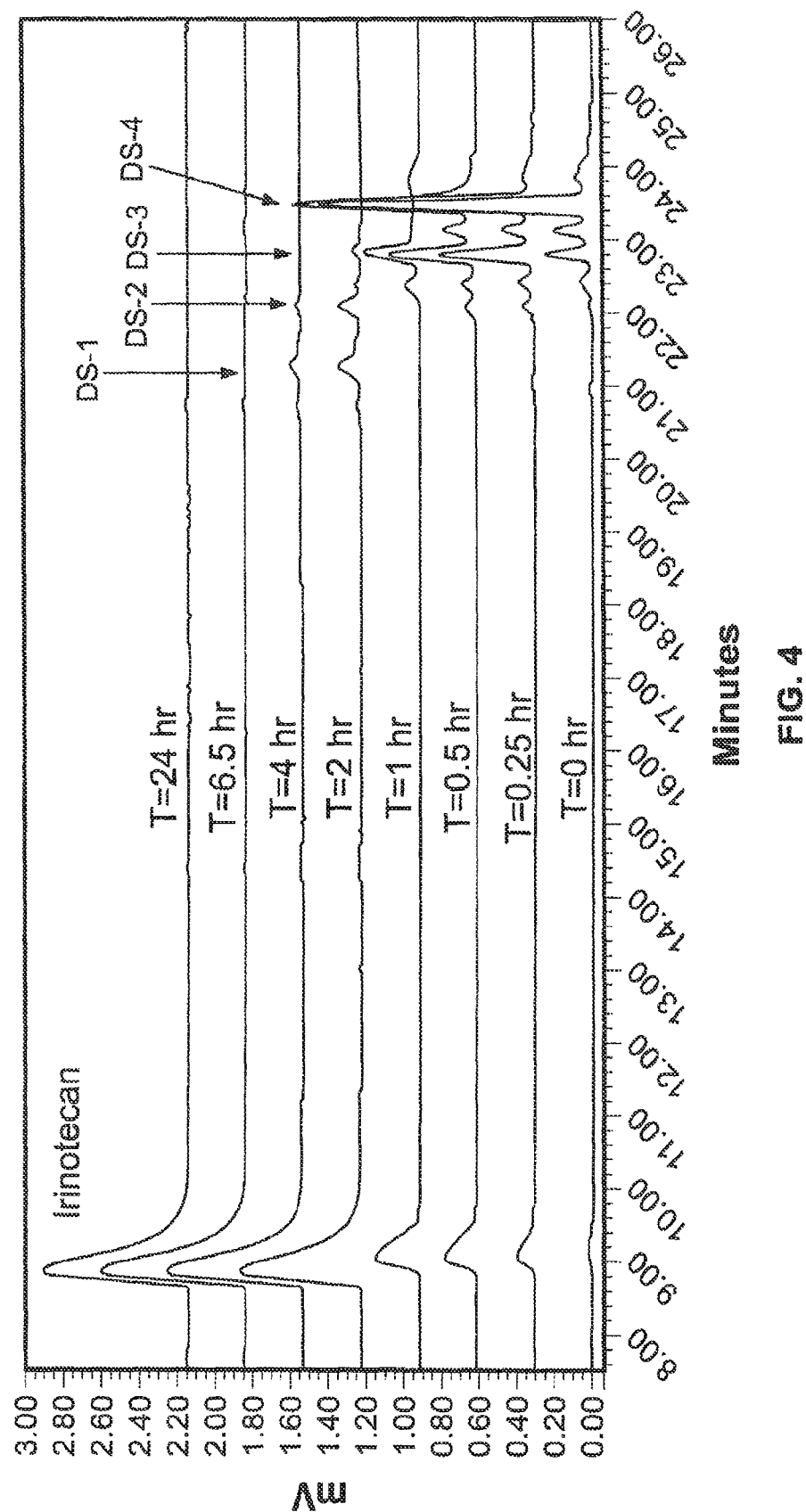
FIG. 4 is a compilation of overlays of chromatograms exhibiting release of irinotecan via hydrolysis from mono-(DS-1), di-(DS-2), tri-(DS-3) and tetra-irinotecan substituted (DS-4) 4-arm-PEG-Gly-Irino-20K as described in detail in Example 5.

Based upon these results, it was concluded that essentially all PEGylated species in 4-arm-PEG-Gly-Irino-20K release irinotecan. Overlays of the HPLCs taken over time from the aqueous hydrolysis reaction show the conversion of DS4 to DS3 to DS2 to DS1 to irinotecan. All of these species hydrolyze to release irinotecan. See FIG. 4 demonstrating release of irinotecan via hydrolysis from mono-, di-, tri- and tetra-substituted 4-arm-PEG-Gly-Irino-20K species.

Additional experiments were conducted to measure the rates of hydrolysis for the major component of 4-arm-PEG-Gly-Irino-20K, DS4, and its lesser substituted intermediates, DS3. DS2 and DS in aqueous buffer (pH 8.4) in the presence of porcine carboxypeptidase B and in human plasma. The hydrolysis in aqueous buffer (pH 8.4) in the presence of porcine carboxypeptidase B was an attempt to perform enzyme-based hydrolysis. The control experiment at pH 8.4 without the enzyme later showed that the hydrolysis was pH-driven, and thus primarily a chemical hydrolysis. The data were, nevertheless, valuable for comparison with the data obtained from the hydrolysis performed in human plasma. These experiments showed that the hydrolysis rates of the various components are not significantly different and compare favorably with theoretical predictions. Additional experiments measured the rates of hydrolysis for the major components (DS4, DS3, DS2 and DS1) of 4-arm-PEG-Gly-Irino-20K in human plasma. These experiments also show that the various components are hydrolyzed at the same rate and compare favorably with theoretical predictions.

Figure 5:
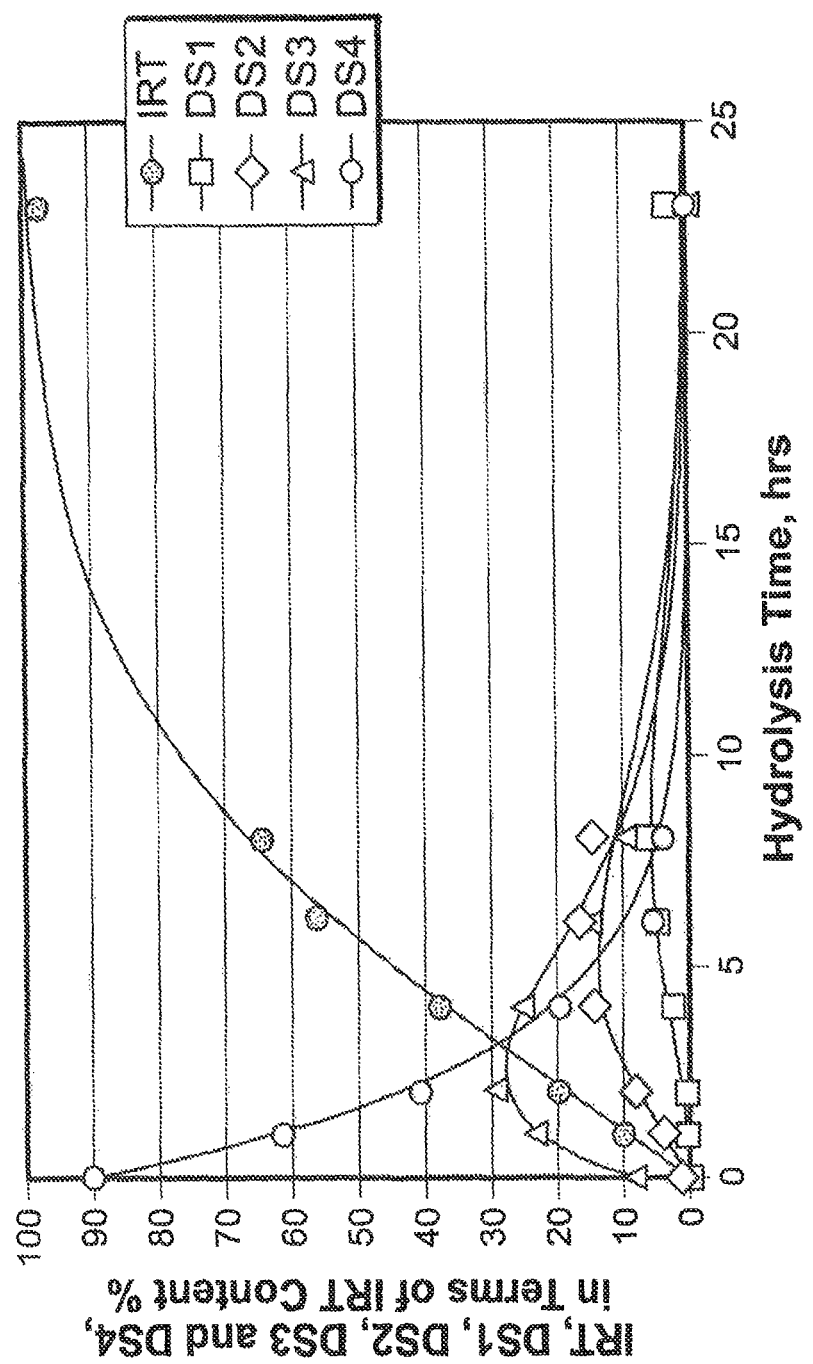
FIG. 5 is a graph illustrating the results of hydrolysis of various species of 4-arm-PEG-Gly-Irino-20K as described above in aqueous buffer at pH 8.4 in the presence of porcine carboxypeptidase B in comparison to hydrolysis kinetics modeling data as described in Example 5. For the kinetics model, the hydrolysis of all species was assumed to be $1^{st}$ order kinetics. The $1^{st}$ order reaction rate constant for disappearance of DS4 (0.36 hr$^{-1}$) was used to generate all curves.
Figure 6:
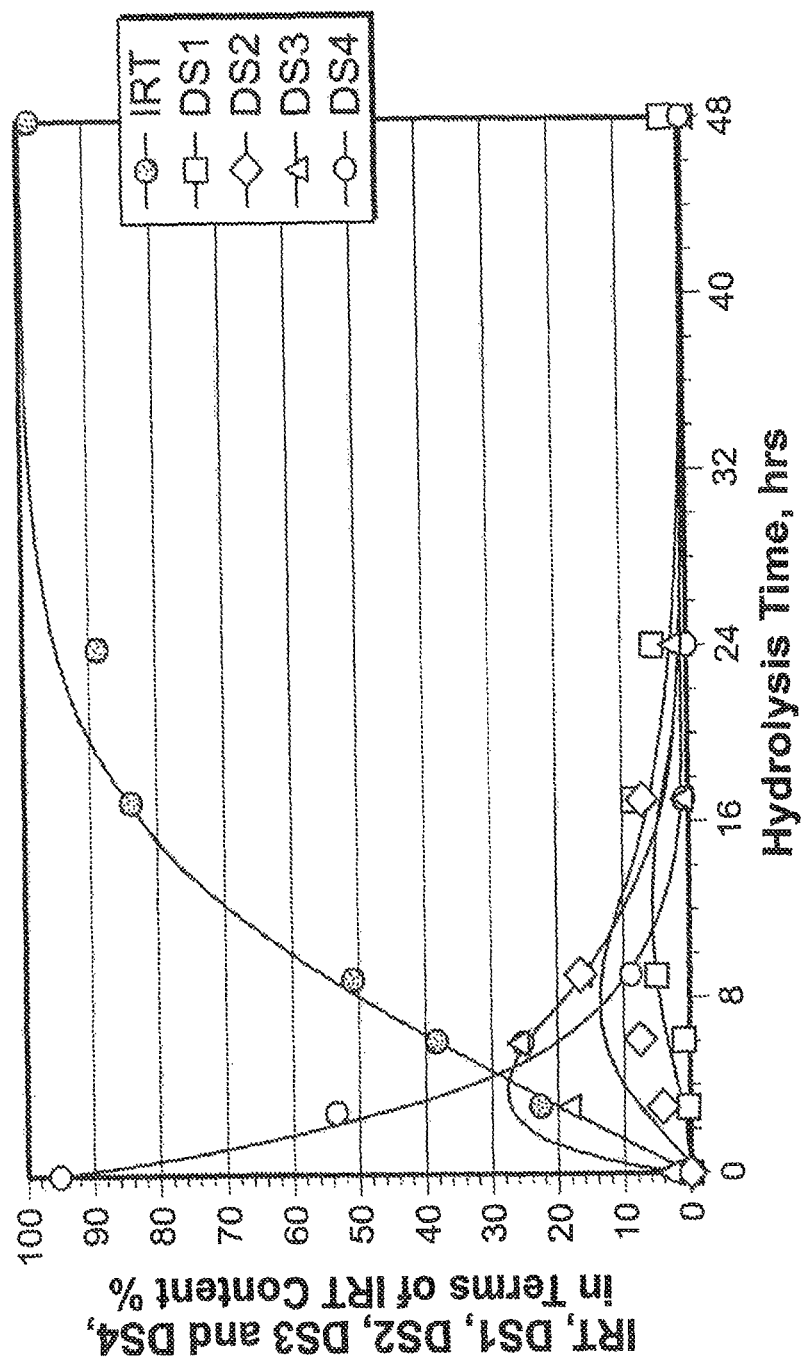
FIG. 6 is a graph illustrating the hydrolysis of various species of 4-arm-PEG-Gly-Irino-20K as described above in human plasma in comparison to hydrolysis kinetics modeling data. Details are provided in Example 5. For the kinetics model, the hydrolysis of all species was assumed to be $1^{st}$ order kinetics. The $1^{st}$ order reaction rate constant for disappearance of DS 4 (0.26 hr$^{-1}$) was used to generate all curves.

FIG. 5 and FIG. 6 present graphs which show the theoretical hydrolysis rates versus experimental data for the chemical hydrolysis (in the presence of enzyme) and plasma hydrolysis, respectively. In both cases, the theoretical predictions are based on identical rates for the hydrolysis of each species to produce the next-lower homologue plus free irinotecan (i.e., DS4>DS3>DS2>DS1).

EXAMPLE 6

Preparation 2

Preparation of Pentaerythritolyl-4-Arm-(PEG-1-Methylene-2 Oxo-Vinylamino Acetate Linked-Irinotecan)-20K "4-Arm-PEG-Gly-Irino-20K Mixed Acid Salt Step 1. Synthesis of Boc-Glycine-irinotecan Hydrochloride (Gly-IRT HCl)
Part 1: Drying of Irinotecan Hydrochloride Trihydrate ($IRT.HCl.3H_2O$)

$IRT.HCl.3H_2O$ (45.05 g, 66.52 mmol) was charged into a reactor. Anhydrous N,N-dimethylformamide (DMF) (666 mL, 14.7 mL/g of $IRT.HCl.3H_2O$, DMF water content NMT 300 ppm) was charged to the reactor. With slow agitation, the reactor was heated to 60° C. (jacket temperature). After the irinotecan (IRT) was fully dissolved (5-10 minutes), vacuum was slowly applied to reach 5-10 mbar and DMF was distilled off. When the volume of condensed distillate (DMF) reached 85-90% of the initial DMF charge, the vacuum was released. Heptane (1330 mL, 30.0 mL/g of $IRT.HCl.3H_2O$, water content NMT 50 ppm) was introduced into the reactor and the jacket temperature was lowered to 50° C. Heptane was vacuum distilled (100-150 mbar) until the volume of the distillate was about 90% of the initial charge of heptane. Two more cycles of heptane distillation were carried out (2×1330 mL heptane charge and distillation). A solvent phase sample was taken from the reactor and was analyzed for DMF content using GC to ensure a DMF content of less than 3% w/w. (In the event the residual DMF was >3.0% w/w, a fourth azeotropic distillation cycle would be performed). The resultant slurry was used for the coupling reaction (Part 2).

Part 2: Coupling Reaction: Preparation of Boc-Gly-IRT.HCl

Dichloromethane (1330 mL, 29.5 mL DCM/g IRT-HC-$3H_2O$) was charged into the reactor containing the slurry of dry IRT-HCl (1.0 equiv) in residual heptanes (the approximate mass ratio of residual heptanes to IRT.Hcl was 3) which was being stirred. The reaction contents were agitated for 15-30 minutes, and the batch temperature was maintained at 17° C. Boc-glycine (14.0 g, 79.91 mmol, 1.2 equiv) and DMAP (0.81 g, 6.63 mmol, 0.1 equiv) were charged, as solids, into the reactor. A DCM solution of DCC (1.5 equiv in 40 mL of dichloromethane) was prepared and added into the reactor over 15-30 min, and the resultant reaction mixture was stirred at 17° C. (batch temperature) for 2-3 hr. The reaction was monitored by HPLC to ensure completion. A pre-made quenching solution was charged into the reaction mixture to quench any remaining DCC. Briefly, the pre-made quenching solution is a pre-mixed solution of TFA and IPA in dichloromethane, prepared by mixing TFA (1.53 mL, 0.034 mL/g $IRT.HCl.3H_2O$) and IPA (3.05 mL, 0.068 m/g IRT-$HCl.3H_2O$) in DCM (15.3 mL, 0.34 ml/g IRT-HCl-$3H_2O$), and was added to the reactor V1 over 5-10 minutes when the conversion was at least 97%. The contents were agitated for additional 30-60 min to allow quenching. The DCU-containing reaction mixture was filtered through a 1 micron filter into another reactor. The reaction filtrate was distilled to ⅓ its volume under vacuum at 35 C. Isopropyl alcohol (IPA) (490.5 mL, 10.9 mL/g $IRT.HCl.3H_2O$) was added to the concentrated mixture and the mixture was stirred for 30-60 min at 50° C. (jacket temperature). The resulting homogeneous solution was concentrated by vacuum distillation to approximately 85% of the initial IPA charge volume and the resultant concentrate was cooled to 20° C. (jacket temperature). The reaction mixture in IPA was transferred over 60-80 min into heptane (1750 mL, 38.8 mL heptane/g $IRT.HCl.3H_2O$) at 20° C. The resultant slurry containing Boc-gly-IRT.HCl precipitate was stirred for an additional 60-90 minutes and the product was collected by filtration. The reaction flask was rinsed with heptane (2×490 mL, 20.0 mL Heptane/g IRT-HCl-$3H_2O$) and the product cake was washed with the rinse. The wet cake was dried at 20° C. to 25° C. under vacuum for a minimum of 12 hrs. Yield: 57.13 g (110%, high due to residual solvents)

Step 2. Synthesis of Glycine-Irinotecan Hydrochloride-Trifluoroacetate (Gly-IRT HCl-TFA) (Deprotection)

To an appropriately sized reactor was added dried Boc-gly-IRT-HCl (41.32 g, 52.5 mmol, from step 1) under an inert atmosphere. Anhydrous DCM (347 mL, 8.4 mL of DCM/g of Boc-gly-IRT-HCl) was added to the reactor and the contents were agitated at 17° C. until complete dissolution (15-30 min approximately). TFA (61.98 mL, 691.5 mmol, 1.5 mL/g of Boc-gly-IRT.HCl) was added to the flask over 15-30 min and mixing continued for 3.0 hours. The reaction was monitored for completion by HPLC (limit: not less than 97%). The reaction was diluted with acetonitrile (347 mL, 8.4 mL of ACN/g of Boc-gly-IRT.HCl). The jacket temperature was set to 15° C. and the reaction mixture was concentrated under vacuum until the final residual pot volume was approximately 85% of the initial acetonitrile charge (295-305 mL approximately). The resulting acetonitrile solution was added slowly to a reactor containing methyltert-butyl ether (MTBE, 1632 mL, 39.5 mL of MTBE/g of Boc-gly-IRT-HCl) over a period of 30-60 minutes. The precipitated product was gently mixed for 30 minutes and collected by filtration. The reactor was rinsed with MTBE (410 mL) and the gly-IRT-HCl/TFA filter cake was washed with the rinse. The product was dried under vacuum at 17° C. for a minimum of 12 hours. Yield: 42.1 g (102%).

Step 3. Synthesis of 4-armPEG20K-Irinotecan Hydrochloride-Trifluoroacetate

Gly-IRT HCl-TFA (10.0 g) was charged to a 250 mL reactor and flushed with argon. The jacket temperature was set at 20° C. DCM (166 mL) and TEA (2.94 g) were added. The solution was mixed for 10 minutes. An initial charge of 4-armPEG20K-SCM was added (47.6 g) and the reaction mixture stirred for 30 minutes. A sample was taken and analyzed by HPLC. The HPLC data showed 18% remaining Gly-IRT. A second charge of 4-armPEG20K-SCM (10.7 g) was added to the reaction mixture and the solution stirred for approximately 2 hours. A sample was withdrawn for HPLC analysis. The HPLC analysis data showed 1.5% remaining Gly-IRT. The reaction solution was then slowly added to MTBE (828 mL) to precipitate the product. The precipitate was stirred for 30 minutes and collected via filtration. The wet cake was washed with a mixture of 30% Methanol/70% MTBE (830 mL). The product was then charged to a reactor containing a mixture of 30% Methanol/70% MTBE (642 mL) and the mixture was stirred at 20° C. for 20 minutes. The mixture was filtered and the wet cake was washed on the filter with a mixture of 30% Methanol/70% MTBE (642 ml). The product was dried under vacuum at 20° C.

The dried product was charged to a reactor containing ethyl acetate (642 mL). The mixture was heated to 35° C. to achieve complete dissolution. The warm solution was filtered if necessary to remove undissolved particulates, and then cooled to 10° C. with stirring. The precipitated 4-armPEG20K-glycine-irinotecan hydrochloride-trifluoroacetate product was filtered and the wet cake was washed on the filter with a mixture of 30% Methanol/70% MTBE (642 mL). The product was then dried under vacuum at 20° C. Yield: 54 g (approximately 85%).

Various lots prepared according to the process above were analyzed by ion chromatography for salt composition.

TABLE 2

Mole Percent of Irinotecan bound to PEG

| LOT NO. | TFA SALT | HCl SALT | FREE BASE |
|---|---|---|---|
| Lot 1 | 34 | 41 | 25 |
| Lot 2 | 31 | 45 | 24 |
| Lot 3 | 30 | 49 | 21 |
| Lot 4 | 29 | 48 | 23 |

TABLE 3

Mean and Standard Deviations for Batches in Table 2

|  | MEAN | SD | 2SD | 3SD | 4SD |
|---|---|---|---|---|---|
| TFA, mol % | 31 | 2.4 | 4.8 | 7.2 | 9.6 |
| Cl, mole % | 46 | 3.5 | 7.1 | 10.6 | 14.2 |
| free base, mole % | 23 | 1.0 | 1.9 | 2.9 | 3.9 |

As can be seen from the results in Table 2, batches prepared as described show consistent ratios of TFA salt, hydrochloride salt and free base. Based upon a review of the batch information, it appears that a higher chloride content in the glycine-irinotecan TFA/HCl intermediate leads to a higher chloride content in the final mixed salt conjugate product. By utilizing a starting material such as irinotecan hydrochloride having a fairly constant chloride content, a glycine-irinotecan TFA/HCl salt can be prepared having a fairly constant chloride content.

Based upon a further review of batch information, it appears that the higher the number of TEA equivalents utilized in step 3, the lower the TFA and to a lesser extent, chloride, content in the final mixed salt conjugate product. The measurement of chloride and TFA content of the intermediate, i.e., gly-irinotecan TFA/HCl, facilitated perhaps by greater dissolution of the intermediate prior to analysis, by, for example, ion chromatography, may allow for a more precise determination of stoichiometry. e.g. in the amount of triethylamine added in the final reaction step.

Based upon the foregoing, preferred ranges of TFA in the mixed acid salt conjugate are from about 20 to about 45 mole percent, preferably from about 22 to 40 mole percent, or from about 24 to 38 mole percent. With respect to hydrochloride content, preferred ranges in the mixed acid salt conjugate are from about 30 to 65 mole percent chloride, or from about 32 to 60 mole percent chloride, or from about 35 to 57 mole percent chloride.

EXAMPLE 7

Stress Stability Studies of
4-Arm-PEG-Gly-Irino-20K Materials Having
Differing Salt Ratios Short term (4 week) stability studies were carried out on 4-arm-PEG20K-gly-irinotecan having various salt concentrations as summarized in Table 4 below. "Pure" hydrochloride salt is shown in the far left-hand column while the non-protonated, free base form is shown in the far right column, with varying degradations in-between. The studies were conducted essentially as described in Example 3 over a range of temperatures (−20° C. with no humidity control, 5° C. with no humidity control, 25° C. at 60% relative humidity, and 40° C. at 75% relative humidity.

TABLE 4

| Sample Information | | | | | |
|---|---|---|---|---|---|
| | SAMPLE | | | | |
| | HCl | INTERMED. | REPRESENTATIVE LOT NO. | INTERMED. | FREE BASE |
| | Lot A | Lot B | Lot C | Lot D | Lot E |
| Cl | 0.59% | 0.43% | 0.26% | 0.11% | NQ |
| TFA | NQ | 0.25% | 0.56% | 0.07% | NQ |
| Cl (mol %) | 103.8% | 75.6% | 44.6% | 18.9% | NQ |
| TFA mol % | NQ | 13.6% | 30.6% | 3.9% | NQ |
| Total Salt Mol % | 103.8% | 89.2% | 75.2% | 22.8% | 0% |

For the HCl salt (Lot A), over the course of 4 weeks when evaluated over the range of temperatures, total product related species changed from 98.7% to 97.0% at 40° C., while free irinotecan changed from 0.4% to 1.25%. For the free base, (Lot D), over the course of 4 weeks when evaluated over the range of temperatures, the total product related species changed from 99.8% to 62.5% at 40° C., while free irinotecan changed from 0.3% to 31.4%.

When evaluated under low temperature conditions, at −20° C. and 5° C., over the course of 4 weeks, minimal degradation was observed for each of the materials. When evaluated at 25° C., hydrolysis was observed in each of the species tested with the free base material showing the most significant hydrolytic release of drug. The same was observed at 40° C., where the compositions having the greatest amount of free base demonstrated a correspondingly faster rate of irinotecan hydrolysis. Under the high temperature conditions, i.e., at 40° C., cleavage of the PEG backbone was detected.

EXAMPLE 8

Preparation of Pentaerythitol-Based 4-ARM-PEG-20K at 1.9 Kg Scale

Materials and Methods. A very high grade of ethylene oxide having the lowest water content achievable should be used as water content leads to polymeric diol impurities. CAUTION: Ethylene oxide is a very reactive compound that can react explosively with moisture, thus leaks in the reaction and transfer apparatus should carefully avoided. Also, care should be taken in operations to include having personnel work behind protective shields or in bunkers.

Figure 7:
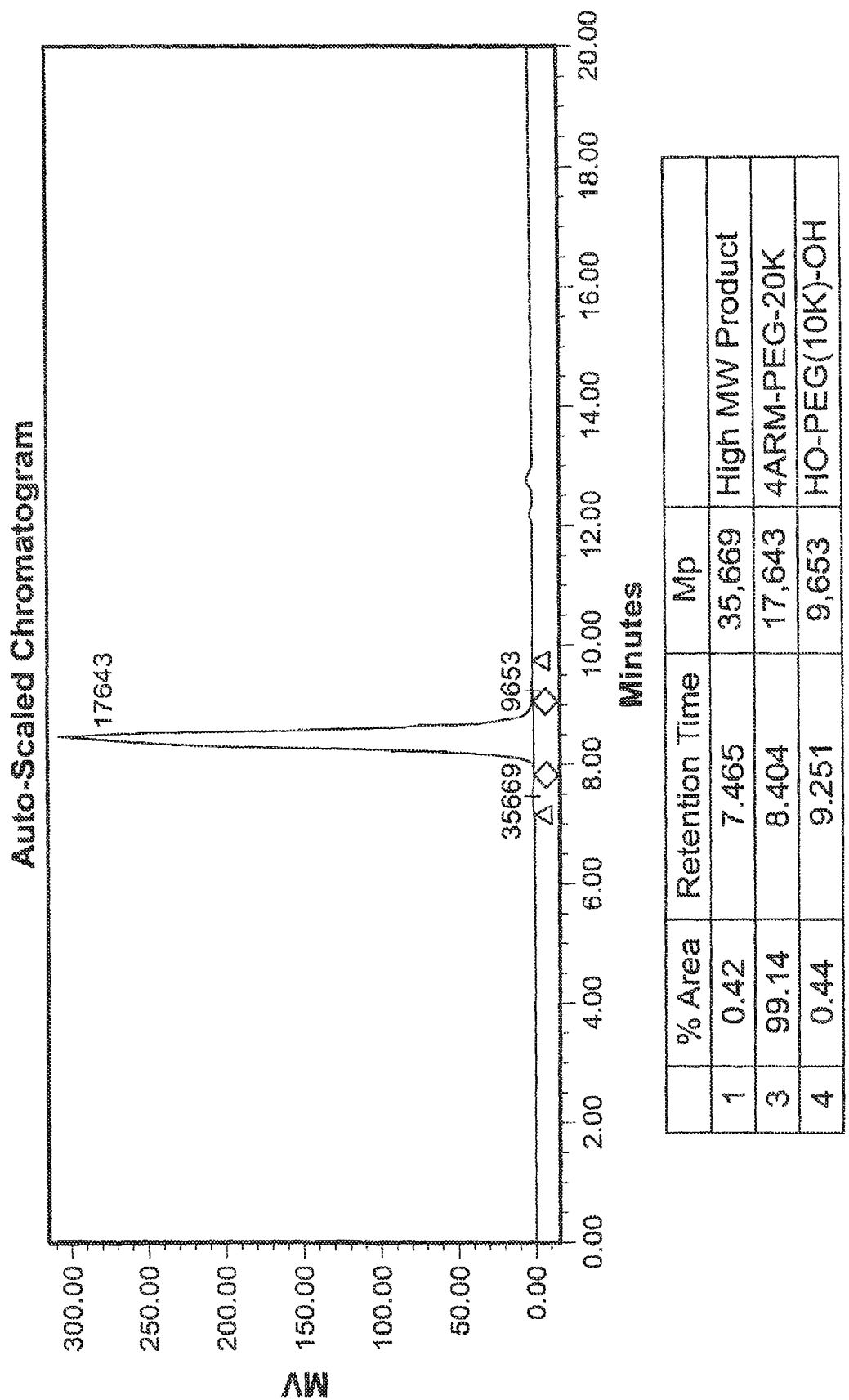
FIG. 7 is a chromatogram following gel filtration chromatography of a material prepared a described in Example 8.

Anhydrous toluene (4 L) was refluxed for two hours in a two gallon jacketed stainless steel pressure reactor. Next, a part of the solvent (3 L) was distilled off under atmospheric pressure. The residual toluene was then discharged out and the reactor was dried overnight by passing steam through the reactor jacket and applying reduced pressure 3-5 mm Hg. Next the reactor was cooled to room temperature, filled with anhydrous toluene (4 L) and pentaerythitol based 4ARM-PEG-2K (SUNBRIGHT PTE®-2000 pentaerythritol, molecular weight of about 2,000 Daltons, NOF Corporation; 200 g. 0.100 moles) was added. The solvent was distilled off under reduced pressure, and then the reactor was cooled to 30° C. under dry nitrogen atmosphere. One liter of molecular sieves-dried toluene (water content ~5 ppm) and liquid sodium-potassium alloy (Na 22%, K 78%; 1.2 g) were added to the reactor. The reactor was warmed to 110° C. and ethylene oxide (1,800 g) was continuously added over three hours keeping the reaction temperature at 110-120° C. Next, the contents of the reactor were heated for two hours at ~100° C., and then the temperature was lowered to ~70° C. Excess ethylene oxide and toluene were distilled off under reduced pressure. After distillation, the contents of the reactor remained under reduced pressure and a nitrogen sparge was performed to remove traces of ethylene oxide. Phosphoric acid (1N) was added to neutralize the basic residue and the product was dried under reduced pressure. Finally the product was drained from the reactor and filtered giving after cooling 1.900 g of white solid. Gel Filtration Chromatography (GFC) was applied to characterize the alkoxylated polymeric product, pentaerythitol based 4-ARM-PEG-20K. This analytical method provided a chromatogram of the composition with separation of the components according to molecular weight. An Agilent 1100 HPLC system equipped with Shodex KW-803 GFC column (300×8 mm) and differential refractometer detector was used. The flow of the mobile phase (0.1M $NaNO_3$) was 0.5 ml/min. The GFC chromatogram is shown in FIG. 7.

GFC analysis showed that the 4ARM-PEG-20K product contained the following: High MW product 0.42%, 4ARM-PEG-20K 99.14%, HO-PEG(10K)-OH 0.44%.

EXAMPLE 9

Analysis of Commercially Available 4ARM-PEG-20K

Figure 8:
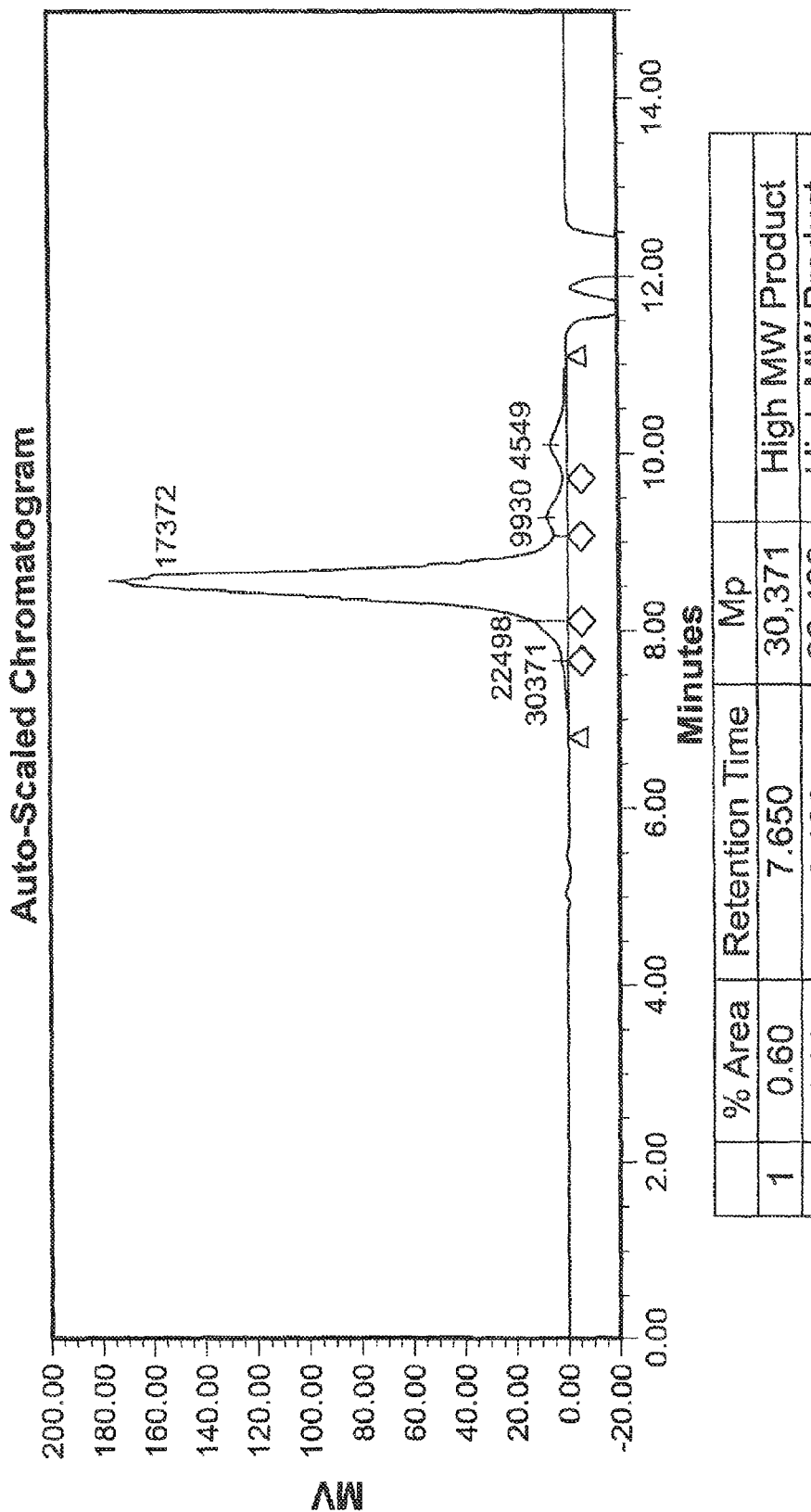
FIG. 8 is a chromatogram following gel filtration chromatography of a material prepared a described in Example 9.

NOF Corporation is a current leader in providing commercial PEGs. Thus a fresh commercially available pentaerythritol-based 4ARM-PEG-20K (SUNBRIGHT PTE®-20,000, molecular weight of about 20,000 Daltons, NOF Corporation) was obtained and analyzed using Gel Filtration Chromatography (GFC). An Agilent 1100 HPLC system equipped with Shodex KW-803 GFC column (300×8 mm) and differential refractometer detector was used. The flow of the mobile phase (0.1M $NaNO_3$) was 0.5 ml/min. The GFC chromatogram is shown in FIG. 8.

GFC analysis showed that this commercial 4ARM-PEG-20K product contained: High MW products 3.93%, 4ARM-PEG-20K 88.56%, HO-PEG(10K)-OH 3.93%, HO-PEG(5K)-OH 3.58%.

EXAMPLE 10

Preparation of Alkoxylatable Oligomer: Pentaerythitol-Based 4-ARM-PEG-2K at 15 Kg Scale A twenty gallon jacketed stainless steel pressure reactor was washed two times with 95 kg of deionized water at 95° C.

The wash water was removed and the reactor was dried overnight by passing steam through the reactor jacket and applying reduced pressure (3-5 mm Hg). The reactor was filled with 25 kg of anhydrous toluene and a part of the solvent was distilled off under reduced pressure. The residual toluene was then discharged out and the reactor was kept under reduced pressure. Next the reactor was cooled to room temperature, filled with anhydrous toluene (15 L) and pentaerythritol (1,020 g) was added. Part of the solvent (~8 L) was distilled off under reduced pressure, and then the reactor was cooled to 30° C. under dry nitrogen atmosphere. Liquid sodium-potassium alloy (Na 22%, K 78%; 2.2 g) was added to the reactor. Anhydrous ethylene oxide (14,080 g) was continuously added over three hours keeping the reaction temperature at 150-155° C. Next, the contents of the reactor were heated for 30 min at ~150° C., and then the temperature was lowered to ~70° C. Excess ethylene oxide and toluene were distilled off under reduced pressure. After distillation, the contents of the reactor remained under reduced pressure and a nitrogen sparge was performed to remove traces of ethylene oxide. Finally the product was drained from the reactor giving 14,200 g of viscous liquid. Gel Filtration Chromatography (GFC) was applied to characterize the product, pentaerythritol based 4-ARM-PEG-2K. This analytical method provided a chromatogram of the composition with separation of the components according to molecular weight. An Agilent 1100 HPLC system equipped with Shodex KW-803 GFC column (300×8 mm) and differential refractometer detector was used. The flow of the mobile phase (0.1M NaNO$_3$) was 0.5 ml/min.

GFC analysis showed that the 4ARM-PEG-2K product was ~100% pure with low or high molecular weight impurities below detectable limits.

EXAMPLE 11

Preparation of Pentaerythritol-Based 4-ARM-PEG-20K at 20 Kg Scale

A twenty gallon jacketed stainless steel pressure reactor was washed two times with 95 kg of deionized water at 95° C. Water was discharged out and the reactor was dried overnight by passing steam through the reactor jacket and applying reduced pressure 3-5 mm Hg. The reactor was filled with 25 kg of toluene and a part of the solvent was distilled off under reduced pressure. The residual toluene was then discharged out and the reactor was kept under reduced pressure. Next the reactor was cooled to room temperature, filled with anhydrous toluene (21 L) and previously isolated alkoxylatable oligomer: pentaerythritol based 4ARM-PEG-2K from the Example 10 (2,064 g) was added. Part of the solvent (16 L) was distilled off under reduced pressure, and then the reactor was cooled to 30° C. under dry nitrogen atmosphere. Four liter of molecular sieves-dried toluene (water content ~5 ppm) and liquid sodium-potassium alloy (Na 22%, K 78%; 1.7 g) were added, and the reactor was warmed to 110° C. Next ethylene oxide (19,300 g) was continuously added over five hours keeping the reaction temperature at 145-150° C. Next, the contents of the reactor were heated for 30 min at ~140° C., and then the temperature was lowered to ~100° C. Glacial acidic acid (100 g) was added to neutralize the catalyst. Excess ethylene oxide and toluene were distilled off under reduced pressure. After distillation, the contents of the reactor remained under reduced pressure and a nitrogen sparge was performed to remove traces of ethylene oxide. Finally the product was drained from the reactor giving 20,100 g of white solid. Gel Filtration Chromatography (GFC) was applied to characterize the alkoxylated polymer product, pentaerythritol based 4-ARM-PEG-20K. This analytical method provided a chromatogram of the composition with separation of the components according to molecular weight. An Agilent 1100 HPLC system equipped with Shodex KW-803 GFC column (300×8 mm) and differential refractometer detector was used. The flow of the mobile phase (0.1M NaNO$_3$) was 0.5 ml/min.

GFC analysis showed that the 4ARM-PEG-20K product contained the following: High MW product 0.75%, 4ARM-PEG-20K 97.92%, HO-PEG(10K)-OH 1.08%, HO-PEG (5K)-OH 0.48%.

The invention(s) set forth herein has been described with respect to particular exemplified embodiments. However, the foregoing description is not intended to limit the invention to the exemplified embodiments, and the skilled artisan should recognize that variations can be made within the spirit and scope of the invention as described in the foregoing specification.

What is claimed is:

1. A composition comprising mixed counter-ions of salts of water-soluble polymer-active agent conjugates having at least one basic tertiary amine group, and further wherein for each tertiary amine group, the tertiary amine group is either protonated or unprotonated, where any given protonated tertiary amine group is an acid salt form of an inorganic acid or trifluoroacetic acid (TFA), and further wherein the water-soluble polymer-active agent conjugates have the following structure

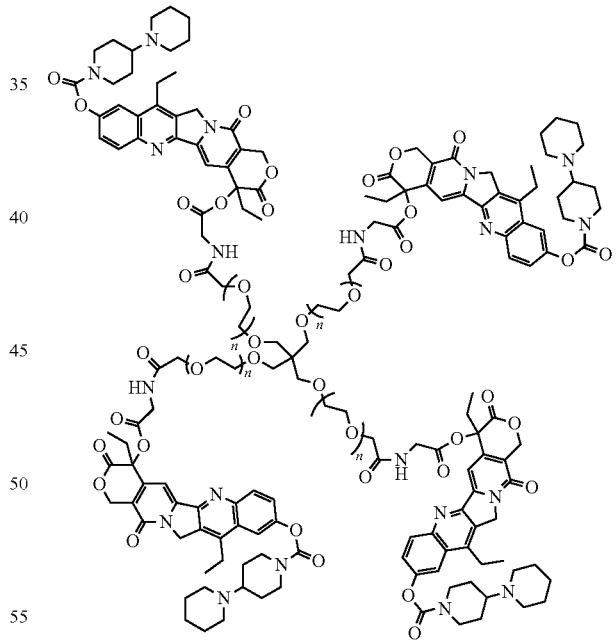

wherein n is an integer ranging from about 20 to about 500, and further wherein at least 25 mole percent of the tertiary amine groups are protonated as the TFA salt, wherein about 25-40 mole percent of the tertiary amine groups are protonated as the HCl salt, and about 5-35 mole percent of the tertiary amine groups within the active agent are non-protonated.

* * * * *